US008795675B2

(12) United States Patent
Wang et al.

(10) Patent No.: US 8,795,675 B2
(45) Date of Patent: Aug. 5, 2014

(54) ALLERGY INHIBITOR COMPOSITIONS AND KITS AND METHODS OF USING THE SAME

(71) Applicants: Bin Wang, Beijing (CN); Huali Jin, Beijing (CN); Youmin Kang, Beijing (CN); Hsien-Jue Chu, Bonner Springs, KS (US); Terry Kaleung Ng, Fort Dodge, IA (US)

(72) Inventors: Bin Wang, Beijing (CN); Huali Jin, Beijing (CN); Youmin Kang, Beijing (CN); Hsien-Jue Chu, Bonner Springs, KS (US); Terry Kaleung Ng, Fort Dodge, IA (US)

( * ) Notice: Subject to any disclaimer, the term of this patent is extended or adjusted under 35 U.S.C. 154(b) by 0 days.

(21) Appl. No.: 13/721,449

(22) Filed: Dec. 20, 2012

(65) Prior Publication Data

US 2013/0230551 A1 Sep. 5, 2013

Related U.S. Application Data

(63) Continuation of application No. 11/644,435, filed on Dec. 22, 2006, now Pat. No. 8,349,333.

(30) Foreign Application Priority Data

Dec. 23, 2005 (CN) .......................... 2005 1 0132381

(51) Int. Cl.
*A61K 38/00* (2006.01)
*A61K 39/00* (2006.01)
*A61K 39/35* (2006.01)
*A61K 39/36* (2006.01)
*C07H 21/04* (2006.01)
*C12N 15/00* (2006.01)
*C12P 15/00* (2006.01)
*C12P 21/06* (2006.01)

(52) U.S. Cl.
USPC .................... 424/185.1; 424/275.1; 435/69.1; 435/455; 435/252.3; 435/320.1; 514/1.1; 536/23.5; 536/24.1

(58) Field of Classification Search
None
See application file for complete search history.

(56) References Cited

U.S. PATENT DOCUMENTS

| 5,804,201 | A | 9/1998 | King |
| 2006/0251667 | A1 | 11/2006 | Chua et al. |
| 2007/0184037 | A1 | 8/2007 | Wang et al. |

FOREIGN PATENT DOCUMENTS

| CN | 1705492 A1 | 12/2005 |
| CN | 1824291 | 8/2006 |
| EP | 1716863 A1 | 11/2006 |
| WO | 9613277 | 5/1996 |
| WO | 97/37676 | 10/1997 |
| WO | 03/047618 A2 | 6/2003 |
| WO | 2004/019978 A1 | 3/2004 |
| WO | 2005/079833 | 9/2005 |
| WO | 2006/063592 A1 | 6/2006 |
| WO | 2007/076084 A2 | 7/2007 |

OTHER PUBLICATIONS

Bischoff et al. 'Role of mast cells in allergic and non-allergic immune responses: comparison of human and murine data.' Nature Rev. 7:93-104, 2007.*
Kurucz et al. 'Current Animal Models of Bronchial Asthma.' Curr. Pharm. Des. 12:3175-3194, 2006.*
Arnon, R., et al., Old and new vaccine approaches, Int Immunopharmacol. Aug. 2003;3(8):1195-204.
ISR for PCT/US06/49161, Oct. 2008.
Akdis, M., et al., T regulatory cells in allergy: novel concepts in the pathogenesis, prevention, and treatment of allergic diseases, J Allergy Clin Immunol. Nov. 2005;116(5):961-8; quiz 969.
Blumenthal et al. 'Definition of an AllergenfAllergens and Allergen Immunotherapy. Ed. R Lockey, S. Bukantz and J. Bousquet. New York: Marcel Decker, 2004.37-50.
Gough et al 'The Cysteine Protease Activity of the Major Dust Mite Allergen Der P 1 Selectively Enhances the Immunoglobulin E Antibody Response.' 190(12):1897-1902, 1999.
Atwood et al. 'The Babel of Bioinformatics.' Science 290:4 71-4 73, 2000.
Skolnick et al. 'From genes to protein structure and function: novel applications of computational approaches in the genomic era.' Trends in Biotechnoloay 18:34-39, 2000.
Metzler et al, 'Solution structure of human CTLA-4 and delineation of a CD80/CD86 binding site conserved in CD28.' Nature 4(7): 527-531, 1997.
Arruda, et al., "Sensitization to Boma tropicals in Patients with Asthma and Identification of Allergen Bio t 5," Am. J. Respir. Crit. Care Med., 155(1):343-350, 1997.
Konieczny A. et al., "The major dog allergens, Can f1 and Can f2, are salivary lipocalin proteins: cloning and immunological characterization of the recombinant forms", Immunology, 1997, 92:577-586.
Smith WA. et al., "Allergens of Wild House Dust Mites: Environmental Oer p. 1 and Der p. 2 sequence polymorphisms", J. Allergy Clin. Immunol., 985-992, 2001.
Bellinghausen, 1., et al., "Human CD4+CD25+ T cells derived from the majority of atopic donors are able to suppress Th 1 and Th2 cytokine production", J. Allergy Clin. Immunol., 111:862-868,2003.
De Kleer, I.M et al., "CD4+CD25 briaht regulatory T cells actively regulate inflammation in the joints of patients with the remitting form of juvenile idiopathic arthritis", f. Immuno/., 172: 6345-6443,2004.

(Continued)

Primary Examiner — Nora Rooney
(74) Attorney, Agent, or Firm — Pepper Hamilton LLP

(57) ABSTRACT

Compositions, methods, and kits for inhibiting an allergic response against an allergenic protein are disclosed. Compositions, methods and kits for inhibiting an allergic response against an flea allergenic protein; a feline allergenic protein; a canine allergenic protein; a dust mite allergenic protein; a peanut allergenic protein; a Japanese cedar allergenic protein; and a *blomia tropicalis* allergenic protein are disclosed.

10 Claims, 21 Drawing Sheets

(56) References Cited

OTHER PUBLICATIONS

Fukara, H., et al., "Induction of circulating myelin basic protein and proteolipid protein-specific transforming growth factor-beta-1-secreting Th3 T cells by oral administration of myelin in multiple sclerosis pateitns", J. Clin. Invest., 98: 70-77, 1996.

Fontenot, J.D., et al.,"Foxp3 programs the development and functon of CD4+CD25+regulatory T cells", Nat. Immunol., 4: 330-336, 2003.

Guidebook for Molecular Cloning Experimentation, 3rd ed., (Chinese translation)(translated by Peitang, H., et al., Science Publishing Company, 2002).

Jilek, S., et al., "Antigen-independent suppression of the allergic immune response to bee venom phospholipase A(2) by DNA vaccination in CBA/J mice", f. Immunol., 166: 3612, 2001.

Jin, H., et al., "Induction of active immune suppression by co-immunization with DNA- and protein-based vaccines", Virology, 337:183-191,2005. (English Abstract provided).

Li, W ., et al., "Combined immunization of DNA vaccine and replication defective recombination adenovirus bearing rabies glycoprotein gene induces immune response against rabies virus",Chin /. Microbial. Immunol., 22:403-406, 2002.

Kumanogoh, A., et al., "Increased T cell autoreactivity in the absence of CD40-CD40 ligand interactions: a role of CD40 in regulatory T cell development", J. Immunol., 166: 353, 2001.

Kearley, J., et al., "Resolution of airway inflammation and hyperactivity after in vivo transfer of CD4+CD25+ regulatory Tcells is interleukin 10 dependent",. J. Exp. Med., 202:1539-47,2005.

Ling, E.M., et al., "Relation of CD4+CD25+ regulaory T-cell suppression of allergen-driven T-cell activation to atopic status and expression of allergic disease", Lancet, 363: 608-615, 2004.

Lundsgaard, T.L., et al., "In vivo control of diabetogenic T-cells by regulatory CD4+CD25+ T-cells expressing Foxp3", Diabetes, 54, p. 1040,2005.

Lee, et al., "Salivary antigens of the cat flea, Ctenocephalides felis felis", Parasite Immunol. 19:13-19, 1997.

Levings, M.K., et al., "Differentiation ofTrl cells by immature dendritic cells requires IL-10 but not CD25+CD4+ Tr cells", Blood, 105: 1162, 2005.

McGeachy, M.J., et al., "Natural recovery and protection from autoimmune encephalomyelitis: contribution of CD4+CD25+ regulatory cells within the central nervous sytem",]. Immunol., 175:3025-3032, 2005.

Proksch, P., et al., "Rocaglamide derivatives are immunosuppressive phytochemicals that target NF-AT activity in T cells", f. Immunol., 174:7075-7084, 2005.

Roncarolo, M.G., et al., "Type 1 T regulatory cells", Immunol. Rev., 182: 68-79, 2001.

Remington's Pharmaceutical Sciences, 171h ed., Mack Publishing Company, Easton, PA ,1985.

Stock, P., et al., "Induction off helper type 1-like regulatory cells that express Foxp3 and protect against airway hyper-reactivity", Nat. Immunol., 5: 1149-1156,2004.

Van Oosterhout, A.J., et al., "Murine CTLA4-lgG treatment inhibits airway eosinophilia and hyperresponsiveness and attenuates lgE upregulation in a murine model of allergic asthma", Am. J. Respir. Cell Mol. Bioi., 17: 386-92, 1997.

Seo, S.K., et al., "4-IBB-mediated immunotherapy of rheumatoid arthritis", Nat. Med., 10: 1088-1094,2004.

McDermott et al., "Identification, cloning, and chracterization of a major cat flea salivary allergen (Cte f 1)", Molecular Immunology, 2000 37:361-375.

Jin, J. et al., "An immunotherapeutic treatment against flea allergy dermatitis in cats by co-immunization of DNA and protein vaccines", Vaccine, 2010, 28(8):1997-2004.

\* cited by examiner

SEQUENCE LISTING

<160> NUMBER OF SEQ ID NOS: 61

<210> SEQ ID NO 1
<211> LENGTH: 640
<212> TYPE: DNA
<213> ORGANISM: Ctenocephalides felis

<400> SEQUENCE: 1

```
atgaattatt gttttttagt attttagta tatttagtat ttgcagttaa tggggaagat      60
atttggaaag ttaataaaaa atgtacatca ggtggaaaaa atcaagatag aaaactcgat    120
caaataattc aaaaaggcca acaagttaaa atccaaaata tttgcaaatt aatacgagat    180
aaaccacata caaatcaaga aaagaaaaa tgtatgaaat tttgcaaaaa agtttgcaaa     240
ggttatagag gagcttgtga tggcaatatt tgctactgca gcaggccaag taatttaggt    300
cctgattgga agtaagcaa agaatgcaaa gatcccaata caaagattc tcgtcctacg     360
gaaatagttc catatcgaca acaattagca attccaaata tttgcaaact aaaaaattca    420
gagaccaatg aagattccaa atgcaaaaaa cattgcaaag aaaaatgtcg tggtggaaat    480
gatgctggat gtgatggaaa cttttgttat tgtcgaccaa aaaataaata ataattataa    540
taaataaatt gttatagtta ttagttatcc catcacatat tagaaaagtg gcttataatt    600
tatgaacaat ataacacata aattagttgt gtaaaaaaaa                         640
```

<210> SEQ ID NO 2
<211> LENGTH: 176
<212> TYPE: PRT
<213> ORGANISM: Ctenocephalides felis

<400> SEQUENCE: 2

```
Met Asn Tyr Cys Phe Leu Val Phe Leu Val Tyr Leu Val Phe Ala Val
1               5                   10                  15

Asn Gly Glu Asp Ile Trp Lys Val Asn Lys Lys Cys Thr Ser Gly Gly
            20                  25                  30

Lys Asn Gln Asp Arg Lys Leu Asp Gln Ile Ile Gln Lys Gly Gln Gln
        35                  40                  45

Val Lys Ile Gln Asn Ile Cys Lys Leu Ile Arg Asp Lys Pro His Thr
    50                  55                  60

Asn Gln Glu Lys Glu Lys Cys Met Lys Phe Cys Lys Lys Val Cys Lys
65                  70                  75                  80

Gly Tyr Arg Gly Ala Cys Asp Gly Asn Ile Cys Tyr Cys Ser Arg Pro
                85                  90                  95

Ser Asn Leu Gly Pro Asp Trp Lys Val Ser Lys Glu Cys Lys Asp Pro
            100                 105                 110

Asn Asn Lys Asp Ser Arg Pro Thr Glu Ile Val Pro Tyr Arg Gln Gln
        115                 120                 125

Leu Ala Ile Pro Asn Ile Cys Lys Leu Lys Asn Ser Glu Thr Asn Glu
    130                 135                 140

Asp Ser Lys Cys Lys Lys His Cys Lys Glu Lys Cys Arg Gly Gly Asn
145                 150                 155                 160

Asp Ala Gly Cys Asp Gly Asn Phe Cys Tyr Cys Arg Pro Lys Asn Lys
                165                 170                 175
```

<210> SEQ ID NO 3
<211> LENGTH: 416
<212> TYPE: DNA
<213> ORGANISM: Ctenocephalides felis

<400> SEQUENCE: 3

```
ggcctggcgg tgctcctgga aaaggatgtt agacgcagcc ctcccaccct gccctactgt    60
tgcggccaca gcagattgtg aaatttgccc agccgtgaag agggatgttg acctattcct   120
gacgggaacc cccgacgaat atgttgagca agtggcacaa tacaaagcac tacctgtagt   180
attggaaaat gccagaatac tgaagaactg cgttgatgca aaaatgacag aagaggataa   240
ggagaatgct ctcagcttgc tggacaaaat atacacaagt cctctgtgtt aaaggagcca   300
tcactgccag agccctaag gaagccactg aactgatcac taagtagtct cagcagcctg   360
ccatgtccag gtgtcttact agaggattcc agcaataaaa gccttgcaat caaac        416
```

<210> SEQ ID NO 4
<211> LENGTH: 88
<212> TYPE: PRT
<213> ORGANISM: Ctenocephalides felis

<400> SEQUENCE: 4

```
Met Leu Asp Ala Ala Leu Pro Pro Cys Pro Thr Val Ala Ala Thr Ala
 1               5                  10                  15
Asp Cys Glu Ile Cys Pro Ala Val Lys Arg Asp Val Asp Leu Phe Leu
                20                  25                  30
Thr Gly Thr Pro Asp Glu Tyr Val Glu Gln Val Ala Gln Tyr Lys Ala
        35                  40                  45
Leu Pro Val Val Leu Glu Asn Ala Arg Ile Leu Lys Asn Cys Val Asp
    50                  55                  60
Ala Lys Met Thr Glu Glu Asp Lys Glu Asn Ala Leu Ser Leu Leu Asp
65                  70                  75                  80
Lys Ile Tyr Thr Ser Pro Leu Cys
                85
```

<210> SEQ ID NO 5
<211> LENGTH: 410
<212> TYPE: DNA
<213> ORGANISM: Ctenocephalides felis

<400> SEQUENCE: 5

```
ctgcatcatg aagggggctc gtgttctcgt gcttctctgg gctgccttgc tcttgatctg    60
gggtggaaat tgtgaaattt gcccagccgt gaagagggat gttgacctat tcctgacggg   120
aacccccgac gaatatgttg agcaagtggc acaatacaaa gcactacctg tagtattgga   180
aaatgccaga atactgaaga actgcgttga tgcaaaaatg acagaagagg ataaggagaa   240
tgctctcagc ttgctggaca aaatatacac aagtcctctg tgttaaagga ccatcactg   300
ccaggagccc taaggaagcc actgaactga tcactaagta gtctcagcag cctgccatgt   360
ccaggtgtct tactagagga ttccagcaat aaaagccttg caattcaaac               410
```

<210> SEQ ID NO 6
<211> LENGTH: 92
<212> TYPE: PRT
<213> ORGANISM: Ctenocephalides felis

<400> SEQUENCE: 6

```
Met Lys Gly Ala Arg Val Leu Val Leu Leu Trp Ala Ala Leu Leu Leu
 1               5                  10                  15
Ile Trp Gly Gly Asn Cys Glu Ile Cys Pro Ala Val Lys Arg Asp Val
                20                  25                  30
Asp Leu Phe Leu Thr Gly Thr Pro Asp Glu Tyr Val Glu Gln Val Ala
```

```
            35                  40                  45
Gln Tyr Lys Ala Leu Pro Val Val Leu Glu Asn Ala Arg Ile Leu Lys
 50                  55                  60

Asn Cys Val Asp Ala Lys Met Thr Glu Glu Asp Lys Glu Asn Ala Leu
 65                  70                  75                  80

Ser Leu Leu Asp Lys Ile Tyr Thr Ser Pro Leu Cys
                 85                  90

<210> SEQ ID NO 7
<211> LENGTH: 525
<212> TYPE: DNA
<213> ORGANISM: Ctenocephalides canis

<400> SEQUENCE: 7
atgaagaccc tgctcctcac catcggcttc agcctcattg cgatcctgca ggcccaggat      60 acccccagcct tgggaaagga cactgtggct gtgtcaggga atggtatct gaaggccatg    120 acagcagacc aggaggtgcc tgagaagcct gactcagtga ctcccatgat cctcaaagcc    180 cagaagggg gcaacctgga agccaagatc accatgctga caaatggtca gtgccagaac    240
atcacggtgg tcctgcacaa aacctctgag cctggcaaat acggcata cgagggccag     300 cgtgtcgtgt tcatccagcc gtccccggtg agggaccact acattctcta ctgcgagggc    360
gagctccatg ggaggcagat ccgaatggcc aagcttctgg gaagggatcc tgagcagagc    420
caagaggcct tggaggattt tcgggaattc tcaagagcca aggattgaa ccaggagatt     480 ttggaactcg cgcagagcga aacctgctct ccaggaggac agtag                    525

<210> SEQ ID NO 8
<211> LENGTH: 174
<212> TYPE: PRT
<213> ORGANISM: Ctenocephalides canis

<400> SEQUENCE: 8

Met Lys Thr Leu Leu Thr Ile Gly Phe Ser Leu Ile Ala Ile Leu
 1               5                  10                  15

Gln Ala Gln Asp Thr Pro Ala Leu Gly Lys Asp Thr Val Ala Val Ser
                 20                  25                  30

Gly Lys Trp Tyr Leu Lys Ala Met Thr Ala Asp Gln Glu Val Pro Glu
             35                  40                  45

Lys Pro Asp Ser Val Thr Pro Met Ile Leu Lys Ala Gln Lys Gly Gly
 50                  55                  60

Asn Leu Glu Ala Lys Ile Thr Met Leu Thr Asn Gly Gln Cys Gln Asn
 65                  70                  75                  80

Ile Thr Val Val Leu His Lys Thr Ser Glu Pro Gly Lys Tyr Thr Ala
                 85                  90                  95

Tyr Glu Gly Gln Arg Val Val Phe Ile Gln Pro Ser Pro Val Arg Asp
                100                 105                 110

His Tyr Ile Leu Tyr Cys Glu Gly Glu Leu His Gly Arg Gln Ile Arg
            115                 120                 125

Met Ala Lys Leu Leu Gly Arg Asp Pro Glu Gln Ser Gln Glu Ala Leu
        130                 135                 140

Glu Asp Phe Arg Glu Phe Ser Arg Ala Lys Gly Leu Asn Gln Glu Ile
145                 150                 155                 160

Leu Glu Leu Ala Gln Ser Glu Thr Cys Ser Pro Gly Gly Gln
                165                 170
```

```
<210> SEQ ID NO 9
<211> LENGTH: 791
<212> TYPE: DNA
<213> ORGANISM: Ctenocephalides canis

<400> SEQUENCE: 9
agagctggac ccgtgtgtgt gctggccaat gagccctgga gggtccggct ccagagtacc      60
ctcttggcac agggccgagt ccatcgggac agatgaacct agaggactcc actgccctcc     120
catccacggg gccgggtcac cagactctgc aagtctccag ctgtcgccaa acccagacag     180
aaggtgctgt ggacatgcag ctcctactgc tgaccgtggg cctggcactg atctgtggcc     240
tccaggctca ggagggaaac catgaggagc cccaggagg cctagaggag ctgtctggga      300
ggtggcactc cgttgccctg gcctccaaca gtccgatct gatcaaaccc tggggggcact    360 tcagggtttt catccacagc atgagcgcaa aggacggcaa cctgcacggg gatatcctta     420
taccgcagga cggccagtgc gagaaagtct ccctcactgc gttcaagact gccaccagca     480
acaaatttga cctggagtac tggggacaca atgacctgta cctggcagag gtagacccca     540
agagctacct gattctctac atgatcaacc agtacaacga tgacaccagc tggtggctc      600 acttgatggt ccgggacctc agcaggcagc aggacttcct gccggcattc gaatctgtat     660
gtgaagacat cggtctgcac aaggaccaga ttgtggttct gagcgatgac gatcgctgcc     720
agggttccag agactagggc ctcagccacg cagagagcca agcagcagga tctcacctgc     780
ctgagtacgg t                                                         791

<210> SEQ ID NO 10
<211> LENGTH: 180
<212> TYPE: PRT
<213> ORGANISM: Ctenocephalides canis

<400> SEQUENCE: 10

Met Gln Leu Leu Leu Thr Val Gly Leu Ala Leu Ile Cys Gly Leu
1               5                   10                  15

Gln Ala Gln Glu Gly Asn His Glu Glu Pro Gln Gly Gly Leu Glu Glu
            20                  25                  30

Leu Ser Gly Arg Trp His Ser Val Ala Leu Ala Ser Asn Lys Ser Asp
        35                  40                  45

Leu Ile Lys Pro Trp Gly His Phe Arg Val Phe Ile His Ser Met Ser
    50                  55                  60

Ala Lys Asp Gly Asn Leu His Gly Asp Ile Leu Ile Pro Gln Asp Gly
65                  70                  75                  80

Gln Cys Glu Lys Val Ser Leu Thr Ala Phe Lys Thr Ala Thr Ser Asn
                85                  90                  95

Lys Phe Asp Leu Glu Tyr Trp Gly His Asn Asp Leu Tyr Leu Ala Glu
            100                 105                 110

Val Asp Pro Lys Ser Tyr Leu Ile Leu Tyr Met Ile Asn Gln Tyr Asn
        115                 120                 125

Asp Asp Thr Ser Leu Val Ala His Leu Met Val Arg Asp Leu Ser Arg
    130                 135                 140

Gln Gln Asp Phe Leu Pro Ala Phe Glu Ser Val Cys Glu Asp Ile Gly
145                 150                 155                 160

Leu His Lys Asp Gln Ile Val Val Leu Ser Asp Asp Arg Cys Gln
                165                 170                 175

Gly Ser Arg Asp
            180
```

<210> SEQ ID NO 11
<211> LENGTH: 1099
<212> TYPE: DNA
<213> ORGANISM: Dermatophagoides pteronyssinus

<400> SEQUENCE: 11

```
gaattccttt tttttctttt ctctctctaa aatctaaaat ccatccaaca tgaaaattgt      60
tttggccatc gcctcattgt tggcattgag cgctgtttat gctcgtccat catcgatcaa     120
aacttttgaa gaatacaaaa aagccttcaa caaaagttat gctaccttcg aagatgaaga     180
agctgcccgt aaaaactttt tggaatcagt aaaatatgtt caatcaaatg gaggtgccat     240
caaccatttg tccgatttgt cgttggatga attcaaaaac cgattttttga tgagtgcaga     300
agcttttgaa caccttcaaaa ctcaattcga tttgaatgct gaaactaacg cctgcagtat     360
caatggaaat gctccagctg aaatcgattt gcgacaaatg cgaactgtca ctcccattcg     420
tatgcaagga ggctgtggtt catgttgggc tttctctggt gttgccgcaa ctgaatcagc     480
ttatttggct taccgtaatc aatcattgga tcttgctgaa caagaattag tcgattgtgc     540
ttcccaacac ggttgtcatg gtgataccat tccacgtggt attgaataca tccaacataa     600
tggtgtcgtc caagaaagct actatcgata cgttgcacga gaacaatcat gccgacgacc     660
aaatgcacaa cgtttcggta tctcaaacta ttgccaaatt tacccaccaa atgtaaacaa     720
aattcgtgaa gctttggctc aaacccacag cgctattgcc gtcattattg gcatcaaaga     780
tttagacgca ttccgtcatt atgatggccg aacaatcatt caacgcgata atggttacca     840
accaaactat cacgctgtca acattgttgg ttacagtaac gcacaaggtg tcgattattg     900
gatcgtacga aacagttggg ataccaattg gggtgataat ggttacggtt attttgctgc     960
caacatcgat tgatgatga ttgaagaata tccatatgtt gtcattctct aaacaaaaag    1020
acaatttctt atatgattgt cactaattta tttaaaatca aaattttag aaaatgaata    1080
aattcattca caaaaatta                                                1099
```

<210> SEQ ID NO 12
<211> LENGTH: 320
<212> TYPE: PRT
<213> ORGANISM: Escherichia coli

<400> SEQUENCE: 12

```
Met Lys Ile Val Leu Ala Ile Ala Ser Leu Leu Ala Leu Ser Ala Val
1               5                   10                  15

Tyr Ala Arg Pro Ser Ser Ile Lys Thr Phe Glu Glu Tyr Lys Lys Ala
                20                  25                  30

Phe Asn Lys Ser Tyr Ala Thr Phe Glu Asp Glu Glu Ala Ala Arg Lys
            35                  40                  45

Asn Phe Leu Glu Ser Val Lys Tyr Val Gln Ser Asn Gly Gly Ala Ile
        50                  55                  60

Asn His Leu Ser Asp Leu Ser Leu Asp Glu Phe Lys Asn Arg Phe Leu
    65                  70                  75                  80

Met Ser Ala Glu Ala Phe Glu His Leu Lys Thr Gln Phe Asp Leu Asn
                85                  90                  95

Ala Glu Thr Asn Ala Cys Ser Ile Asn Gly Asn Ala Pro Ala Glu Ile
                100                 105                 110

Asp Leu Arg Gln Met Arg Thr Val Thr Pro Ile Arg Met Gln Gly Gly
            115                 120                 125

Cys Gly Ser Cys Trp Ala Phe Ser Gly Val Ala Ala Thr Glu Ser Ala
```

```
                130                 135                 140
Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
                180                 185                 190

Arg Tyr Val Ala Arg Glu Gln Ser Cys Arg Arg Pro Asn Ala Gln Arg
                195                 200                 205

Phe Gly Ile Ser Asn Tyr Cys Gln Ile Tyr Pro Pro Asn Val Asn Lys
                210                 215                 220

Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr His Ala Val Asn Ile
                260                 265                 270

Val Gly Tyr Ser Asn Ala Gln Gly Val Asp Tyr Trp Ile Val Arg Asn
                275                 280                 285

Ser Trp Asp Thr Asn Trp Gly Asp Asn Gly Tyr Gly Tyr Phe Ala Ala
                290                 295                 300

Asn Ile Asp Leu Met Met Ile Glu Glu Tyr Pro Tyr Val Val Ile Leu
305                 310                 315                 320

<210> SEQ ID NO 13
<211> LENGTH: 717
<212> TYPE: DNA
<213> ORGANISM: Arachis hypogaea

<400> SEQUENCE: 13
gctcaccata ctagtagccc tcgccctttt cctcctcgct gcccacgcat ctgcgaggca    60
gcagtgggaa ctccaaggag acagaagatg ccagagccag ctcgagaggg cgaacctgag   120
gccctgcgag caacatctca tgcagaagat ccaacgtgac gaggattcat atgaacggga   180
cccgtacagc cctagtcagg atccgtacag ccctagtcca tgatcggaga gaggcgctgg   240
atcctctcag caccaagaga ggtgttgcaa tgagctgaac gagtttgaga caaccaaag    300 gtgcatgtgc gaggcattgc aacagatcat ggagaaccag agcgataggt tgcaggggag   360
gcaacaggag caacagttca gagggagct caggaacttg cctcaacagt gcggccttag    420
ggcaccacag cgttgcgact tggacgtcga agtggcggc agagacagat actaaacacc    480
tatctcaaaa aagaaaaga aagaaaaga aaatagctta tatataagct attatctatg     540
gttatgttta gttttggtaa taataaagat catcactata tgaatgtgtt gatcgtgtta    600
actaaggcaa gcttaggtta tatgagcacc tttagagtgc ttttatggcg ttgtctatgt   660
tttgttgctg cagagttgta accatcttga aataatataa aagatcatg ttttgtt       717

<210> SEQ ID NO 14
<211> LENGTH: 766
<212> TYPE: DNA
<213> ORGANISM: Arachis hypogaea

<400> SEQUENCE: 14
agaaagagaa gacaagatgt cgtggcaaac ctacgtcgat aaccaccttc tctgcgaaat    60
tgaaggcgac cacctctcct ccgccgcaat cctcggccaa gacggcggtg tttgggctca   120
```

```
gagctctcat ttccctcagt tcaagcctga ggaaattact gctatcatga acgactttgc      180
tgagcctgga tcgctcgccc ctaccgggtt gtacctcggt ggcaccaaat acatggttat      240
ccaaggtgaa cccggagcta tcattccagg gaagaagggt cctggtggtg ttaccattga      300
gaagacgaat caggcgttaa tcatcggaat ctacgataag ccaatgactc cggggcagtg      360
caacatgatt gttgaaaggc tgggtgatta tctcattgat acgggtcttt aagtcctctt      420
tgttatttct tgttatctgc ttgcttattt cactggctcc tatacgaggc ttcgcatcga      480
tgtgccaaga gaatgctcga ttgtagtgta ataatattaa ttgatgggta ttcaaaagtc      540
atgggatctg cgtctaggga agaagttatg gtgcttgaga agtgaatgat aactatcatc      600
tctgttgttg tgcttttag cgggtatctg tatacaattt acaagtggtt ttaatgctgt       660
gggcataaat gggcattaaa aaaaaaaaaa aaaaaaaaaa aaaaaaaaaa aaaaaaaaaa      720
aaaaaaaaaa aaaaaaaaaa aaaaaaaaa aaaaaaaaa aaaaa                        766
```

<210> SEQ ID NO 15
<211> LENGTH: 131
<212> TYPE: PRT
<213> ORGANISM: Arachis hypogaea

<400> SEQUENCE: 15

```
Met Ser Trp Gln Thr Tyr Val Asp Asn His Leu Leu Cys Glu Ile Glu
1               5                   10                  15

Gly Asp His Leu Ser Ser Ala Ala Ile Leu Gly Gln Asp Gly Gly Val
            20                  25                  30

Trp Ala Gln Ser Ser His Phe Pro Gln Phe Lys Pro Glu Glu Ile Thr
        35                  40                  45

Ala Ile Met Asn Asp Phe Ala Glu Pro Gly Ser Leu Ala Pro Thr Gly
    50                  55                  60

Leu Tyr Leu Gly Gly Thr Lys Tyr Met Val Ile Gln Gly Glu Pro Gly
65                  70                  75                  80

Ala Ile Ile Pro Gly Lys Lys Gly Pro Gly Gly Val Thr Ile Glu Lys
                85                  90                  95

Thr Asn Gln Ala Leu Ile Ile Gly Ile Tyr Asp Lys Pro Met Thr Pro
            100                 105                 110

Gly Gln Cys Asn Met Ile Val Glu Arg Leu Gly Asp Tyr Leu Ile Asp
        115                 120                 125

Thr Gly Leu
    130
```

<210> SEQ ID NO 16
<211> LENGTH: 1295
<212> TYPE: DNA
<213> ORGANISM: Cryptomeria japonica

<400> SEQUENCE: 16

```
aatctgctca taatcatagc atagccgtat agaaagaaat tctacactct gctaccaaaa       60
aatggattcc ccttgcttag tagcattact ggttttctct tttgtaattg gatcttgctt      120
ttctgataat cccatagaca gctgctggag aggagactca aactgggcac aaaacagaat      180
gaagctcgca gattgtgcag tgggcttcgg aagctccacc atgggaggca agggaggaga      240
tctttatacg gtcacgaact cagatgacga ccctgtgaat cctgcaccag gaactctgcg      300
ctatggagca acccgagata ggcccctgtg ataatttttc agtgggaata tgaatataaa      360
gctcaaaatg cctatgtaca ttgctgggta taagactttt gatggcaggg gagcacaagt      420
```

| | | |
|---|---|---|
| ttatattggc aatggcggtc cctgtgtgtt tatcaagaga gttagcaatg ttatcataca | 480 | |
| cggtttgtat ctgtacggct gtagtactag tgttttgggg aatgttttga taaacgagag | 540 | |
| ttttggggtg gagcctgttc atcctcagga tggcgatgct cttactctgc gcactgctac | 600 | |
| aaatatttgg attgatcata attctttctc caattcttct gatggtctgg tcgatgtcac | 660 | |
| tcttacttcg actggagtta ctatttcaaa caatcttttt ttcaaccatc ataaagtgat | 720 | |
| gttgttaggg catgatgatg catatagtga tgacaaatcc atgaaggtga cagtggcgtt | 780 | |
| caatcaattt ggacctaact gtggacaaag aatgcccagg gcacgatatg gacttgtaca | 840 | |
| tgttgcaaac aataattatg acccatggac tatatatgca attggtggga gttcaaatcc | 900 | |
| aaccattcta agtgaaggga atagtttcac tgcaccaaat gagagctaca agaagcaagt | 960 | |
| aaccatacgt attggatgca aaacatcatc atcttgttca aattgggtgt ggcaatctac | 1020 | |
| acaagatgtt ttttataatg gagcttattt tgtatcatca gggaaatatg aaggggtaa | 1080 | |
| tatatacaca aagaaagaag ctttcaatgt tgagaatggg aatgcaactc ctcaattgac | 1140 | |
| aaaaaatgct ggggttttaa catgctctct ctctaaacgt tgttgatgat gcatatattc | 1200 | |
| tagcatgttg tactatctaa attaacatca acaagaaata tatcatgatg tatattgttg | 1260 | |
| tattgatgtc aaaataaaaa tgttcttta ctatt | 1295 | |

<210> SEQ ID NO 17
<211> LENGTH: 374
<212> TYPE: PRT
<213> ORGANISM: Cryptomeria japonica

<400> SEQUENCE: 17

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Asp Pro Val Asn Pro Ala Pro Gly Thr Leu Arg
65                  70                  75                  80

Tyr Gly Ala Thr Arg Asp Arg Pro Leu Trp Ile Ile Phe Ser Gly Asn
                85                  90                  95

Met Asn Ile Lys Leu Lys Met Pro Met Tyr Ile Ala Gly Tyr Lys Thr
            100                 105                 110

Phe Asp Gly Arg Gly Ala Gln Val Tyr Ile Gly Asn Gly Gly Pro Cys
        115                 120                 125

Val Phe Ile Lys Arg Val Ser Asn Val Ile Ile His Gly Leu Tyr Leu
    130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
            180                 185                 190

Ser Asp Gly Leu Val Asp Val Thr Leu Thr Ser Thr Gly Val Thr Ile
        195                 200                 205

Ser Asn Asn Leu Phe Phe Asn His His Lys Val Met Leu Leu Gly His
    210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
            245                 250                 255

Gly Leu Val His Val Ala Asn Asn Asn Tyr Asp Pro Trp Thr Ile Tyr
        260                 265                 270

Ala Ile Gly Gly Ser Ser Asn Pro Thr Ile Leu Ser Glu Gly Asn Ser
    275                 280                 285

Phe Thr Ala Pro Asn Glu Ser Tyr Lys Lys Gln Val Thr Ile Arg Ile
290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
            325                 330                 335

Glu Gly Gly Asn Ile Tyr Thr Lys Lys Glu Ala Phe Asn Val Glu Asn
        340                 345                 350

Gly Asn Ala Thr Pro Gln Leu Thr Lys Asn Ala Gly Val Leu Thr Cys
    355                 360                 365

Ser Leu Ser Lys Arg Cys
    370

<210> SEQ ID NO 18
<211> LENGTH: 1313
<212> TYPE: DNA
<213> ORGANISM: Cryptomeria japonica

<400> SEQUENCE: 18

```
tagcatagcc gtatagaaag aaattctaca ctctgctacc aaaaaatgga ttccccttgc      60
ttagtagcat tactggtttt ctcttttgta attggatctt gcttttctga taatcccata     120
gacagctgct ggagaggaga ctcaaactgg cacaaaaca gaatgaagct cgcagattgt     180
gcagtgggct tcggaagctc caccatggga ggcaagggag gagatcttta tacggtcacg     240
aactcagatg acgaccctgt gaatcctgca ccaggaactc tgcgctatgg agcaacccga     300
gataggcccc tgtggataat tttcagtggg aatatgaata taaagctcaa aatgcctatg     360
tacattgctg gtataagac ttttgatggc aggggagcac aagtttatat tggcaatggc     420
ggtccctgtg tgtttatcaa gagagttagc aatgttatca tacacggttt gtatctgtac     480
ggctgtagta ctagtgtttt ggggaatgtt ttgataaacg agagttttgg ggtggagcct     540
gttcatcctc aggatggcga tgctcttact ctgcgcactg ctacaaatat ttggattgat     600
cataattctt tctccaattc ttctgatggt ctggtcgatg tcactcttac ttcgactgga     660
gttactattt caaacaatct tttttcaac catcataaag tgatgttgtt agggcatgat     720
gatgcatata gtgatgacaa atccatgaag gtgacagtgg cgttcaatca atttggacct     780
aactgtggac aaagaatgcc agggcacga tatggacttg tacatgttgc aaacaataat     840
tatgacccat ggactatata tgcaattggt gggagttcaa atccaaccat tctaagtgaa     900
gggaatagtt tcactgcacc aaatgagagc tacaagaagc aagtaaccat acgtattgga     960
tgcaaaacat catcatcttg ttcaaattgg gtgtggcaat ctacacaaga tgttttttat    1020
aatggagctt attttgtatc atcagggaaa tatgaagggg gtaatatata cacaaagaaa    1080
gaagctttca atgttgagaa tggaaatgca actcctcaat tgacaaaaaa tgctggggtt    1140
ttaacatgct ctctctctaa acgttgttga tgatgcatat attctagcat gttgtactat    1200
```

```
ctaaattaac atcaacaaga aatatatcat gatgtatatt gttgtattga tgtcaaaata    1260
aaaatgtatc ttttactatt tatcaacatg ttatctttga tgtgcaagtt aat           1313
```

<210> SEQ ID NO 19
<211> LENGTH: 374
<212> TYPE: PRT
<213> ORGANISM: Cryptomeria japonica

<400> SEQUENCE: 19

```
Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Pro Val Asn Pro Ala Pro Gly Thr Leu Arg
65                  70                  75                  80

Tyr Gly Ala Thr Arg Asp Arg Pro Leu Trp Ile Ile Phe Ser Gly Asn
                85                  90                  95

Met Asn Ile Lys Leu Lys Met Pro Met Tyr Ile Ala Gly Tyr Lys Thr
            100                 105                 110

Phe Asp Gly Arg Gly Ala Gln Val Tyr Ile Gly Asn Gly Gly Pro Cys
        115                 120                 125

Val Phe Ile Lys Arg Val Ser Asn Val Ile Ile His Gly Leu Tyr Leu
    130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
            180                 185                 190

Ser Asp Gly Leu Val Asp Val Thr Leu Thr Ser Thr Gly Val Thr Ile
        195                 200                 205

Ser Asn Asn Leu Phe Phe Asn His His Lys Val Met Leu Leu Gly His
    210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                245                 250                 255

Gly Leu Val His Val Ala Asn Asn Asn Tyr Asp Pro Trp Thr Ile Tyr
            260                 265                 270

Ala Ile Gly Gly Ser Ser Asn Pro Thr Ile Leu Ser Glu Gly Asn Ser
        275                 280                 285

Phe Thr Ala Pro Asn Glu Ser Tyr Lys Lys Gln Val Thr Ile Arg Ile
    290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                325                 330                 335

Glu Gly Gly Asn Ile Tyr Thr Lys Lys Glu Ala Phe Asn Val Glu Asn
            340                 345                 350

Gly Asn Ala Thr Pro Gln Leu Thr Lys Asn Ala Gly Val Leu Thr Cys
```

```
                355                 360                 365
Ser Leu Ser Lys Arg Cys
    370

<210> SEQ ID NO 20
<211> LENGTH: 537
<212> TYPE: DNA
<213> ORGANISM: Blomia tropicalis

<400> SEQUENCE: 20
aaaacactca caatccacaa actcaaacaa caatgaagtt cgccatcgtt cttattgcct      60
gctttgccgc ttcggttttg gctcaagagc acaagccaaa gaaggatgat ttccgaaacg     120
aattcgatca cttgttgatc gaacaggcaa accatgctat cgaaaaggga gaacatcaat     180
tgctttactt gcaacaccaa ctcgacgaat tgaatgaaaa caagagcaag gaattgcaag     240
agaaaatcat tcgagaactt gatgttgttt gcgccatgat cgaaggagcc caaggagctt     300
tggaacgtga attgaagcga actgatctta acatttggga acgattcaac tacgaagagg     360
ctcaaactct cagcaagatc ttgcttaagg atttgaagga aaccgaacaa aaagtgaagg     420
atattcaaac ccaataaaaa tttagaattg tacaatttta catttttgat atgattaaat     480
gtcaataaat gttcaataaa taaattcaat ttttaactat aaaaaaaaaa aaaaaaa       537

<210> SEQ ID NO 21
<211> LENGTH: 134
<212> TYPE: PRT
<213> ORGANISM: Blomia tropicalis

<400> SEQUENCE: 21

Met Lys Phe Ala Ile Val Leu Ile Ala Cys Phe Ala Ala Ser Val Leu
1               5                   10                  15
Ala Gln Glu His Lys Pro Lys Lys Asp Asp Phe Arg Asn Glu Phe Asp
                20                  25                  30
His Leu Leu Ile Glu Gln Ala Asn His Ala Ile Glu Lys Gly Glu His
            35                  40                  45
Gln Leu Leu Tyr Leu Gln His Gln Leu Asp Glu Leu Asn Glu Asn Lys
        50                  55                  60
Ser Lys Glu Leu Gln Glu Lys Ile Ile Arg Glu Leu Asp Val Val Cys
65                  70                  75                  80
Ala Met Ile Glu Gly Ala Gln Gly Ala Leu Glu Arg Glu Leu Lys Arg
                85                  90                  95
Thr Asp Leu Asn Ile Leu Glu Arg Phe Asn Tyr Glu Glu Ala Gln Thr
            100                 105                 110
Leu Ser Lys Ile Leu Leu Lys Asp Leu Lys Glu Thr Glu Gln Lys Val
        115                 120                 125
Lys Asp Ile Gln Thr Gln
    130

<210> SEQ ID NO 22
<211> LENGTH: 15
<212> TYPE: PRT
<213> ORGANISM: Artificial Sequence
<220> FEATURE:
<223> OTHER INFORMATION: artificial pep66 peptide; engineered de novo

<400> SEQUENCE: 22

Gln Glu Lys Glu Lys Cys Met Lys Phe Cys Lys Val Cys Lys
1               5                   10                  15
```

```
<210> SEQ ID NO 23
<211> LENGTH: 15
<212> TYPE: PRT
<213> ORGANISM: Artificial Sequence
<220> FEATURE:
<223> OTHER INFORMATION: artificial peptide named pep100; engineered de
      novo

<400> SEQUENCE: 23

Gly Pro Asp Trp Lys Val Ser Lys Glu Cys Lys Asp Pro Asn Asn
1               5                   10                  15

<210> SEQ ID NO 24
<211> LENGTH: 45
<212> TYPE: DNA
<213> ORGANISM: Artificial Sequence
<220> FEATURE:
<223> OTHER INFORMATION: artificial primer sequence named FAD66 primer;
      engineered de novo

<400> SEQUENCE: 24
caagagaaag aaaaatgtat gaaatttttgc aaaaaagttt gcaaa                45

<210> SEQ ID NO 25
<211> LENGTH: 45
<212> TYPE: DNA
<213> ORGANISM: Artificial Sequence
<220> FEATURE:
<223> OTHER INFORMATION: artificial primer sequence named FAD100 primer;
      engineered de novo

<400> SEQUENCE: 25
ggtcctgatt ggaaagtaag caaagaatgc aaagatccca ataac                45

<210> SEQ ID NO 26
<211> LENGTH: 86
<212> TYPE: DNA
<213> ORGANISM: Artificial Sequence
<220> FEATURE:
<223> OTHER INFORMATION: artificial primer sequence named P66F Primer;
      engineered de novo

<400> SEQUENCE: 26
aagcttgcca tgcaagagaa agaaaaatgt atgaaatttt gcaaaaaagt ttgcaaaggt    60
accgccatgg tgagcaaggg cgagga                                        86

<210> SEQ ID NO 27
<211> LENGTH: 30
<212> TYPE: DNA
<213> ORGANISM: Artificial Sequence
<220> FEATURE:
<223> OTHER INFORMATION: artificial primer sequence named PR Primer;
      engineered de novo

<400> SEQUENCE: 27
ttaggtacct tacttgtaca gctcgtccat                                    30

<210> SEQ ID NO 28
<211> LENGTH: 86
<212> TYPE: DNA
<213> ORGANISM: Artificial Sequence
<220> FEATURE:
<223> OTHER INFORMATION: artificial primer sequence named P100F primer;
      engineered de novo

<400> SEQUENCE: 28
```
aagcttgcca tgggtcctga ttggaaagta agcaaagaat gcaaagatcc caataacggt    60
accgccatgg tgagcaaggg cgagga    86

<210> SEQ ID NO 29
<211> LENGTH: 25
<212> TYPE: DNA
<213> ORGANISM: Artificial Sequence
<220> FEATURE:
<223> OTHER INFORMATION: artificial primer sequence named HPRT 5'
      Primer; engineered de novo

<400> SEQUENCE: 29
gttggataca ggccagactt tgttg    25

<210> SEQ ID NO 30
<211> LENGTH: 22
<212> TYPE: DNA
<213> ORGANISM: Artificial Sequence
<220> FEATURE:
<223> OTHER INFORMATION: artificial primer sequence named HPRT 3'
      primer; engineered de novo

<400> SEQUENCE: 30
gagggtaggc tggcctatgg ct    22

<210> SEQ ID NO 31
<211> LENGTH: 22
<212> TYPE: DNA
<213> ORGANISM: Artificial Sequence
<220> FEATURE:
<223> OTHER INFORMATION: artificial primer sequence named IFN-gamma 5'
      primer; engineered de novo

<400> SEQUENCE: 31
cattgaaagc ctagaaagtc tg    22

<210> SEQ ID NO 32
<211> LENGTH: 23
<212> TYPE: DNA
<213> ORGANISM: Artificial Sequence
<220> FEATURE:
<223> OTHER INFORMATION: artificial primer sequence named IFN-gamma 3'
      primer; engineered de novo

<400> SEQUENCE: 32
ctcatggaat gcatcctttt tcg    23

<210> SEQ ID NO 33
<211> LENGTH: 22
<212> TYPE: DNA
<213> ORGANISM: Artificial Sequence
<220> FEATURE:
<223> OTHER INFORMATION: artificial primer sequence named IL-4 5'
      primer; engineered de novo

<400> SEQUENCE: 33
gaaagagacc ttgacacagc tg    22

<210> SEQ ID NO 34
<211> LENGTH: 22
<212> TYPE: DNA
<213> ORGANISM: Artificial Sequence
<220> FEATURE:
<223> OTHER INFORMATION: artificial primer sequence named IL-4 3'
      primer; engineered de novo

<400> SEQUENCE: 34

```
gaactcttgc aggtaatcca gg                                              22

<210> SEQ ID NO 35
<211> LENGTH: 24
<212> TYPE: DNA
<213> ORGANISM: Artificial Sequence
<220> FEATURE:
<223> OTHER INFORMATION: artificial primer sequence named IL-10 5'
      primer; engineered de novo

<400> SEQUENCE: 35
ccagtttacc tggtagaagt gatg                                            24

<210> SEQ ID NO 36
<211> LENGTH: 30
<212> TYPE: DNA
<213> ORGANISM: Artificial Sequence
<220> FEATURE:
<223> OTHER INFORMATION: artificial primer sequence named IL-10 3'
      primer; engineered de novo

<400> SEQUENCE: 36
tgtctaggtc ctggagtcca gcagactcaa                                      30

<210> SEQ ID NO 37
<211> LENGTH: 19
<212> TYPE: DNA
<213> ORGANISM: Artificial Sequence
<220> FEATURE:
<223> OTHER INFORMATION: artificial primer sequence named Fel d I.1 P1
      5' primer; engineered de novo

<400> SEQUENCE: 37
aagcttggat gttagacgc                                                  19

<210> SEQ ID NO 38
<211> LENGTH: 20
<212> TYPE: DNA
<213> ORGANISM: Artificial Sequence
<220> FEATURE:
<223> OTHER INFORMATION: artificial primer sequence named Fel d I.1 P2
      3' primer; engineered de novo

<400> SEQUENCE: 38
ggtaccttaa cacagaggac                                                 20

<210> SEQ ID NO 39
<211> LENGTH: 21
<212> TYPE: DNA
<213> ORGANISM: Artificial Sequence
<220> FEATURE:
<223> OTHER INFORMATION: artificial primer sequence named Fel d I.2 P1
      5' primer; engineered de novo

<400> SEQUENCE: 39
aagcttggat gaaggggct c                                                21

<210> SEQ ID NO 40
<211> LENGTH: 20
<212> TYPE: DNA
<213> ORGANISM: Artificial Sequence
<220> FEATURE:
<223> OTHER INFORMATION: artificial primer sequence named Fel d I.2 P2
      3' primer; engineered de novo

<400> SEQUENCE: 40
```

```
ggtaccttaa cacagaggac                                                       20
```

<210> SEQ ID NO 41
<211> LENGTH: 26
<212> TYPE: DNA
<213> ORGANISM: Artificial Sequence
<220> FEATURE:
<223> OTHER INFORMATION: artificial primer sequence named Can f 1 P1 5'
      primer; engineered de novo

<400> SEQUENCE: 41

```
aagcttatga agaccctgct cctcac                                                26
```

<210> SEQ ID NO 42
<211> LENGTH: 26
<212> TYPE: DNA
<213> ORGANISM: Artificial Sequence
<220> FEATURE:
<223> OTHER INFORMATION: artificial primer sequence named Can f 1 P2 3'
      primer; engineered de novo

<400> SEQUENCE: 42

```
ggtaccctac tgtcctcctg gagagc                                                26
```

<210> SEQ ID NO 43
<211> LENGTH: 23
<212> TYPE: DNA
<213> ORGANISM: Artificial Sequence
<220> FEATURE:
<223> OTHER INFORMATION: artificial primer sequence named Can f 2 P1 5'
      primer; engineered de novo

<400> SEQUENCE: 43

```
aagcttatgc agctcctact gct                                                   23
```

<210> SEQ ID NO 44
<211> LENGTH: 22
<212> TYPE: DNA
<213> ORGANISM: Artificial Sequence
<220> FEATURE:
<223> OTHER INFORMATION: artificial primer sequence named Can f 2 P2 3'
      primer; engineered de novo

<400> SEQUENCE: 44

```
ggtaccctag tctctggaac cc                                                    22
```

<210> SEQ ID NO 45
<211> LENGTH: 25
<212> TYPE: DNA
<213> ORGANISM: Artificial Sequence
<220> FEATURE:
<223> OTHER INFORMATION: artificial primer sequence named Der p 1 P1 5'
      primer; engineered de novo

<400> SEQUENCE: 45

```
aagcttaaca tgaaaattgt tttgg                                                 25
```

<210> SEQ ID NO 46
<211> LENGTH: 25
<212> TYPE: DNA
<213> ORGANISM: Artificial Sequence
<220> FEATURE:
<223> OTHER INFORMATION: artificial primer sequence named Der p 1 P2 3'
      primer; engineered de novo

<400> SEQUENCE: 46

```
ggtaccgttt agagaatgac aacat                                                 25
```

<210> SEQ ID NO 47
<211> LENGTH: 20
<212> TYPE: DNA
<213> ORGANISM: Artificial Sequence
<220> FEATURE:
<223> OTHER INFORMATION: artificial primer sequence named Ara h II P1 5'
      primer; engineered de novo

<400> SEQUENCE: 47
aagcttctca tgcagaagat                                              20

<210> SEQ ID NO 48
<211> LENGTH: 20
<212> TYPE: DNA
<213> ORGANISM: Artificial Sequence
<220> FEATURE:
<223> OTHER INFORMATION: artificial primer sequence named Ara h II P2 3'
      primer; engineered de novo

<400> SEQUENCE: 48
ggtaccttag tatctgtctc                                              20

<210> SEQ ID NO 49
<211> LENGTH: 20
<212> TYPE: DNA
<213> ORGANISM: Artificial Sequence
<220> FEATURE:
<223> OTHER INFORMATION: artificial primer sequence named Ara h 5 P1 5'
      primer; engineered de novo

<400> SEQUENCE: 49
aagcttatgt cgtggcaaac                                              20

<210> SEQ ID NO 50
<211> LENGTH: 20
<212> TYPE: DNA
<213> ORGANISM: Artificial Sequence
<220> FEATURE:
<223> OTHER INFORMATION: artificial primer sequence named Ara h 5 P2 3'
      primer; engineered de novo

<400> SEQUENCE: 50
ggtacctaaa gacccgtatc                                              20

<210> SEQ ID NO 51
<211> LENGTH: 25
<212> TYPE: DNA
<213> ORGANISM: Artificial Sequence
<220> FEATURE:
<223> OTHER INFORMATION: artificial primer sequence named Cry j 1.1 P1
      5' primer; engineered de novo

<400> SEQUENCE: 51
aagcttatgg attcccttg cttat                                         25

<210> SEQ ID NO 52
<211> LENGTH: 23
<212> TYPE: DNA
<213> ORGANISM: Artificial Sequence
<220> FEATURE:
<223> OTHER INFORMATION: artificial primer sequence named Cry j 1.1 P2
      3' primer; engineered de novo

<400> SEQUENCE: 52
ggtaccatca acaacgttta gag                                          23

<210> SEQ ID NO 53
<211> LENGTH: 25
<212> TYPE: DNA
<213> ORGANISM: Artificial Sequence
<220> FEATURE:
<223> OTHER INFORMATION: artificial primer sequence named Cry j 1.2 P1
      5' primer; engineered de novo

<400> SEQUENCE: 53
aagcttatgg attccccttg cttag                                       25

<210> SEQ ID NO 54
<211> LENGTH: 26
<212> TYPE: DNA
<213> ORGANISM: Artificial Sequence
<220> FEATURE:
<223> OTHER INFORMATION: artificial primer sequence named Cry j 1.2 P2
      3' primer; engineered de novo

<400> SEQUENCE: 54
ggtacctcaa caacgtttag agagag                                      26

<210> SEQ ID NO 55
<211> LENGTH: 20
<212> TYPE: DNA
<213> ORGANISM: Artificial Sequence
<220> FEATURE:
<223> OTHER INFORMATION: artificial primer sequence named Blo t 5 P1 5'
      primer; engineered de novo

<400> SEQUENCE: 55
aagcttacaa tgaagttcgc                                             20

<210> SEQ ID NO 56
<211> LENGTH: 20
<212> TYPE: DNA
<213> ORGANISM: Artificial Sequence
<220> FEATURE:
<223> OTHER INFORMATION: artificial primer sequence named Blo t 5 P2 3'
      primer; engineered de novo

<400> SEQUENCE: 56
ggtaccaatt tttattgggt                                             20

<210> SEQ ID NO 57
<211> LENGTH: 21
<212> TYPE: DNA
<213> ORGANISM: Artificial Sequence
<220> FEATURE:
<223> OTHER INFORMATION: artificial primer sequence named Gata 3 5'
      primer; engineered de novo

<400> SEQUENCE: 57
ggaggcatcc agacccgaaa c                                           21

<210> SEQ ID NO 58
<211> LENGTH: 19
<212> TYPE: DNA
<213> ORGANISM: Artificial Sequence
<220> FEATURE:
<223> OTHER INFORMATION: artificial primer sequence named GATA 3 3'
      primer; engineered de novo

<400> SEQUENCE: 58
accatggcgg tgaccatgc                                              19

```
<210> SEQ ID NO 59
<211> LENGTH: 20
<212> TYPE: DNA
<213> ORGANISM: Artificial Sequence
<220> FEATURE:
<223> OTHER INFORMATION: artificial primer sequence named T-bet 5'
      primer; engineered de novo

<400> SEQUENCE: 59
tgaagcccac actcctaccc                                              20

<210> SEQ ID NO 60
<211> LENGTH: 20
<212> TYPE: DNA
<213> ORGANISM: Artificial Sequence
<220> FEATURE:
<223> OTHER INFORMATION: artificial primer sequence named T-bet 3'
      primer; engineered de novo

<400> SEQUENCE: 60
gcggcatttt ctcagttggg                                              20

<210> SEQ ID NO 61
<211> LENGTH: 489
<212> TYPE: DNA
<213> ORGANISM: Artificial Sequence
<220> FEATURE:
<223> OTHER INFORMATION: K-FSA1 insert which includes FSA coding
      sequence linked to a Kozak sequence

<400> SEQUENCE: 61
gccgccacca tggaagatat ttggaaagtt aataaaaaat gtacatcagg tggaaaaaat     60
caagatagaa aactcgatca aataattcaa aaaggccaac aagttaaaat ccaaaatatt    120
tgcaaattaa tacgggataa accacataca aatcaagaga aagaaaaatg tatgaaattt    180
agcaaaaaag tttgcaaagg ttatagagga gcttgtgatg gcaatatttg ctactgcagc    240
aggccaagta atttaggtcc tgattggaaa gtaagcaaag aatgcaaaga tcccaataac    300
aaagattctc ggcctacgga aatagttcca tatcggcagc aattagcaat tccaaatatt    360
tgcaaactaa aaaattcagg gaccaatgaa gattccaaat gcaaaaaaca ttgcaaagaa    420
aaatgtcgtg gtggaaatga tgctggatgt gatggaaact tttgttattg tcggccaaaa    480
aataaataa                                                           489
```

ALLERGY INHIBITOR COMPOSITIONS AND KITS AND METHODS OF USING THE SAME

CROSS REFERENCE TO RELATED APPLICATIONS

This application claims priority under 35 U.S.C. §120 as a continuation of U.S. Ser. No. 11/644,435 filed Dec. 22, 2006, which claims priority to Chinese application number 2005 10132381.X filed Dec. 23, 2005, which is incorporated herein by reference.

FIELD OF THE INVENTION

The present invention relates to compositions and kits which are useful to prevent and inhibit allergic reactions against allergens, and to methods of using such compositions and kits. The present invention provides compositions, kits and methods for preventing and inhibiting flea allergy dermatitis, allergic reactions to cat and canine fur or danders, dust mites, peanuts, Japanese cedar pollen and *blomia tropicalis* allergen.

BACKGROUND OF THE INVENTION

Allergic reactions to various allergens represent significant health concerns, particularly in instances in which the allergic reaction induces severe reactions and/or allergen induced immediate hypersensitivity (AIH).

Allergy is considered as the consequence of persistent T cell activation driving pathogenic inflammation against host dermis by specific allergens. Several approaches are used to ameliorate AIH and these include nonspecific immunosuppressive drugs or monoclonal antibodies targeted to T or B cells (A. J. Van Oosterhout et al., *Am. J. Respir. Cell Mol. Biol.* 17, 386 (Sep. 1, 1997); P. Proksch et al., *J Immunol* 174, 7075 (Jun. 1, 2005)). However, this situation is compromised as long term treated recipients can become generally compromised in their ability to fight infections. Redirecting immunity from Th2 type to Th1 type has also been demonstrated with limited success (S. Jilek, C. Barbey, F. Spertini, B. Corthesy, *J Immunol* 166, 3612 (Mar. 1, 2001)). A recent discovery of T regulatory cells, including the naturally occurring thymus derived CD4$^+$CD25$^+$ Treg cells (I. M. de Kleer et al., *J Immunol* 172, 6435 May 15, 2004); D. Lundsgaard, T. L. Holm, L. Homum, H. Markholst, *Diabetes* 54, 1040 (Apr. 1, 2005); M. J. McGeachy, L. A. Stephens, S. M. Anderton, *J Immunol* 175, 3025 (Sep. 1, 2005); I. Bellinghausen, B. Klostermann, J. Knop, J. Saloga, *J Allergy Clin Immunol* 111, 862 (Apr. 1, 2003); E. M. Ling et al., *Lancet* 363, 608 (Feb. 21, 2004); and J. Kearley, J. E. Barker, D. S. Robinson, C. M. Lloyd, *J. Exp. Med., jem.*20051166 (Nov. 28, 2005)), mucosal induced Th3 cells and antigen induced CD4$^+$CD25$^-$ Tr cells have been proposed to be use as immuno-regulators or suppressors or auto-reactive pathogenesis (H. Fukaura et al., *J. Clin. Invest.* 98, 70 (Jul. 1, 1996)). Various approaches have been explored to induce T regulatory cells to constrain the auto-reactive T cells. Preferentially, induction of antigen specific T regulatory cells targeted to allergy, asthma and autoimmune disease antigens are considered a promising strategy. Several lines of evidence have indicated that induction of antigen specific regulatory T cell 1 (TO) is possible via utility of immatured DCs, suboptimal immunogens or partial blocking the co-stimulatory molecules in DCs (A. Kumanogoh et al., *J Immunol* 166, 353 (Jan. 1, 2001); M. K. Levings et al., *Blood* 105, 1162 (Feb. 1, 2005); and S. K. Seo et al., *Nat Med* 10, 1088 (Oct. 1, 2004)). All these approaches are done either in vitro or in experimental conditions. Induction of Tr cells that can inhibit antigen specific T cells' function in vivo by co-inoculating antigen-matched DNA and protein antigens as co-administered vaccines (H. Jin et al., *Virology* 337, 183 (Jun. 20, 2005)).

The chief characteristic of the non-host flea is that it is a hematophagic parasite that may be found in the body of any mammalian or avian species of animal. *Ctenocephalides felis* is a parasite that occurs mainly in cats and dogs, while *Ctenocephalides canis* is limited to domestic dogs and feral dogs. Flea allergy dermatitis (FAD) is the most frequently seen skin ailment in cats and dogs. FAD results when a flea parasite bites and its saliva serves as an irritant and elicits an allergic reaction. The location of the bite appears red, swollen, irritated and itching. Often the animal will scratch at the bite with its paws, causing the wound to turn into a skin ulceration and eliciting further bacterial and fungal infections. This poses a great danger for the dog or cat and at present no effective pharmacotherapeutic or preventive methods exist for this disease.

In general, flea allergen refers to the various differently sized proteins from flea antigens that cause an allergic reaction. In some parts of the literature it is referred to as feline flea saliva allergenic protein FSA1 or Cte f1. GeneBank AF102502, which is incorporated herein by reference, discloses the nucleotide sequences (SEQ ID NO:1) encoding the FSA1 or Cte fI protein derived from the flea salivary gland of the *Ctenocephalides felis*. The 653 nucleotide sequence includes coding sequences 1-531 which include coding sequences for the signal peptide (1-54) and mature protein sequence (55-528). GeneBank AAD 17905, which is incorporated herein by reference, discloses the amini sequences (SEQ ID NO:2) of the FSA1 or Cte fI protein derived from the flea salivary gland of the *Ctenocephalides felis*, including the signal peptide (1-18) and mature protein sequences (19-176).

The chief feline allergenic protein is Fel dI. GeneBank M74953, which is incorporated herein by reference, discloses the amino acid of and nucleotide sequences (SEQ ID NO:3) encoding the Fel dI protein derived from the major allergen of the domestic cat. It possesses the secondary B secretion peptide sequence. This Fel d I sequence is 416 bp mRNA including the 5' untranslated region made up of sequences 1-25 and the coding sequence being sequences 26-292 encoding 88 amino acids (SEQ ID NO:4; GeneBank AAC41617, which is incorporated herein by reference). The signal peptide is, encoded by 26-79 and the mature protein is encoded by 80-289. The 3' untranslated region is 293-416. GeneBank M74952, which is incorporated herein by reference, discloses the amino acid of and nucleotide sequences (SEQ ID NO:5) encoding the Fel dI protein derived from the major allergen of the domestic cat. This Fel dI sequence is 410 bp mRNA including the 5' untranslated region made up of sequences 1-7 and the coding sequence being sequences 8-286 encoding 92 amino acids (SEQ ID NO:6; GeneBank AAC37318, which is incorporated herein by reference). The signal peptide is encoded by 8-73 and the mature protein is encoded by 74-283. The 3' untranslated region is 287-410.

The chief canine allergenic proteins are the salivary lipid promoters Can f1 and Can f2. GeneBank AF027177, which is incorporated herein by reference, discloses the amino acid of and nucleotide sequences (SEQ ID NO:7) encoding the Can f1 protein derived from the salivary lipocalin proteins of the major allergen of the domestic dog. This Can f1 sequence is 525 bp mRNA encoding 174 amino acids (SEQ ID NO:8; GeneBank AAC48794, which is incorporated herein by reference).

GeneBank AF027178, which is incorporated herein by reference, discloses the amino acid of and nucleotide sequences (SEQ ID NO:9) encoding the Can f2 protein derived from the salivary lipocalin proteins of the major allergen of the domestic dog. This Can f2 sequence is 791 bp mRNA including a coding sequence of 195-737 encoding 180 amino acids (SEQ ID NO:10; GeneBank AAC48795, which is incorporated herein by reference).

GeneBank U11695, which is incorporated herein by reference, discloses the amino acid of and nucleotide sequences (SEQ ID NO:11) encoding the dust mite allergy source protein antigen Der P 1. This Der P1 sequence is 1099 bp mRNA including a coding sequence of 50-1012 encoding 180 amino acids (SEQ ID NO:12; GeneBank AAB60125, which is incorporated herein by reference). The coding sequence includes coding sequences 50-109 which encode a signal peptide and coding sequences 344-1009 which encodes the mature peptide. GeneBank AAB60125 discloses a signal peptide that includes amino acids 1-20 and a mature protein that includes amino acids 99-320.

GeneBank L77197, which is incorporated herein by reference, discloses the amino acid of and nucleotide sequences (SEQ ID NO:13) encoding the peanut allergy source protein antigen Ara h II. This Ara h II sequence is 717 bp sequence encoding 110 amino acids and including a polyA signal 562-567.

GeneBank AF059616, which is incorporated herein by reference, discloses the amino acid of and nucleotide sequences (SEQ ID NO:14) encoding the peanut allergy source protein antigen Ara h II. This Ara h 5 sequence is 743 bp sequence including a coding sequence of 17-412. GeneBank AAD55587, which is incorporated herein by reference, discloses the 131 amino acid protein (SEQ ID NO:15).

GeneBank AB081309, which is incorporated herein by reference, discloses the amino acid of and nucleotide sequences (SEQ ID NO:16) encoding the Japanese cedar (*cryptomeria japonica*) allergy source antigen Cry j 1.1. This Cry j 1.1 sequence is 1295 bp sequence including a coding sequence of 62-1186 in which a signal peptide is encoded by 62-124 and the mature protein is encoded by 125-1183 and a polyA site at 1295. GeneBank BAB86286, which is incorporated herein by reference, discloses the 374 amino acid protein (SEQ ID NO:17) including a signal peptide of amino acids 1-21 and a mature protein of amino acids 22-374.

GeneBank AB081310, which is incorporated herein by reference, discloses the amino acid of and nucleotide sequences (SEQ ID NO:18) encoding the Japanese cedar (*cryptomeria japonica*) allergy source antigen Cry j 1.2. This Cry j 1.2 sequence is 1313 bp sequence including a coding sequence of 46-1170 in which a signal peptide is encoded by 46-108 and the mature protein is encoded by 109-1167 and a polyA site at 1313. GeneBank BAB86287, which is incorporated herein by reference, discloses the 374 amino acid protein (SEQ ID NO:19) including a signal peptide of amino acids 1-21 and a mature protein of amino acids 22-374.

GeneBank U59102, which is incorporated herein by reference, discloses the amino acid of and nucleotide sequences (SEQ ID NO:20) encoding the *blomia tropicalis* allergy source protein antigen Blo t 5. This Blo t 5 sequence is 537 bp sequence including a coding sequence of 33-437. GeneBank AAD10850, which is incorporated herein by reference, discloses the 134 amino acid protein (SEQ ID NO:21).

There remains a need for compositions and methods of preventing and inhibiting the allergic reactions induced by these allergens.

SUMMARY OF THE INVENTION

The present invention relates to compositions for preventing and inhibiting an allergic response against an allergenic protein. The compositions comprise:

a) an eukaryotic cell expression vector containing nucleotide sequences encoding an allergenic protein or a polypeptide that comprises an antigenic epitope of said allergenic protein; and, b) an allergenic protein or a polypeptide that comprises an antigenic epitope of said allergenic protein.

The present invention provides compositions for preventing and inhibiting an allergic response against an allergenic protein selected from the group consisting of a flea allergenic protein; a feline allergenic protein; a canine allergenic protein; a dust mite allergenic protein; a peanut allergenic protein; a Japanese cedar allergenic protein; and a *blomia tropicalis* allergenic protein.

The present invention further relates to kits for preventing and inhibiting an allergic response against an allergenic protein. The kits comprise:

a) a first container comprising a eukaryotic cell expression vector containing nucleotide sequences encoding an allergenic protein or a polypeptide that comprises an antigenic epitope of said allergenic protein; and b) a second container an allergenic protein or a polypeptide that comprises an antigenic epitope of said allergenic protein.

The present invention provides kits for preventing and inhibiting an allergic response against an allergenic protein selected from the group consisting of: a flea allergenic protein; a feline allergenic protein; a canine allergenic protein; a dust mite allergenic protein; a peanut allergenic protein; a Japanese cedar allergenic protein; and a *blomia tropicalis* allergenic protein.

The present invention further relates to methods of preventing and inhibiting an allergic reaction to an allergenic protein in an individual. The methods comprise the step or steps of administering to the individual a) an eukaryotic cell expression vector containing nucleotide sequences encoding an allergenic protein or a polypeptide that comprises an antigenic epitope of said allergenic protein; and b) an allergenic protein or a polypeptide that comprises an antigenic epitope of said allergenic protein.

The present invention provides of preventing and inhibiting an allergic reaction to an allergic protein in an individual wherein said allergenic protein is selected from the group consisting of: a flea allergenic protein; a dust mite allergenic protein; a peanut allergenic protein; a Japanese cedar allergenic protein; and a *blomia tropicalis* allergenic protein.

BRIEF DESCRIPTION OF THE FIGURES

In FIG. 1a, the local reactions after the skin test were measured at 30 min after the challenge. FIG. 1b shows anti-flea antigens of IgE production. In FIG. 1c, CD4+ T cell proliferation responses stimulated by flea antigens in vitro, were tested in mice. Results are representative of at least three experiments. *$P<0.05$, compared with naive control groups as indicated.

FIG. 2a shows data from skin tests of mice after co-immunization with F or pcDF100+F. FIG. 2b shows that dose dependent skin responses in mice after co-immunization with pcDF100+F is displayed. FIG. 2c shows anti-flea antigen levels of IgE and IgG1 after induction and treatment. FIG. 2d shows CD4+ T cell proliferation responses stimulated by flea antigen-specific in vitro. Results are representative of at least three experiments. *P<0.05, compared with V+F and F vaccination groups as indicated.

In FIG. 3a, $5 \times 10^5$ of $CD3^+$ T cells were isolated from the spleens of flea antigen immunized mice and added to 96-well-plates. At the same time, $1 \times 10^5$ of splenocytes from naive, F, V+F and pcDF100+F immunized mice were also added to the same plate. Similarly, $1 \times 10^5$ non-T cells or T cells, purified $CD8^+$, $CD4^+$; or $CD4^+CD25''$ T cells were isolated from the spleens of V+F or pcDF100+F immunized mice. These Co-cultures were stimulated with flea antigen (50 μg/ml) in the presence of $1 \times 10^5$ bone marrow derived DCs for 48 h in vitro. Proliferation was examined by MTS-PMS (Promega) according to manufactors instructions and stimulation index (SI) was determined by the formula: counts of flea-antigen stimulated/counts of non-stimulated cultures). In FIG. 3b, $1 \times 10^6$ of splenocytes from naive, F, V+F and pcDF100+F immunized mice were adoptively transferred into naive C57 mice. Similarly, $1 \times 10^6$ non-T cells or T cells, $1 \times 10^6$ purified $CD8^+$, $CD4^+$, $5 \times 10^5$ $CD4^+CD25^-$ and $CD4^+CD25^+$T cells were isolated from spleens of pcDF100+F, V+F, F immunized or naive control mice and were adoptively transferred into syngeneic flea-antigen primed mice and skin test responses were examined. FIG. 3c shows that co-administration of DNA and protein induce antigen-specific suppression. $1 \times 10^6$ $CD4^+CD25^-$ T cells were isolated from spleens of pcDF100+F, V+F immunized or naive control mice and were adoptively transferred into naive mice, which were then immunized with specific Flea antigen or non-specific OVA protein 24 hours after transfer, then $CD4^+$ T cells were isolated and their proliferation was analyzed. Results shown in the figure are representative of two experiments. *P<0.05 compared with V+F and F transfers as indicated.

FIG. 4a shows pcDF100+F co-immunization restricted MLR stimulatory activities on DCs. 48 h after immunization, DCs isolated from spleen of mice were used to stimulate T cell proliferation in MLR. T cell proliferation was measured by CFSE activity. Results are representative of one of two respective experiments. *P<0.05 compared with V+F and F vaccination groups as indicated. FIG. 4b shows data from DCs isolated from spleens of pcDF100+F, V+F, F immunized or naive control mice co-cultured with nave $CD4^+$ T cells. The T cells were restimulated once for two days for 3 cycles, using fresh DCs, and were then analyzed after each stimulation cycle for IL-10, IL-4 and IFN-γ positive cell numbers, and for the ability to regulated MLR stimulatory activities. In FIG. 4c, MLR was performed with APC from C57 mice and T cells from Balb/c mice. T cell proliferation was measured by CFSE. Results are representative of two individual experiments. *P<0.05 compared with V+F and F vaccination groups as indicated.

DESCRIPTION OF PREFERRED EMBODIMENTS OF THE INVENTION

Figure 1A:
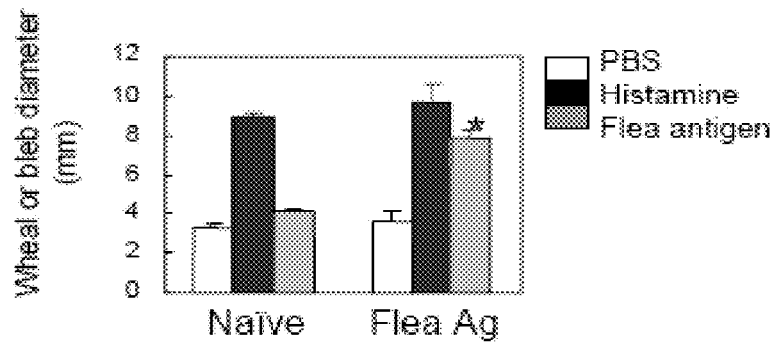
FIGS. 1a-1c refers to a Flea allergy model in mice. C57b/6 mice were primed twice biweekly with flea antigens or saline as a negative control, challenged with the flea antigens, or PBS as the negative control, histamine as the positive control intradermally.

The present invention provides compositions, kits and methods which prevent and inhibit allergic reactions, and allergen induced immediate hypersensitivity. The present invention provides compositions, kits and methods which prevent and inhibit flea allergy dermatitis, compositions, kits and methods which prevent and inhibit feline allergy, compositions, kits and methods which prevent and inhibit canine allergy, compositions, kits and methods which prevent and inhibit mite allergy, compositions, kits and methods which prevent and inhibit peanut allergy, compositions, kits and methods which prevent and inhibit Japanese cedar allergy and compositions, kits and methods which prevent and inhibit *blomia tropicalis* allergy.

The compositions of the invention comprise an allergenic protein or a peptide or protein which comprises an antigenic epitope of the allergenic protein and an expression vector which encodes an allergenic protein or a peptide or protein which comprises an antigenic epitope of the allergenic protein.

The kits of the invention comprise a container that comprises an allergenic protein or a peptide or protein which comprises an antigenic epitope of the allergenic protein and container that comprises an expression vector which encodes an allergenic protein or a peptide or protein which comprises an antigenic epitope of the allergenic protein.

The methods of the invention comprise administering the compositions of the invention and/or the components of a kit of the invention in combination to an individual who has or is susceptible to allergic reactions, or allergen induced immediate hypersensitivity.

The allergenic protein or a peptide or protein which comprises an antigenic epitope of the allergenic protein present in the composition or kit and used in the method, and allergenic protein or a peptide or protein which comprises an antigenic epitope of the allergenic protein encoded by the expression vector present in the composition or kit and used in the method have amino acid sequence overlap such that they share epitopes, i.e at least one epitope of the allergenic protein or a peptide or protein which comprises an antigenic epitope of the allergenic protein present in the composition or kit and used in the method is the same as at least one epitope of the allergenic protein or a peptide or protein which comprises an antigenic epitope of the allergenic protein encoded by the expression vector present in the composition or kit and used in the method. In some embodiments, the allergenic protein or a peptide or protein which comprises an antigenic epitope of the allergenic protein present in the composition or kit and used in the method is the same as the allergenic protein or a peptide or protein which comprises an antigenic epitope of the allergenic protein encoded by the expression vector present in the composition or kit and used in the method. In some embodiments, the allergenic protein or a peptide or protein which comprises an antigenic epitope of the allergenic protein present in the composition or kit and used in the method is a fragment of the allergenic protein or a peptide or protein which comprises an antigenic epitope of the allergenic protein encoded by the expression vector present in the composition or kit and used in the method. In some embodiments, the allergenic protein or a peptide or protein which comprises an antigenic epitope of the allergenic protein encoded by the expression vector present in the composition or kit and used in the method is a fragment of the allergenic protein or a peptide or protein which comprises an antigenic epitope of the allergenic protein present in the composition or kit and used in the method. In some embodiments, the allergenic protein or a peptide or protein which comprises an antigenic epitope of the allergenic protein present in the composition or kit and used in the method is a fragment of the allergenic protein or a peptide or protein which comprises an antigenic epitope of the allergenic protein encoded by the expression vector present in the composition or kit and used in the method. In some embodiments, one or both of 1) the allergenic protein or a peptide or protein which comprises an antigenic epitope of the allergenic protein present in the composition or kit and used in the method and 2) the allergenic protein or a peptide or protein which comprises an antigenic epitope of the allergenic protein encoded by the expression vector present in the composition or kit and used in the method is identical to a naturally occurring protein which is an allergen. In some embodiments, both of 1) the allergenic protein or a peptide or protein which comprises an antigenic epitope of the allergenic protein present in the composition or kit and used in the method and 2) the allergenic protein or a peptide or protein which comprises an antigenic epitope of the allergenic protein encoded by the expression vector present in the composition or kit and used in the method are identical to a naturally occurring protein which is an allergen. In some embodiments, one or both of 1) the allergenic protein or a peptide or protein which comprises an antigenic epitope of the allergenic protein present in the composition or kit and used in the method and 2) the allergenic protein or a peptide or protein which comprises an antigenic epitope of the allergenic protein encoded by the expression vector present in the composition or kit and used in the method is identical to a fragment of a naturally occurring protein which is an allergen. In some embodiments, both of 1) the allergenic protein or a peptide or protein which comprises an antigenic epitope of the allergenic protein present in the composition or kit and used in the method and 2) the allergenic protein or a peptide or protein which comprises an antigenic epitope of the allergenic protein encoded by the expression vector present in the composition or kit and used in the method are identical to a fragment of a naturally occurring protein which is an allergen. In some embodiments, the allergenic protein or a peptide or protein which comprises an antigenic epitope of the allergenic protein present in the composition or kit and used in the method is identical to a fragment of a naturally occurring protein which is an allergen and the allergenic protein or a peptide or protein which comprises an antigenic epitope of the allergenic protein encoded by the expression vector present in the composition or kit and used in the method is identical to a naturally occurring protein which is an allergen. In some embodiments, the allergenic protein or a peptide or protein which comprises an antigenic epitope of the allergenic protein present in the composition or kit and used in the method is identical to a naturally occurring protein which is an allergen and the allergenic protein or a peptide or protein which comprises an antigenic epitope of the allergenic protein encoded by the expression vector present in the composition or kit and used in the method is identical to a fragment of naturally occurring protein which is an allergen.

In some embodiments, the composition or kit includes an allergenic protein such as a protein from a pathogen, food, environmental factor or irritant. In some embodiments, the composition or kit includes a peptide or protein which includes an antigenic epitope of an allergenic protein such as a protein from a pathogen, food, environmental factors or irritant. Similarly, in some embodiments, the composition or kit includes an expression vector which encodes an allergenic protein such as a protein from a pathogen, food or irritant and in some embodiments, the composition or kit includes an expression vector which encodes a peptide or protein which includes an antigenic epitope of an allergenic protein such as a protein from a pathogen, food, environmental factor or irritant.

In some embodiments, an allergenic protein or peptide or protein which includes an antigenic epitope of an allergenic protein that is encoded by the expression vector is identical to the allergenic protein or peptide or protein which includes an antigenic epitope of an allergenic protein included in the composition or kit. In some embodiments, an allergenic protein or peptide or protein which includes an antigenic epitope of an allergenic protein that is encoded by the expression vector is different from the allergenic protein or peptide or protein which includes an antigenic epitope of an allergenic protein included in the composition or kit. In some embodiments, the peptide or protein included in the composition is the allergenic protein. In some embodiments, the peptide or protein included in the composition is a fragment of the allergenic protein. In some embodiments, the peptide or protein encoded by the expression vector is the allergenic protein. In some embodiments, the peptide or protein encoded by the expression vector is a fragment of the allergenic protein. According to the invention, the methods comprise administering the compositions in amounts sufficient to suppress the allergic reaction against the allergenic protein when the individual is subsequently exposed to such protein.

In some embodiments, the present invention provides inhibitors for flea allergy dermatitis. The flea allergy dermatitis inhibitor of the present invention comprises a eukaryotic cell expression vector containing flea salivary allergenic protein (such as fells salivary antigen 1 (FSA1 or Cte f1)) or a peptide or protein that comprises an antigenic epitope of such allergenic protein, in combination with a flea salivary allergenic protein (such as fells salivary antigen 1 (FSA1 or Cte f1)) or a peptide or protein that comprises an antigenic epitope of such allergenic protein.

In some embodiments, the present invention provides inhibitors for feline allergy. The feline allergy inhibitor of the present invention comprises a eukaryotic cell expression vector containing feline allergenic protein (such as Fel dI) or a peptide or protein that comprises an antigenic epitope of such allergenic protein, in combination with a feline allergenic protein (such as Fel dI) or a peptide or protein that comprises an antigenic epitope of such allergenic protein.

In some embodiments, the present invention provides inhibitors for canine allergy. The canine allergy inhibitor of the present invention comprises a eukaryotic cell expression vector containing canine allergenic protein (such as Can f1 or Can f2) or a peptide or protein that comprises an antigenic epitope of such allergenic protein, in combination with a canine allergenic protein (such as Can f1 or Can f2) or a peptide or protein that comprises an antigenic epitope of such allergenic protein.

In some embodiments, the present invention provides inhibitors for dust mite allergy. The dust mite allergy inhibitor of the present invention comprises a eukaryotic cell expression vector containing a dust mite allergy allergenic protein (such as Der P1 or Der F1) or a peptide or protein that comprises an antigenic epitope of such allergenic protein, in combination with a mite allergy allergenic protein (such as Der P1 or Der F1) or a peptide or protein that comprises an antigenic epitope of such allergenic protein.

In some embodiments, the present invention provides inhibitors for peanut allergy. The peanut allergy inhibitor of the present invention comprises a eukaryotic cell expression vector containing a peanut allergy allergenic protein (such as Ara HII or Ara H5) or a peptide or protein that comprises an antigenic epitope of such allergenic protein, in combination with a peanut allergy allergenic protein (such as Ara HII or Ara H5) or a peptide or protein that comprises an antigenic epitope of such allergenic protein.

In some embodiments, the present invention provides inhibitors for Japanese cedar allergy. The Japanese cedar allergy inhibitor of the present invention comprises a eukaryotic cell expression vector containing a Japanese cedar allergy allergenic protein (such as Cry j 1.1 or Cry j 1.2) or a peptide or protein that comprises an antigenic epitope of such allergenic protein, in combination with a Japanese cedar allergy allergenic protein (such as Cry j 1.1 or Cry j 1.2) or a peptide or protein that comprises an antigenic epitope of such allergenic protein.

In some embodiments, the present invention provides inhibitors for *blomia tropicalis* allergy. The *blomia tropicalis* allergy inhibitor of the present invention comprises a eukaryotic cell expression vector containing a *blomia tropicalis* allergy allergenic protein (such as Blo t5) or a peptide or protein that comprises an antigenic epitope of such allergenic protein, in combination with a *blomia tropicalis* allergy allergenic protein (such as Blo t5) or a peptide or protein that comprises an antigenic epitope of such allergenic protein.

The allergenic protein may be expressed in *Escherichia coli* or eukaryotic cells (for example, yeast or CHO cells), for example, molecular cloning methodology is used to incorporate the allergenic protein coding sequence into the corresponding expression vector, causing the protein product to be expressed through the *Escherichia coli*, yeast or CHO cell systems. Purification is then used to obtain the allergenic protein. Similarly, peptides or proteins may be designed which include antigenic epitopes of allergenic proteins. Nucleic acid sequences encoding such peptides or proteins can be incorporated into expression vectors and produced in host cells where they express the peptide or protein which is then purified or peptides may be synthesized. Alternatively, the allergenic protein may be purified from natural sources.

The eukaryotic cell expression vector included in the compositions or kits of the invention may be an expression vector composed of a plasmid expression vector, a viral expression vector or bacteriophage expression vector. Plasmid DNA and chromosome DNA fragment-formed expression vector and other expression vectors are well known and commonly used in the field of genetic engineering. In some embodiments, the plasmid vector pVAX1 (Invitrogen) is used. In some embodiments, the plasmid vector provax which has the CMV promoter, an hCG leader and bovine growth hormone poly A is used. In some embodiments, the plasmid vector is a pcDNA3 plasmid (Invitrogen) which comprises a human cytomegalovirus immediate-early (CMV) promoter, bovine growth hormone polyadenylation signal (BGH polyA), T7 sequence, ColE1 origin of replication, and the JE virus signal sequence.

In the eukaryotic cell expression vectors, the coding sequence for the allergenic protein or peptide or protein that comprises an antigenic epitope of such allergenic protein is operably linked to regulatory sequences required for eukaryotic expression. Examples of suitable promoters include an RSV (Rous sarcoma virus) promoter, a CMV (cytomegalovirus) promoter such as the CMV immediate early promoter, an SV40 virus promoter, Mouse Mammary Tumor Virus (MMTV) promoter, Human Immunodeficiency Virus (HIV) such as the HIV Long Terminal Repeat (LTR) promoter, Moloney virus, ALV, Epstein Barr Virus (EBV), as well as promoters from human genes such as human Actin, human Myosin, human Hemoglobin, human muscle creatine and human metalothionein. Examples of polyadenylation signals useful to practice the present invention, include but are not limited to SV40 polyadenylation signals and LTR polyadenylation signals. In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

In some embodiments, the proportion of eukaryotic cell expression vector to allergenic protein or peptide or protein that comprises an antigenic epitope of such allergenic protein is 1:5-5:1; the preferred option is: 1:1 (the mole ratio is 1-20:100,000; the preferred molar ration is 15:100,000).

In some embodiments, the inhibitor composition or combination of kit components is introduced into the organism intramuscularly, intracutaneously/intradermally, transdermally, subcutaneously, intravenously and through mucosal tissue by means of injection, nebulizer/aerosol/spraying, nose drops, eye drops, orally, sublingual, buccal, vaginal, penetration, absorption, physical or chemical means; or it may be introduced into the organism through other physical mixture or package. The kit components do not have to be delivered together, nor do they have to be delivered at the same site or by the same route of administration.

The pharmaceutical composition may be introduced by various means including, for example, the needle injection, needleless injector, gene gun, electroporation, and microprojectile bombardment.

The composition and kit components may be formulated by one having ordinary skill in the art with compositions selected depending upon the chosen mode of administration. Suitable pharmaceutical carriers are described in the most recent edition of Remington's Pharmaceutical Sciences, A. Osol, a standard reference text in this field.

For parenteral administration, formulations may be provided as a solution, suspension, emulsion or lyophilized powder in association with a pharmaceutically acceptable parenteral vehicle. Examples of such vehicles are water, saline and dextrose solution. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. Injectable compositions may be sterile and pyrogen free.

The dosage administered varies depending upon factors such as: pharmacodynamic characteristics; its mode and route of administration; age, health, and weight of the recipient; nature and extent of symptoms; kind of concurrent treatment; and frequency of treatment. In some embodiments, the amount of composition used or the amount of combination of kit components is generally 1250 µg/kg body weight/administration; with the composition or kit components administered once every 1-30 days, preferably once every 7-14 days. In some embodiments, a single dose is administered. In some embodiments, multiple doses are administered. In some embodiments, a total of 2-3 administrations are administered.

In some embodiments, the compositions or kits are administered to individuals who are suffering from an allergic reaction. In some embodiments, the compositions or kits are administered to individuals who are not suffering from an allergic reaction but who have been exposed to the allergen or likely to have been exposed to the allergen. In some embodiments, the compositions or kits are administered to individuals who are not suffering from an allergic reaction but who are known to be allergic to the allergen, ie. who have previously had allergic responses to the allergen.

The methods of the present invention are useful in the fields of both human and veterinary medicine. Accordingly, the present invention relates to treatment and prevention of allergic reactions in mammals, birds and fish. The methods of the present invention can be particularly useful for mammalian species including human, bovine, ovine, porcine, equine, canine and feline species.

The Examples set out below include representative examples of aspects of the present invention. The Examples are not meant to limit the scope of the invention but rather serve exemplary purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLES

Example 1

Polypeptide Synthesis of Flea Salivary Allergenic Peptides and Construction of a Eukaryotic Cell Expression Vectors for Expression of the Same The described flea salivary allergenic protein (FSA) possesses the amino acid residue sequence as described in SEQ ID NO:2.

The synthesized polypeptide that comprises the amino acid residues described in SEQ ID NO: 22 is named pep66. The synthesized polypeptide that comprises amino acids described in SEQ ID NO: 23 is named pep100.

Nucleotide sequences that encode pep66 have the nucleotide sequence described in SEQ ID NO 24 and are named FAD66.

Nucleotide sequences that encode pep100 have the nucleotide sequence described in SEQ ID NO 25 and are named FAD100.

Eukaryotic vectors that encode pep66 and pep100 comprise at least one nucleotide sequence described in SEQ ID NO 24 or SEQ ID NO: 25 and are named pcDF66 or pcDF100, respectively.

Flea Salivary Allergenic Protein was purchased from the Greer Laboratory Company (Lenoir, N.C., United States) and was formulated by the systematic flea cultivation methods described by Lee, et al., in *Parasite Immunology* 19:13-19, 1997. At the end of one adult year, female fleas were obtained from isolated salivary glands of infected animals. Salivary gland cells were suspended in SDS-reduction buffer and agitated in an oscillator for 30 seconds. Cells were pulverized and crude protein was stored at −20° C.

The described eukaryotic cell expression vectors comprising nucleotide sequences that encode FSA epitopes pep66 and pep100 are named pcDF66 or pcDF100, respectively.

1. Synthesis of FSA Polypeptides Pep66, Pep100, and their Encoded Genes

We verified the amino acid sequences of MHC Class II epitopes of FSA and the chemically synthesized peptides pep66 and pep 100 using Epitlot software. Sequences of the newly synthesized genes and protein products are below:

```
Peptide 66-80:                       (SEQ ID NO: 22)
QEKEKCMKFCKKVCK, called pep66;

Peptide 100-114:                     (SEQ ID NO: 23)
GPDWKVSKECKDPNN, called pep100.
```

Nucleotide sequences that encode pep66 and pep 100 have been named FAD66 and FAD100, respectively. The nucleotide sequences comprise the following sequences:

```
FAD66:                               (SEQ ID NO: 24)
CAAGAGAAAG AAAAATGTAT GAAATTTTGC AAAAAAGTTT GCAAA

FAD100:                              (SEQ ID NO: 25)
GGTCCTGATT GGAAAGTAAG CAAAGAATGC AAAGATCCCA
ATAAC.
```

2. Construction of FAD66 and FAD100 Expression Vectors

Expression vector pGFP (Clontech, Mountain View, Calif., U.S.A) was purchased as a template. We conducted Polymerase chain reaction (PCR) amplification of FSA nucleotide sequences to label the FSA nucleotide sequence with the Green Fluorescent Protein (GFP) gene. Primer extension was completed by use of the P66F and PR primers as well as the P100F and PR primers. Sequences for the primers used in cloning method are as follows: P66F: 5'-AAGCTTGCCA TGCAAGAGAA AGAAAAATGT ATGAAATTTT GCAAAAAAGT TTGCAAAGGTACC GCCATGG TGAG-CAAGGG CGAGGA-3' (SEQ ID NO: 26) (the 13$^{th}$ site—57$^{th}$ site basic group from the 5' terminal end of the amplification product said sequence is FAD66; the 58th site-63rd site basic group from the 5' terminal end of the amplification product is the Kpn I recognition site; the first through sixth basic nucleotide from the 5' terminal end of the amplification product is the Hind III recognition site); PR: 5'-TTA GGTAC-CTTAC TTGTAC AGCTCGTCCAT-3' (SEQ ID NO: 27) (the 4$^{th}$ site-9$^{th}$ site basic group from the 5' terminal end of the amplification product in said sequence is the Kpn I recognition site), P100F: 5'-AAGCTTGCCA TG GGTCCTGA TTGGAAAGTA AGCAAAGAAT GCAAAGATCC CAATAACGGT ACC GCCATGGTGAGCAAGGG-CGAGGA-3' (SEQ ID NO: 28) (the 13$^{th}$ site-57$^{th}$ site basic group from the 5' terminal end of the amplification product in said sequence is FAD66; the 58$^{th}$ site-63$^{rd}$ site basic group from the 5' terminal end of the amplification product is the Kpn I recognition site; the 1$^{st}$ site-6$^{th}$ site basic group from the 5' terminal end of the amplification product in said sequence is the Hind III recognition site), PR: 5'-TTA GGTACCTTAC TTGTAC AGCTCGTCCAT-3' (SEQ ID NO: 27) (the 4$^{th}$ site-9$^{th}$ site basic group from the 5' terminal end of the amplification product is the Kpn I recognition site). PCR product and eukaryotic expression vector pcDNA3 (Invitrogen Corp., Carlsbad, Calif., U.S.A.) were digested using BamH I and Hind III: The amplification product was ligated into the plasmid using T$_4$ DNA ligase, and then transformed into *Escherichia coli* Top 10. After *E. coli* were grown in incubators, plasmid DNA was extracted and restriction digestion was performed using Kpn I to obtain a positive clones. Positive clones included plasmid pcDF66-GFP containing FAD66 and GFP genes and plasmid pcDF100-GFP containing FAD 100 and GFP genes. After using pcDF66-GFP and pcDF 100-GFP for Kpn I digestion, low melting point agarose gel electrophoresis was used to recover large fragments, and then self-binding is conducted. Finally, the product is transformed into *Escherichia coli* Top 10, the plasmid is extracted and restriction endonuclease Kpn I digestion assay is used to obtain a positive clone. Obtained clones included FAD66 expression vector pcDF66 and FAD 100 expression vector pcDF 100.

Normal simian kidney cells (CV1 cells) (purchased from the Institute of Cell Biology, Shanghai) were cultured in DMEM containing 10% fetal calf serum under 5% $CO_2$, and 37° C. Transfections of pcDF66-GFP and pcDF100-GFP were performed on the CV1 cells in a 35 mm culture dish with $2.5 \times 10^5$ cells per/ml and 2 ml per dish. Purification of the plasmids was performed in accordance with the methodology described in the *Guidebook for Molecular Cloning Experimentation* ($3^{rd}$ edition) (Chinese translation) (translated by Huang Peitang et al., Science Publishing Company, published September 2002). A positive ion liposome medium (Lipofectamine™ 2000, Invitrogen) was used to transfect and culture the CV1 cells according to the manufacturer's instructions (Invitrogen, CA, USA). After 24 hours of incubation, the cell culture is observed under fluorescence microscopy showing pcDF100-GFP and pcDF66-GFP was expressed in eukaryotic cells. The results demonstrate that pcDF 100-GFP and pcDF66-GFP also may be expressed in eukaryotic cells.

Example 2

Flea Allergy Dermatitis Inhibitor as Therapy for Flea Allergy Dermatitis

Experiments in which Kunming white, BALB/c and C57BL/6 mice are immunized with a vector comprising FSA protein and nucleotide sequences that encode FSA proteins, or proteins thereof, demonstrate that immunization is an effective therapy for flea allergy dermatitis. Useful vectors for immunization can comprise a eukaryotic cell expression vector further comprising a nucleotide sequences encoding FSA protein (for example, pcDF66 or pcDF 100), and either FSA synthesized peptides (pep66 or pep100) or FSA protein (flea salivary allergenic protein). The immunization efficacy is superior to that of an immunization vector merely comprising a eukaryotic cell expression vector that included nucleotide sequences that encodes either FSA peptides or FSA protein. Inhibition studies demonstrate that the DNA sequences encoding different epitopes have different efficacies. For instance, FAD 100 appears to have a stronger therapeutic effect in suppressing Flea Allergy Dermatitis. Results in each strain of mouse were similar, indicating that immunosuppressive activity of the immunization is not limited to MHC genetic backgrounds. Therefore, we can directly deduce from the above results that through use of a FAD Inhibitor comprising a eukaryotic cell expression vector which further comprises a nucleotide sequence that encodes FSA protein and either a FSA protein or a FSA peptide, it is possible to effectively inhibit flea allergy dermatitis.

T-cell proliferation experiments and related cytokine expansion experiments demonstrate that a FAD Inhibitor, comprising a eukaryotic cell expression vector that encodes FSA protein and an FSA protein or FSA peptide, inhibit antigen-specific T-cell proliferation thereby suppressing an allergic reaction. Immunosuppression may be induced through IL-10, thus inhibiting IL-5, IL-13 and other cytokine expression levels. The FAD Inhibitor in the present invention may effectively prevent and/or treat flea allergy dermatitis, especially those cases caused by *Ctenocephalides felis*.

1. Kunming White Mice Experiments.

Three Hundred Sixty (360) female Kunming white mice were divided into a total of 12 groups of equal numbers. Each mouse in the first group was immunized with 100 microliters of 0.9% NaCl aqueous solution containing 100 micrograms of pcDF66. Each mouse in the second group was immunized with 100 microliters of 0.9% NaCl aqueous solution containing 100 micrograms pep66. Each mouse in the third group was immunized with 100 microliters of 0.9% NaCl aqueous solution containing 50 micrograms of pcDF66 and 50 micrograms of pep66. Each mouse in the fourth group was immunized with 100 microliters of 0.9% NaCl aqueous solution containing 100 micrograms of pcDF 100. Each mouse in the fifth group was immunized with 100 microliters of 0.9% NaCl aqueous solution containing 100 micrograms of pep100. Each mouse in the sixth group was immunized with 100 microliters of 0.9% NaCl aqueous solution containing 50 micrograms of pcDF 100 and 50 micrograms of pep 100. Each mouse in the seventh group was immunized with 100 microliters of 0.9% NaCl aqueous solution containing 50 micrograms of pcDF66 and 50 micrograms of pep100. Each mouse in the eighth group was immunized with 100 microliters of 0.9% NaCl aqueous solution containing 50 micrograms of pcDF100 and 50 micrograms of pep66. Each mouse in the ninth group was immunized with 100 microliters of 0.9% NaCl aqueous solution containing 100 micrograms of inactivated flea antigen (purchased from the Greer Lab Company, North Carolina, United States). Each mouse in the tenth group was immunized with 100 microliters of 0.9% NaCl aqueous solution containing 50 micrograms of inactivated flea antigen (purchased from the Greer Lab Company, North Carolina, United States) and 50 micrograms of pcDF66. Each mouse in the eleventh group was immunized with 100 microliters of 0.9% NaCl aqueous solution containing 50 micrograms of inactivated flea antigen (purchased from the Greer Lab Company, North Carolina, United States) and 50 micrograms of pcDF100. Each mouse in the twelfth group was immunized with 100 microliters of 0.9% NaCl aqueous solution containing 100 micrograms of pcDNA3 to serve as a control. Fourteen days after the first immunization, a booster immunization was administered in the same dosage amount. Seven days after the booster immunization, skin tests were conducted using the following methods.

Hair was removed from the ventral murine chest cavity and an intracutaneous injection of 30 μl of inoculation of 1 μg/ul FSA protein was injected into 10 subjects. At the same time a histamine solution (with a concentration of 0.01% histamine) and PBS was injected in equal amounts to serve as positive controls and negative controls. There were 10 subjects for each control group. Twenty minutes after each injection, we measured blister diameters in micrometers. The t test results indicated that pcDF100 and pep100 compound immunization (the sixth group) demonstrated a notable difference (P<0.05) when compared to pcDF 100 single immunization (the fourth group) or pep100 single immunization (the fifth group). There was a notable difference (P<0.05) between pcDF66 and pep66 compound immunization (the third group) and pcDF66 single immunization (the first group), while there was no notable difference with pep66 single immunization (the second group). Flea antigen and pcDF66 (the tenth group) or pcDF 100 (the eleventh group) compound immunizations were notably different (P<0.05) than the results generated by flea antigen alone (the ninth group), The tenth and eleventh groups did not display any notable difference as compared to pcDF66 (the first group) or pcDF100 (the fourth group) immunizations. There was no difference in blister diameters measured in the sixth and seventh groups as compared to the expression vector or epitope polypeptide single immunity groups (Groups 1, 2, 3 and 4).

Based on the preceding skin test results, we can conclude that a eukaryotic cell expression vector comprising FSA protein or a nucleotide sequence encoding FSA peptide and said FSA peptide, or a eukaryotic cell expression vector comprising FSA protein or a nucleotide sequence that encodes FSA peptides and FSA protein reduces skin allergies in an antigen-specific way. These results indicate that reduction of allergic reactions on the skin may be induced through immunosuppression.

2. BALB/c and C57B/6 Mice Skin Test Results

In order to further verify the results obtained above with Kunming white mice, two pure strains of mice (BALB/c and C57B/6) were tested to determine whether immunosuppression of FAD was MHC restricted. Experimental methodologies were the same as those methodologies performed in the Kunming white mice. The t test results indicate that pcDF100 and pep100 immunization (the sixth group) had no notable difference ($P<0.05$) as compared to pcDF 100 single immunization (the fourth group) or pep100 single immunization (the fifth group). Results from the flea antigen and pcDF 100 compound immunization (the eleventh group) demonstrated a very significant difference ($P<0.01$) compared to the results generated by immunizations of flea antigen (the ninth group) or pcDF100 (the fourth group). There was no significant difference among immunizations of Flea antigen and pcDF66 immunization (the tenth group), flea antigen immunization alone (the ninth group), or pcDF66 immunization alone (the first group). There was no significant difference among pcDF100 and pep66 immunization (the eighth group), pcDF100 immunization alone (the fourth group), or pep66 immunization alone (the second group).

The preceding results indicate that anti-allergic immunosuppression is antigen-specific. For example, immunization with pcDF100 and pep100 was more effective in as compared to immunization with pcDF100 or pep 100 alone. Immunization with the flea antigen and pcDF 100 were more effective than any immunization vectors that included only one component.

Differences also exist in the level of immunosuppression among those groups that effectively treated FAD. For example, the flea antigen and pcDF 100 compound immunity group had more of an effective immunosuppressive effect than compared any of the single immunity groups. The t test results indicate that pcDF 100 and pep100 compound immunity (the sixth group) are significantly different (P43.05) when compared to results of immunization using pcDF100 alone (the fourth group) or pep100 alone (the fifth group). There are significant differences ($P<0.05$) in the immunosuppressive effect of the immunizations performed with pcDF 100 and pep66 compound immunity (the eighth group) as compared to pcDF 100 alone (the fourth group) or pep66 alone (the second group). There was an extremely significant difference ($P<0.01$) in immunizations using Flea antigen and pcDF 100 (the eleventh group) as compared to flea antigen (the ninth group) or pcDF 100 alone (the fourth group).

We interpret our results to conclude that anti-allergic immunosuppression is antigen-specific. For example, immunization was more effective in the pcDF 100 and pep 100 compound immunity group as compared to the pcDF 100 single immunity group or the pep 100 single immunity group. In addition, pep66 and pep 100 peptides may have cross-reactivity. For example, immunization was more effective with pcDF 100 and pep66 immunization as compared to pcDF 100 single immunity group or the pep66 single immunity group. Immunization using the flea antigen and pcDF66 compound immunity did not produce clear immunosuppression. These results are consistent with those obtained in the BALB/c group. Although there are slight differences in the effectiveness of the immunization among each strain of mice studied, experimental results of the three different strains of mice same conclusion: immunization vectors comprising eukaryotic cell expression vectors further comprising FSA protein or nucleotide sequences that encode FSA peptides and FSA peptides; or eukaryotic cell expression vectors comprising FSA protein or nucleotide sequences that encode FSA peptides and FSA protein may mount effective anti-allergic immunosuppression.

Example 3

T-Cell Proliferation in Immunized Mice

Three Hundred Sixty (360) BALB/c mice and three hundred sixty C57B/6 mice were each divided into 12 groups of 30 mice per group. Immunization was performed in accordance with the methodology described in Example 2. At seven days after the booster immunization, splenic T-cells were isolated and T-cell expansion activity was tested. The specific methodology was: under aseptic conditions, splenic cells were taken from mice and used to form a single-cell suspension fluid. A hemolytic solution was used to remove red blood cells, which were then washed three times using PBS fluid. The cells were centrifuged and a cell count taken. Cell concentration was adjusted to $1\times10^6$ cells/ml, and each cell suspension from each animal was divided into four experimental groups and plated into a 96-well culture plate. To one group, 100 μl Con-A (mitogen) was added to a final concentration of 5 μg/ml. Specific antigen (flea antigen) was added to serve as a stimulant to a final concentration of 5 μg/ml to the second group. No stimulant was added for a negative control group, and 100 μl BSA was added to a final concentration of 2 μg/ml to serve as another unrelated antigen. After being incubated at 37° C. in a $CO_2$ culture for 48 h, 100 μl MTS was added to each well at a final concentration of 5 mg/ml. After 4 hours of incubation, an enzyme labeler was used to read the OD value at 492 nm and calculate the stimulation index (SI=tested OD÷non-stimulated OD). T-cell proliferation results for the BALB/c mice indicated that eukaryotic cell expression vectors comprising a nucleotide sequence that encodes FSA peptide flea salivary and said FSA peptide generate notable antigen-specific immunosuppression of FAD. For example, immunization was more effective from the vectors comprising pcDF 100 and pep 100 (the sixth group) and the vectors comprising flea antigen and pcDF100 (the eleventh group) as compared to immunization with vectors comprising single components. In addition, there was no clear immunosuppression demonstrated by immunization vectors comprising the pcDF66 and pep66 group (the third group), the flea antigen and pcDF66 group (the tenth group) as compared to the corresponding single immunity groups. Results using vectors comprising the pcDF100 and pep100 compound immunity group and the flea antigen and pcDF100 compound immunity group are consistent with the immunosuppression effect shown by the skin tests. There was an extremely significant difference ($P<0.01$) in the immunosuppressive effect of the immunization vectors comprising the pcDF100 and pep66 (the eighth group) as compared to the immunosuppressive effect seen in the corresponding single immunity group.

C57B/6 T-cell proliferation results indicate that eukaryotic cell expression vectors containing nucleotide sequences that encode FSA peptide and said FSA peptide may produce clear antigen-specific immunosuppression. For example, there is a clear difference ($P<0.05$) in the effect of immunization of pcDF66 and pep66 compound immunity (the third group) as compared to the corresponding single immunity groups (the first group and the second group). Additionally, there was an extremely significant difference (P<0.01) in the effect of immunization in the pcDF100 and pep100 compound immunity group (the sixth group) as compared to the corresponding single immunity groups (the fourth group and the fifth group). The immunization of mice using vector comprising the flea antigen and pcDF66 (the tenth group) is clearly more effective (P<0.05) than the corresponding single immunity groups (the ninth group and the first group). There was an extremely significant difference (P<0.01) in the effect of the immunization of the flea antigen and pcDF 100 compound immunity group (the eleventh group) as compared to the corresponding single immunity groups (the ninth group and the fourth group). In addition, cross-reactivity exists between the two epitopes. For example, there is a clear difference (P<0.05) in T-cell proliferation profiles with the pcDF66 and pep100 compound immunity group (the seventh group) and the corresponding single immunity groups (the first group and the fifth group). There is also a clear difference (P<0.05) in T-cell proliferation profiles of the pcDF100 and pep66 compound immunity group (the eighth group) and the corresponding single immunity groups (the fourth group and the second group). The T-cell proliferation profiles of in the pcDF 100 and pep 100 compound immunity group, the pcDF 100 and pep66 compound immunity group and the flea antigen and pcDF100 compound immunity group results were all consistent with the skin test results.

response conditions were 42° C. for 30 min, 99° C. for 5 min and 5° C. for 5 minutes. The gene family hypoxanthine phosphoribosyltransferase (HPRT) was used as the internal source expression standard. The various groups' cDNA concentrations were adjusted to make all sample concentrations consistent. Then 41 of cDNA were used to conduct PCR amplification assessing the expression levels of the three cytokine genes: IFN-γ, IL-4, and IL-10. The reaction's required primer and PCR reaction conditions are as indicated in Table 1. (Because the gene family HPRT has fixed expression in vivo, it is used as the template for the control's internal source expression standard).

TABLE 1

HPRT, IFN-γ, IL-4 and IL-10 Primer Sequence and PCR Reaction Specifications.

| Target gene | Primer | Response conditions |
|---|---|---|
| HPRT | 5' GTTGGATACAGGCCAGACTTTGTTG (SEQ ID NO: 29)<br>3' GAGGGTAGGCTGGCCTATGGCT (SEQ ID NO: 30) | 94° C. 30 sec, 60° C. 30 sec and 72° C. 40 sec |
| IFN-γ | 5' CATTGAAAGCCTAGAAAGTCTG (SEQ ID NO: 31)<br>3' CTCATGGAATGCATCCTTTTTCG (SEQ ID NO: 32) | 94° C. 30 sec, 58° C. 30 sec and 72° C. 40 sec |
| IL-4 | 5' GAAAGAGACCTTGACACAGCTG (SEQ ID NO: 33)<br>3' GAACTCTTGCAGGTAATCCAGG (SEQ ID NO: 34) | 94° C. 30 sec, 54° C. 30 sec and 72° C. 40 sec |
| IL-10 | 5' CCAGTTTACCTGGTAGAAGTGATG (SEQ ID NO: 35)<br>3' TGTCTAGGTCCTGGAGTCCAGCAGACTCAA (SEQ ID NO: 36) | 94° C. 30 sec, 56° C. 30 sec and 72° C. 40 sec |

Example 4

Changes in the Cytokine Levels of Immunized Mice

There were 360 Kunming white mice, 360 BALB/c mice, and 360 C57B/6 mice, and each set of subjects strain was divided into 12 groups of 30 mice. Immunization was performed in accordance with the method described in Example 2. Seven days after the booster immunization, the spleen was excised and total RNA (TRIZOL, Dingguo Biological Company) isolated. Reverse transcription for cDNA was performed in accordance with the Dalianbao Biological Company's RNA RT-PCR operating handbook. Briefly 1 μg of purified total RNA was placed in a 250 μL centrifuge tube. Then the following reagents were added in sequence: 4 μl MgCl$_2$, 2 μl 10× buffer solution, 8.5 μl DEPC water, 2 μl dNTP mixture, 0.5 μl RNase inhibitor, 0.5 μl M-MLV reverse transcriptase (Promega), 0.54 Oligo (dT)$_{12}$ primer. The Bio-Rad Image software (Quantity One 4.2.0) was used to analyze images taken of the electrophoresis gels of the PCR products. Expression profile results obtained were generally consistent each strain of mouse. IL-10 expression levels in the pcDF66 and pep66 compound immunity (Group 3) were higher than pcDF66 single immunity (Group 1) and the pep66 single immunity (Group 2). IL-10 expression levels in the pcDF 100 and pep100 compound immunity (Group 6) were higher than pcDF100 single immunity group (Group 4) or pep 100 single immunity group (Group 5). IL-10 expression levels in the flea antigen and pcDF66 compound immunity group (Group 10) were higher than flea antigen (Group 9) or pcDF66 single immunity groups (Group 1). IL-10 expression levels in the flea antigen and pcDF66 compound immunity group (Group 11) were higher than flea antigen (Group 9) or pcDF100 single immunity groups (Group 4). There was no clear difference in the IL-4 and IFN-γ expression levels among the various groups. The results suggest that immunization conducted with eukaryotic cell expression vector comprising nucleotide sequences that encode FSA and said FSA protein or said FSA peptide compound enhanced IL-10 expression levels.

In addition, expression profiles were generated on IL-5 and IL-13 in the three types of mice. Results indicated that for the eukaryotic cell expression vectors comprising nucleotide sequences that encode FSA peptides and said FSA protein or peptide (Group 3, Group 6, Group 10 and Group 11), IL-5 and IL-13 levels were clearly lower than those of the respective single immunity groups.

Example 5

Detection of Blood IgE Levels in Immunized Mice

Two groups of 360 BALB/c and 360 C57B/6 mice were each divided into 12 groups of 30 mice each and immunization was performed as described in Example 2. Blood was taken intravenously from the eye socket prior to immunization and 14 days after the booster immunization. The blood was separated by centrifugation and IgE levels were assessed using ELISA. The coated antigen used on the ELISA plates was flea antigen purchased from Greer Laboratory (Lenoir, N.C., United States). The first component on the ELISA plate was separated blood sera and the second component used for binding was the sheep anti-mice IgE antibody labeled with horseradish peroxidase antioxidant enzyme. The substrate was added to the system after antibody was bound to the antigens and the enzyme labeler was used to read the OD values at 492 nm. The IgE production in Kunming white mice, BALB/c mice, C57B/6 mice after immunization are generally consistent for all three groups of mice. Except for the flea antigen single immunity group (the ninth group), IgE levels for the groups were relatively low. The IgE levels produced after immunization with the flea antigen single immunity group (the ninth group) were the highest levels across all sets of mice. IgE levels were greatly reduced in the group immunized with flea antigen and pcDF66 (the tenth group) and the group immunized with the flea antigen and pcDF 100 (the 11 group) as compared to the flea antigen single immunity group (the ninth group). This indicates that a eukaryotic cell expression vector comprising nucleotide sequences that encode FSA peptides and said FSA protein reduces IgE levels after immunization.

Example 6

Feline Allergenic Protein Antigen Fel d. I.1 (Fel d I with the Minor B Leader) Encoded Genetic Clone and Eukaryotic Expression Assay 1. The following sequences were used as Fel d I.1 primers. Primer were artificially synthesized:

```
(a) Fel d I.1 P1 5'            (SEQ ID NO 37)
primer:
AAGCTTGGATGTTAGACGC (b) Fel d I.1 P2 3'            (SEQ 1D NO 38)
primer:
GGTACCTTAACACAGAGGAC
```

2. Fel d I.1 expression vector construction

Fel d I.1 cDNA was used as a template for PCR amplification of the Fel dI.1 gene using Fel dI.1 P1 and Fel d I.1 P2. The primers are further described below:
(a) Fel d I.1 P1 5'-AAGCTTGGATGTTAGACGC-3' (SEQ ID NO 37) (the $1^{st}$ site-$6^{th}$ site basic group from the 5' terminal end of the primer in this sequence is the Hind III recognition site; the $9^{th}$ site-$11^{th}$ site is the original initiator code);
(b) Fel d I.1 P2 5' GGTACCTTAACACAGAGGAC-3' (SEQ ID NO 38) (the $1^{st}$ site-$6^{th}$ site basic group from the 5' terminal end of the primer in this sequence is the Kpn I recognition site; the $7^{th}$ site-$9^{th}$ site is the original termination code).

Kpn I and Hind III, respectively, were used for digesting the PCR product and eukaryotic expression vector pVAX 1 (Invitrogen Corp.). Digested nucleotide fragments were then ligated using $T_4$ DNA ligase. The resultant plasmid product was transformed into *Escherichia coli* Top 10, grown for maximum copy number, and then the plasmid isolated using methods known by those of ordinary skill in the art. We performed a restriction digestion using the Kpn I and Hind III endonucleases. Selected plasmid clones named pVAX1-Fel d I.1 comprised the pVax plasmids sequence and the Fel d I.1 gene. Through sequential analysis (Auget Co: Ltd., Beijing China), further analysis was performed to obtain the final Fel d I.1 P1 expression vector, pFeld I.1.

3. pFeldI.1 Eukaryotic Expression

Normal simian kidney cells (CV1 cells, purchased from the Shanghai Cell Institute) were cultured in DMEM containing 10% fetal calf serum under 5% $CO_2$ and 37° C. conditions. $2.5 \times 10^5$ cells per/ml were pipeted in a 35 mm culture dishes in a 2 mL volume. Transfections were performed using standard methods. Briefly, purification of the plasmids was performed in accordance with the methodology in the Guidebook for Molecular Cloning Experimentation (third edition, Chinese translation) (translated by Huang Peitang et al., Science Publishing Company, published September 2002). A positive ion liposome medium (Lipofectamine™ 2000, Invitrogen) was used to transfect the cultured CV1 cells according to the manufacturer's instructions (Invitrogen, CA, USA). After 24 hours of transfection, the cells were collected and an RNA extraction reagent (TRIZOL, Dingguo Biological Company) was used to isolate total cellular RNA. In order to prevent contamination, total extracted RNA was separately loaded into several EP tubes. A micropipette was used to carefully suction 2 ul of total RNA extracted and RT-PCR reagent used to expand total cellular cDNA. After the specimen was added, reverse transcription was performed at 42° C. for 30-60 minutes, denaturation at 99° C. for 5 minutes, and The reaction tube was set aside at 5° C. for 5 minutes prior to extraction for use. Using the isolated cDNA as a template for gene amplification PCR was performed using FeldI.1P1 and FeldI.1P2 as the primers. The PCR products were subject to low melting point agarose gel analysis to detect FeldI.1 positive bands. The results demonstrate that FeldI.1 is expressed in eukaryotic cells.

Example 7

Feline Allergenic Protein Antigen Feld. 1.2 Genetic Clone and Eukaryotic Expression Assay 1. The following sequences were used as Fel d I.2 primers. Primers were artificially synthesized:

```
(a) Fel d I.2 P1 5'            (SEQ ID NO: 39)
primer:

AAGCTTGGATGAAGGGGGCTC (b) Fel d I.2 P2 3'            (SEQ ID NO: 40)
primer:

GGTACCTTAACACAGAGGAC
```

2. Fel d I.2 expression vector construction

Fel d I.2 cDNA was used as a template for PCR amplification using Fel d I.2 P1 and Fel d I.2 P2 primers to generate copies of the Fel d I.2 gene. The primers are further described below: (a) Fel d I.2 P1 5'-AAGCTTGGAT-GAAGGGGGCTC-3' (SEQ ID NO:39) (the $1^{st}$ site-$6^{th}$ site basic group from the 5' terminal end of the primer is the Hind III recognition site; the $9^{th}$ site-$11^{th}$ site from the terminal end of the primer is the original initiator code); (b) Fel d 1.2 P2 5'-GGTACCTTAACACAGAGGAC-3' (SEQ ID NO:40) (the $1^{st}$ site-$6^{th}$ site basic group from the 5' terminal end of the primer is the Kpn I recognition site, the $7^{th}$ site-$9^{th}$ site from the terminal end of the primer is the original termination code).

Kpn I and Hind III in succession were used for digesting the PCR product and eukaryotic expression vector, pVAX 1 (Invitrogen Corp.). The digested plasmid and PCR product were ligated using $T_4$ DNA ligase. The product was transformed into *Escherichia coli* Top 10, the plasmid extracted, and restriction endonuclease Kpn I and Hind III digestion assay used to obtain a positive clone, that is, plasmid pVAX1-Fel d I.2 containing the Can f1 gene. Through sequential analysis (Auget Co. Ltd., Beijing China), further assay correction was performed to obtain the Fel d I.2 expression vector, pFeld I.2.

3. pFeld1.2 Eukaryotic Expression

The pFeld I.2 expression vector was subjected to the digestion, transformation, isolation, and ligation protocols previously described in Example 6, Section 3. Isolated PCR products were subjected to low melting point agarose gel testing to confirm FeldI.2 positive bands. The results prove that FeldI.2 is expressed in eukaryotic cells.

Example 8

Canine Allergenic Protein Antigen can f 1 Genetic Clone and Eukaryotic Expression Assay 1. Can f1 Primer Synthesis The following sequences were used as Can f1 primers. Primers were artificially synthesized:

```
Can f 1 P1 5' primer:              (SEQ ID NO: 41)
AAGCTTATGAAGACCCTGCTCCTCAC Can f 1 P2 3' primer:              (SEQ ID NO: 42)
GGTACCCTACTGTCCTCCTGGAGAGC
```

2. Can f1 Expression Vector Construction

Can f1 cDNA was used as a template to perform PCR amplification using Can f1 P1 and Can f1 P2 primers to generate copies of the Can f1 gene. The primers are further described below: (a) Can f1 P1 5'-AAGCTTATGAAGACCCTGCTCCTCAC-3' (SEQ ID NO:41) (the $1^{st}$ site-$6^{th}$ site basic group from the 5' terminal end of the primer sequence is the Hind III recognition site; the $7^{th}$ site-$9^{th}$ site from the terminal end of the primer sequence is the original initiator code); (b) Can f1 P2 5'-GGTACCCTACTGTCCTCCTGGAGAGC-3' (SEQ ID NO:42) (the $1^{st}$ site-$6^{th}$ site basic group from the 5' terminal end of the primer sequence is the Kpn I recognition site; the $7^{th}$ site-$9^{th}$ site from the %' terminal end of the sequence is the original termination code).

PCR fragments and pVAX1 (Invitrogen, Inc.) were subjected to the digestion, transformation, isolation, and ligation methods as described in Example 7, Section 2. Positive clones were selected and analyzed using sequential analysis discussed in Example 7, Section 2 to obtain the Can f1 expression vector, pCanf1.

3. pCanf1 Eukaryotic Expression

The pCanf1 expression vector was subjected to transfection, total RNA isolation, and RT-PCR protocols as previously described in Example 6, Section 3. Isolated PCR products were subjected to low melting point agarose gel testing to confirm pCanf1 positive bands. The results prove that pCanf1 is expressed in eukaryotic cells.

Example 9

Canine Allergenic Protein Antigen can 12 Genetic Clone and Eukaryotic Expression Assay 1. Can f2 Primer Synthesis The following sequences were used as Can f2 primers. Primers were artificially synthesized:

```
Can f 2 P1 5' primer:              (SEQ ID NO: 43)
AAGCTT ATGCAGCTCCTACTGCTG
```

-continued

```
Can f 2 P2 3' primer:              (SEQ ID NO: 44)
GGTACCCTAGTCTCTGGAACCC
```

2. Can f2 Expression Vector Construction

Can f2 cDNA cDNA was used as a template to perform PCR amplification using Can f 2 P 1 and Can f2 P2 primers to generate copies of the Can f2 gene. The primers are further described below: (a) Can f2 P15'-AAGCTT ATGCAGCTCCTACTGCTG-3' (SEQ ID NO:43) (the $1^{st}$ site-$6^{th}$ site basic group from the 5' terminal end of the primer sequence is the Hind III recognition site; the $7^{th}$ site-$9^{th}$ site is the original initiator code); (b) Can f2 P2 5'-GGTACCCTAGTCTCTGGAACCC-3' (SEQ ID NO:44) (the $1^{st}$ site-$6^{th}$ site basic group from the 5' terminal end of this primer sequence is the Kpn I recognition site, the $7^{th}$ site-$9^{th}$ site is the original termination code).

PCR fragments and pVAX1 (Invitrogen, Inc.) were subjected to the digestion, transformation, isolation, and ligation methods as described in Example 7, Section 2. Positive clones were selected and analyzed using sequential analysis discussed in Example 7, Section 2 to obtain the Can f2 expression vector, pCanf2.

3. pCanf2 Eukaryotic Expression

The pCanf2 expression vector was subjected to transfection, total RNA isolation, and RT-PCR protocols as previously described in Example 6, Section 3. Isolated PCR products were subjected to low melting point agarose gel testing to confirm pCanf2 positive bands. The results prove that pCanf2 is expressed in eukaryotic cells.

Example 10

Dust Mite Allergenic Protein Antigen Der p1 Genetic Clone and Eukaryotic Expression Assay 1. Der p1 Primer Synthesis The following sequences were used as Der p1 primers. Primers were artificially synthesized:

```
Der p 1 P1 5' primer:              (SEQ ID NO: 45)
AAGCTTAACATGAAAATTGTTTTGG Der p 1 P2 3' primer:              (SEQ ID NO: 46)
GGTACCGTTTAGAGAATGACAACAT
```

2. Der p1 Expression Vector Construction

Der p1 cDNA was used as a template to perform PCR amplification using Der p1 P1 and Der p1 P2 primers to generate copies of the Der p1 gene. The primers are further described below:

(a) Der p1 P1 5'-AAGCTTAACATGAAAATTGGTTTTGG-3' (SEQ ID NO:45) (the $1^{st}$ site-$6^{th}$ site basic group from the 5' terminal end of the primer sequence is the Hind III recognition site, the $10^{th}$ site-12th site is the original initiator code);

(b) Der p1 P2 5'-GGTACCGTTTAGAGAATGACAACAT-3' (SEQ ID NO:46) (the $1^{st}$ site-$6^{th}$ site basic group from the 5' terminal end of the primer sequence is the Kpn I recognition site, the $9^{th}$ site-$11^{th}$ site is the original termination code).

PCR fragments and pVAX1 (Invitrogen, Inc.) were subjected to the digestion, transformation, isolation, and ligation methods as described in Example 7, Section 2. Positive clones were selected and analyzed using sequential analysis discussed in Example 7, Section 2 to obtain the Der p1 expression vector, pDerp1.

3. Der p1 Eukaryotic Expression The pDerp1 expression vector was subjected to transfection, total RNA isolation, and RT-PCR protocols as previously described in Example 6, Section 3. Isolated PCR products were subjected to low melting point agarose gel testing to confirm pDerp1 positive bands. The results prove that pDerp1 is expressed in eukaryotic cells.

Example 11

Peanut Allergenic Protein Antigen Ara h II Genetic Clone and Eukaryotic Expression Assay 1. Ara h II Primer Synthesis The following sequences were used as Ara h II primers. Primers were artificially synthesized:

```
Ara h II P1 5'                    (SEQ ID NO: 47)
primer:
AAGCTTCTCATGCAGAAGAT Ara h II P2 3'                    (SEQ ID NO: 48)
primer:
GGTACCTTAGTAT CTGTCTC
```

2. Ara h II Expression Vector Construction

Ara h II cDNA was used as a template to perform PCR amplification using Ara h II P1 and Ara h II P2 primers to generate copies of the Ara h II gene. The primers are further described below: (a) Ara h II P1 5'-AAGCTTCTCATGCAGAAGAT-3' (SEQ ID NO:47) (the $1^{st}$ site-6th site basic group from the 5' terminal end of the primer sequence is the Hind III recognition site, the $10^{th}$ site-$12^{th}$ site is the original initiator code), Ara h II P2 5'-GGTACCTTAGTATCTGTCTC 3' (SEQ ID NO:48) (the $1^{st}$ site-$6^{th}$ site basic group from the 5' terminal end of the primer sequence is the Kpn I recognition site, the $7^{th}$ site-$9^{th}$ site from the 5' terminal end of the primer sequence is the original termination code).

PCR fragments and pVAX1 (Invitrogen, Inc.) were subjected to the digestion, transformation, isolation, and ligation methods as described in Example 7, Section 2. Positive clones were selected and analyzed using sequential analysis discussed in Example 7, Section 2 to obtain the Ara h II expression vector, pArahII.

3. Ara h II Eukaryotic Expression

The pArahII expression vector was subjected to transfection, total RNA isolation, and RT-PCR protocols as previously described in Example 6, Section 3. Isolated PCR products were subjected to low melting point agarose gel testing to confirm pArahII positive bands. The results prove that pArahII is expressed in eukaryotic cells.

Example 12

Peanut Allergenic Protein Antigen Ara h 5 Genetic Clone and Eukaryotic Expression Assay 1. Ara h 5 Primer Synthesis The following sequences were used as Ara h 5 primers. Primers were artificially synthesized:

```
Ara h 5 P1 5' primer:             (SEQ ID NO: 49)
AAGCTTATGTCGTGGCAAAC

Ara h 5 P2 3' primer:             (SEQ ID NO: 50)
GGTACCTAAAGACCCGTATC
```

2. Ara h 5 Expression Vector Construction

Ara h 5 cDNA was used as a template to perform PCR amplification using Ara 5 P1 and Ara h 5 P2 primers to generate copies of the Ara h 5 gene. The primers are further described below: (a) Ara h 5 P1 5'-AAGCTTATGTCGTGGCAAAC-3' (SEQ ID NO:49) (the $1^{st}$ site-$6^{th}$ site basic group from the 5' terminal end of the primer sequence is the Hind III recognition site; the $7^{th}$ site-$9^{th}$ site is the original initiator code); (b) Ara h 5 P2 5'-GGTACCTAAAGACCCGTATC-3' (SEQ ID NO:50) (the $1^{st}$ site-$6^{th}$ site basic group from the 5' terminal end of the primer sequence is the Kpn I recognition site; the $7^{th}$ site-$9^{th}$ site from the 5' terminal end of the primer sequence is the original termination code).

PCR fragments and pVAX1 (Invitrogen, Inc.) were subjected to the digestion, transformation, isolation, and ligation methods as described in Example 7, Section 2. Positive clones were selected and analyzed using sequential analysis discussed in Example 7, Section 2 to obtain the Ara h 5 expression vector, pArah5.

3. pArah5 Eukaryotic Expression

The pArah5 expression vector was subjected to transfection, total RNA isolation, and RT-PCR protocols as previously described in Example 6, Section 3. Isolated PCR products were subjected to low melting point agarose gel testing to confirm pArah5 positive bands. The results prove that pArah5 is expressed in eukaryotic cells.

Example 13

Japanese Cedar (*Cryptomeria japonica*) Pollen Allergenic Protein Antigen Cry j 1.1 Genetic Clone and Eukaryotic Expression Assay 1. Cry j 1.1 Primer Synthesis The following sequences were used as Cry j 1.1 primers. Primers were artificially synthesized

```
Cry j 1.1 P1 5' primer:           (SEQ ID NO: 51)
AAGCTTATGGATTCCCCTTGCTTAT

Cry j 1.1 P2 3' primer:           (SEQ ID NO: 52)
GGTACCATCAACAACGTTTAGAG
```

2. Cry j 1.1 Expression Vector Construction

Cry j 1.1 cDNA was used as a template to perform PCR amplification using Cry j 1.1 P1 and Cry j 1.1 P2 primers to generate copies of the Cry j 1.1 gene. The primers are further described below:

(a) Cry j 1.1 P1 5'-AAGCTTATGGATTCCCCTTGCTTAT-3' (SEQ ID NO:51) (the $1^{st}$ site-$6^{th}$ site basic group from the 5' terminal end of the primer sequence is the Hind III recognition site; the $7^{th}$ site-$9^{th}$ site is the original initiator code);

(b) Cry j 1.1 P2 5'-GGTACCATCAACAACGTTTAGAG-3' (SEQ ID NO:52) (the $1^{st}$ site-$6^{th}$ site basic group from the 5' terminal end of the primer sequence is the Kpn I recognition site; the $7^{th}$ site-$9^{th}$ site from the 5' terminal end of the primer sequence is the original termination code).

PCR fragments and pVAX1 (Invitrogen, Inc.) were subjected to the digestion, transformation, isolation, and ligation methods as described in Example 7, Section 2. Positive clones were selected and analyzed using sequential analysis discussed in Example 7, Section 2 to obtain the Cry j 1.1 expression vector, pCryj1.1.

3. pCryj1.1 Eukaryotic Expression

The pCryj1.1 expression vector was subjected to transfection, total RNA isolation, and RT-PCR protocols as previously described in Example 6, Section 3. Isolated PCR products were subjected to low melting point agarose gel testing to confirm pCryj1.1 positive bands. The results prove that Cry j 1.1 may be expressed in eukaryotic cells.

Example 14

Japanese Cedar (*Cryptomeria japonica*) Pollen Allergenic Protein Antigen Cry j 1.2 Genetic Clone and Eukaryotic Expression Assay 1. Cry j 1.2 Primer Synthesis The following sequences were used as Cry j 1.2 primers. Primers were artificially synthesized

```
Cry j 1.2 P1 5' primer:         (SEQ ID NO: 53)
AAGCTTATGGATTCCCCTTGCTTAG

Cry j 1.2 P2 3' primer:         (SEQ ID NO: 54)
GGTACCTCAACAACGTTTAGAGAGAG
```

2. Cry j 1.2 Expression Vector Construction

Cry j 1.2 cDNA was used as a template to perform PCR amplification using Cry j 1.2 P1 and Cry j 1.2 P2 primers to generate copies of the Cry j 1.1 gene. The primers are further described below:

(a) Cry j 1.2 P1 AAGCTTATGGATTCCCCTTGCTTAG-3' (SEQ ID NO:53) (the $1^{st}$ site-$6^{th}$ site basic group from the 5' terminal end of the primer sequence is the Hind III recognition site; the $7^{th}$ site-$9^{th}$ site from the 5' terminal end of the primer sequence is the original initiator code);

(b) Cry j 1.2 P2 5'-GGTACCTCAACAACGTTTA-GAGAGAG-3' (SEQ ID NO:54) (the $1^{st}$ site-$6^{th}$ site basic group from the 5' terminal end of the primer sequence is the Kpn I recognition site; the $7^{th}$ site-$9^{th}$ site from the 5' terminal end of the primer sequence is the original termination code).

PCR fragments and pVAX1 (Invitrogen, Inc.) were subjected to the digestion, transformation, isolation, and ligation methods as described in Example 7, Section 2. Positive clones were selected and analyzed using sequential analysis discussed in Example 7, Section 2 to obtain the Cry j 1.2 expression vector, pCryj1.2.

3. pCryj1.2 Eukaryotic Expression

The pCryj1.2 expression vector was subjected to the transfection, total RNA isolation, and RT-PCR protocols previously described in Example 6, Section 3. Isolated PCR products were subjected to low melting point agarose gel testing to confirm pCryj1.2 positive bands. The results prove that Cry j 1.2 may be expressed in eukaryotic cells.

Example 15

*Blomia tropicalis* Allergenic Protein Antigen Blo t 5 Genetic Clone and Eukaryotic Expression Assay 1. Blo t 5 Primer Synthesis The following sequences were used as Blo t 5 primers. Primers were artificially synthesized

```
Blo t 5 P1 5' primer:                (SEQ ID NO: 55)
AAGCTTACAATGAAGTTCGC

Blo t 5 P2 3' primer:                (SEQ ID NO: 56)
GGTACCAATTTTTATTGGGT
```

2. Blo t 5 Expression Vector Construction

Blo t 5 cDNA was used as a template to perform PCR amplification using Blo t 5 P1 and Blo t 5 P2 primers to generate copies of the Blo t 5 gene. The primers are further described below:

(a) Blo t 5 P1 5'-AAGCTTACAATGAAGTTCGC-3' (SEQ ID NO:55) (the $1^{st}$ site-$6^{th}$ site basic group from the 5' terminal end of the primer sequence is the Hind III recognition site; the $10^{th}$-$12^{th}$ site from the 5' terminal end of the primer sequence is the original initiator code);

(b) Blo t 5 P2 5'-GGTACCAATTTTTATTGGGT 3' (SEQ ID NO:56) (the $1^{st}$ site-$6^{th}$ site basic group from the 5' terminal end of the primer sequence is the Kpn I recognition site; the $12^{th}$ site-$14^{th}$ site from the 5' terminal end of the primer sequence is the original termination code).

PCR fragments and pVAX1 (Invitrogen, Inc.) were subjected to the digestion, transformation, isolation, and ligation methods as described in Example 7, Section 2. Positive clones were selected and analyzed using sequential analysis discussed in Example 7, Section 2 to obtain the Blo t 5 expression vector, pBlot5.

3. pBlot5Eukaryotic Expression

The pBlot5expression vector was subjected to transfection, total RNA isolation, and RT-PCR protocols as previously described in Example 6, Section 3. Isolated PCR products were subjected to low melting point agarose gel testing to confirm pBlot5 positive bands. The results prove that pBlot5 may be expressed in eukaryotic cells.

Example 16

Induction of Adaptive T Regulatory Cells that Suppress the Allergic Response: Conversion of T Regulatory Cells by Suboptimal DCs that are Induced by Co-Immunization of DNA and Protein Vaccines Total flea extracts induce immediate intradermal allergic reactions in mice, therefore this system can be used to evaluate immunotherapeutic methods aimed at amelioration of AIH. Using this rodent model of AIH induced by flea allergens, co-immunization of DNA and protein vaccines encoding the flea salivary specific antigen (FSA1) ameliorates experimental AIH, including antigen induced wheel formation, elevated T cell proliferation, infiltration of lymphocytes and mast cells to the site of challenge. The amelioration of AIH was directly related to the induction of a specific population of flea antigenic specific T cells exhibiting a $CD4^+/CD25^-/FoxP3^+$ phenotype, a characteristic of Tr. These Tr also express IL-10, IFN-γ and the transcriptional factor T-bet after antigen stimulation. These Tr are driven by $MHC\text{-}II^+/CD40^{low}$ DC populations that are induced by the co-immunization of DNA and protein vaccines. These studies identify important cellular players in the control of AIH. Exploitation of these cellular regulations and their induction will provide novel direction to develop therapies for allergic and related disorders.

Methods

Histology Analysis.

On day 14 following the last immunization, skin samples from mice were collected and fixed in 4% of paraformaldehyde, embedded in paraffin blocks from every group of mice. Four to five-micrometer sections were cut and placed on sylan-coated glass slides prior to rehydrated in xylene and washed with decreasing concentrations of alcohol solutions. The endogenous peroxidase activity was blocked by 3% hydrogen peroxide at room temperature for 10 min and the antigen retrieval was accomplished by boiling the slides in 0.01 M citrate buffer (pH 6.0). Lastly, slides were stained with hematoxylin and eosin (H&E) or toluidine blue for mast cells and analyzed under a light microscope for histology changes.

Skin Test.

On day 14 after the last immunization, the mice were challenged with 1 μg/μl of flea-saliva-antigen on nonlesional lateral thorax skin intradermally, PBS is used as a negative control and histamine is used as a positive control. The diameter of the skin reaction was measured within 20 min after challenge by using a calibrated micrometer. Reaction was considered as a positive when the injection site was larger than half the size of the sums of diameters injected comparing the positive and negative control challenges.

T Cell Recall Responses.

The T cells isolated from immunized mice on day 14 were cultured at $5\times10^4$ cells/well in triplicate in 96-well plates containing RPMI-10/5% FCS and then stimulated with 20 μg/ml of Flea-saliva-antigen for 48 h. Following the stimulation, cell proliferation was assessed by a colorimetric reaction after the addition of 20 pl of an MTS-PMS (Pormaga, USA) solution for 2-4 hrs and its color density was read at 570 nm by plate reader (Magellan, Tecan Austria GmbH).

Measurement of Flea Antigen-Specific Antibodies.

Serum concentration of anti-flea IgG1, IgG2a, IgG2b, IgM and IgE isotypes were measured using flea antigen coated plates by ELISA and detection with specific horseradish peroxidase-conjugated rat anti-IgG1, IgG2a, IgG2b, IgM and IgE antibodies (SouthernBiotech, Birmingham, USA), absorbance (450 nm) was measured using an ELISA plate reader (Magellan, Tecan Austria GmbH).

RT-PCR.

Total RNA was isolated from spleen and skin tissue 14 d after immunization using TRIzol reagent (Promega). cDNA was synthesized and PCR was performed in a 50 pl reaction mixture with 5 μl cDNA and 1.0 μM of each of the following primers: HPRT, IL-2, IFN-γ, IL-4, IL-5, IL-13, IL-10 and IL-12(38). For Gata3 and T-bet analysis, $CD4^+CD25^-$ T cells were isolated and total RNA was prepared. RT-PCR was done as described using specific primer sequences as follows for Gata3,5'-GGAGGCATCCAGACCCGAAAC-3' (forward) (SEQ ID NO: 57) and 5'-ACCATGGCGGTGACC-ATGC-3' (reverse) (SEQ ID NO: 58); for T-bet, 5'-TGAAGCCCA-CACTCCTACCC-3' (forward) (SEQ ID NO: 59); and 5'-GCGGCATTTTCTCAGTTGGG-3' (reverse) (SEQ ID NO: 60).

Isolation of $CD4^+CD25^-$ T Cells and Adoptive Transfer.

Single splenocyte suspensions were prepared from mouse spleen and $CD4^+CD25^-$ T cells were isolated and purified by using the MagCellect Mouse $CD4^+CD25^+$ Regulatory T Cell Isolation Kit according to the manufacturer's protocol (R&D Systems, Inc., USA). The purity of the selected cell populations was 96-98%. The purified cells ($1\times10^6$ per mouse) were adoptively transferred intravenously into C571BL6 mice.

CFSE Labeling and Co-Culture of Cells.

Naive $CD4^+$ T cells isolated from C57/BL6 mice were labeled with CFSE (Molecular Probes). For assay of regulatory activity, 1×104 pcDF100+F induced regulatory or control T cells were co-cultured with 4×104 purified and CFSE labeled naive $CD4^+$ T cells in the presence of flea antigen (100 μg/ml) and 1×104 bone marrow derived DCs. For some cultures, Tr cells were co-cultured with anti-IL-10, anti-IFN-γ or an isotype control antibody at 100 g/ml. After 72 h, cells were collected and labeled then CFSE+ cells were selected for analysis by flow cytometry.

Flow Cytometry.

$CD4^+CD25^-$ T cells were isolated and incubated on ice with PE-conjugated antibodies to CD44, CD69, CD62L (eBioscience, CA, USA). Flow cytometry of cytokine production and FoxP3 expression in T cells were performed, single cell suspensions were prepared from the animals spleens and Fc receptors were blocked with excess anti-Fc (BD PharMingen, USA). Cells were washed with ice-cold PBS. For intracellular cytokine staining, T cells were stimulated overnight with Con A (Sigma-Aldrich) in the presence of anti-CD28 mAb (BD PharMingen, USA). Collected cells were fixed with 4% paraformaldehyde and permeabilized with 0.1% saponin (Sigma-Aldrich). For staining of surface of CD4 or cytoplasmic IL-10, IL-4, IFN-γ or FoxP3, the appropriate concentrations of phycoerythrin-labeled antibodies (eBioscience, CA, USA) were added to premeabilized cells for 30 min on ice followed by washing twice with cold PBS. Samples were processed and screened using FACSCalibur and data were analyzed with Cell Questpro software (BD).

Results

Figure 1B:
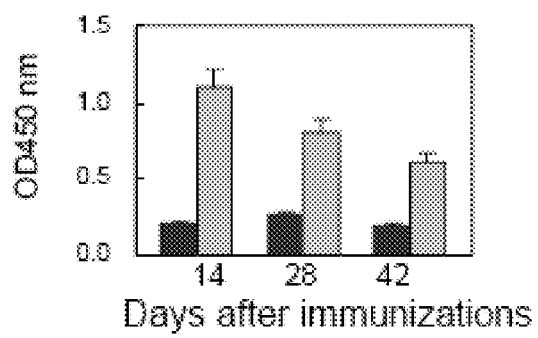
Figure 1C:
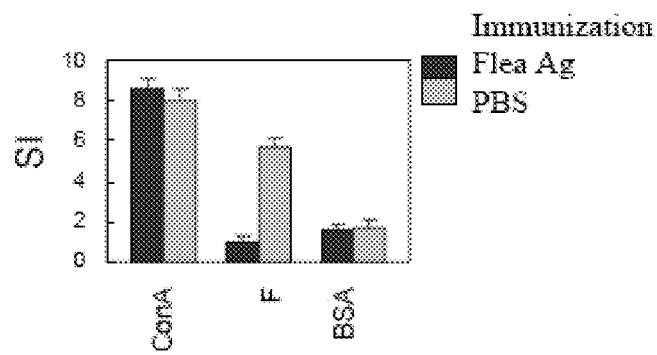

A flea salivary allergen, FSA1, has been identified and implicated as one of the causes for allergy dermatitis observed in cats and dogs. The degree of skin reaction or intradermal test (IDT) to assess the immediate intradermal flea-antigen reactivity can be achieved by flea allergy challenge intradermally. As expected, administration of mice with flea antigen induced significant skin reactions (FIG. 1a), induced mast cells activation, induced coincident IgE production (FIG. 1b), and induced strong CD4+ T cell proliferation responses (FIG. 1c) in C57 mice when compared with naive control animals after intradermal challenge. This data demonstrates the utility of the flea antigen allergic model for evaluation of novel therapeutic strategies against AIH.

Figure 2A:
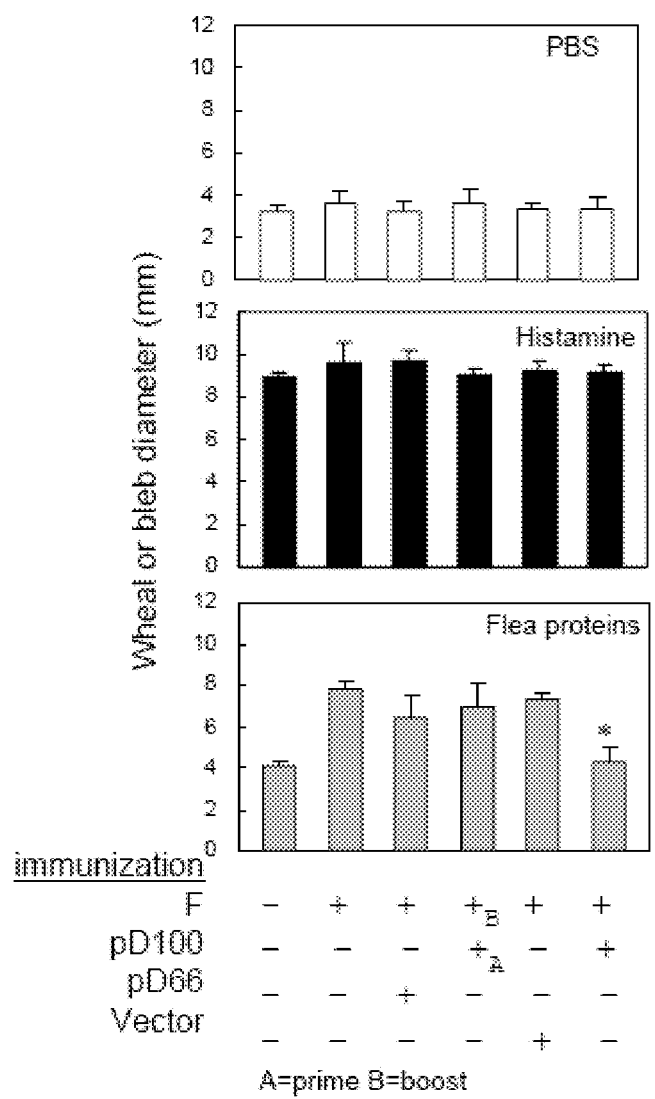
FIGS. 2a-2d show that co-immunization of DNA and protein suppresses the development of immediate hyper-sensitivity reaction.

This model was used to examine the ability of the co-inoculation strategy to protect animals from the immediate hypersensitivity after flea allergen challenge. C57/BL6 mice were pre-sensitized with various test vaccines and animals were intradermal challenged with the flea extracts, or with histamine as the positive or using PBS as the negative control. The immediate hypersensitivity reaction was blocked in group immunized 14 days earlier of co-inoculation of a plasmid DNA, pcDF100, encoding an epitope of FSA1 (aa100-114) mixed with the total flea proteins (designated as pcDF100+F) (FIG. 2a). To determine if the inhibition observed was due to the plasmid backbone or rather was related to a DNA construct encoding another region of FSA 1. Robust inflammation of the challenged sites were observed in the mice immunized with either vector control plus flea proteins (designated as V+F), or a DNA construct encoding another region of FSA1 at aa66-80, pD66, again mixed with the flea proteins (designated as pcDF66+F, FIG. 2a). We also examined the influence of host immune balance toward Th1 type on the inhibition of allergic reaction, the pcDF100 primed and the flea protein boosted animals (designated as pcDF100→F; FIG. 2a). The severe reaction following challenge was observed in mice primed with pcDF 100 and boosted with F (FIG. 2a), suggesting that induction of a strong immune response worsens the allergic reaction.

Histological analysis revealed infiltrations by leukocytes and mast cells in the skin lesions of mice immunized with F or V+F at the challenge sites; whereas, mice immunized with pcDF100+F showed normal intradermal structure which was free of inflammatory cells.

Figure 2B:
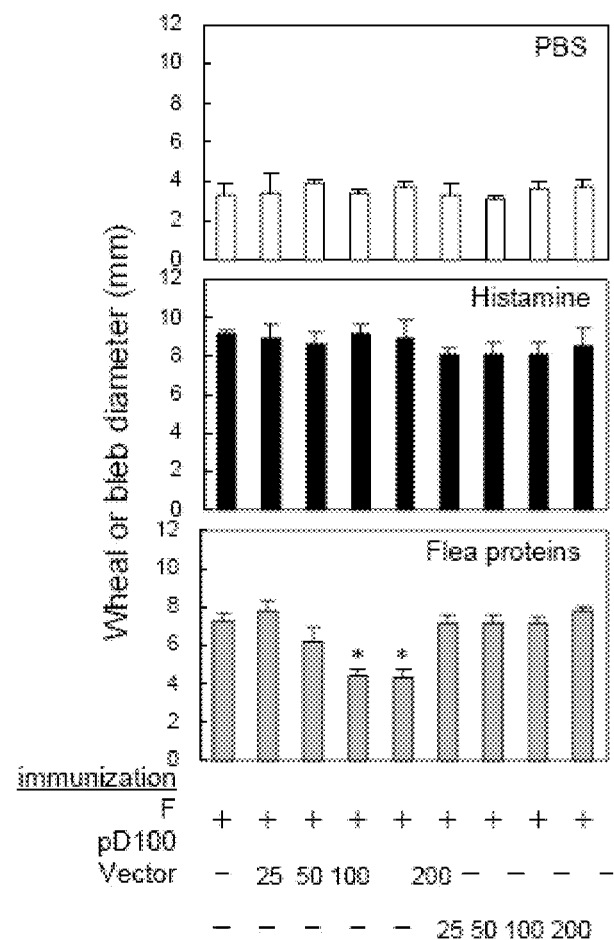

We next analyzed if the blocking of the immune reaction induced by the co-inoculation was a dose dependent. pcDF100 at dose of 25, 50, 100 and 200 μg was co-immunized with 100 μg of flea proteins, respectively. Dosage at 50 μg of pcDF 100 showed significant inhibition of the intradermal reaction which reached maximal inhibition at 100 μg. A dosage of 25 μg exhibited only a minimal effect on lesion formation, as the animals developed severe reactions similar to those observed in animals inoculated with either F or V+F (FIG. 2b) or positive controls.

High levels of IL-4, IL-5 and IL-13 are the characteristics of allergic reactions and these immune modulators are implicated in allergy severity. Different profiles of the cytokines associated with the co-inoculated regimens were examined. Mice co-inoculated with F or V+F produced higher level of mRNA expressions for IL-4, IL-5 and IL-13; whereas, mice co-immunized with pcDF100+F produced relative low levels of these cytokines, suggesting that an anti-inflammatory immune regulatory function was derived from the co-inoculation of pcDF100+F. No significant differences were found in the levels of IL-2 or IFN-γ among the co-inoculated regimens, but IFN-γ was slightly higher in mice primed with pcDF100 and boosted by F. This result again suggests that the induced inhibition of the allergic reaction by co-immunization is not due to an un-balanced Th2 to Th1 response by the allergenic-specific T-helper cells.

Figure 2C:
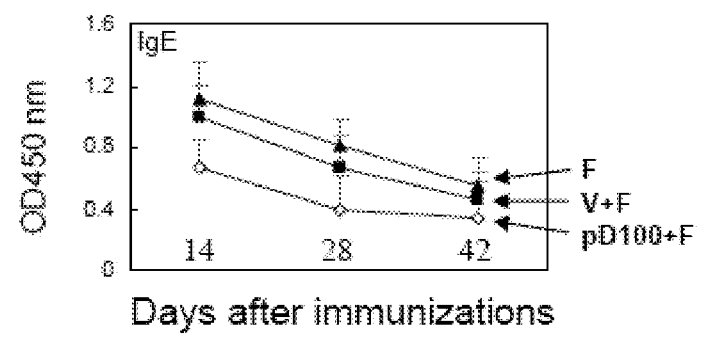
Figure 2C:
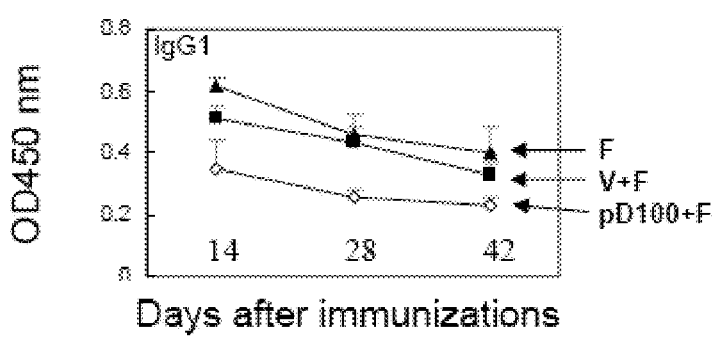

As flea antigen triggered IgE-mediated allergy is well characterized, the ability of co-inoculation of pcDF100+F to inhibit anti-flea induced IgE production was examined. The levels of anti-flea IgE and IgG in sera were measured on days 14, 28 and 42 and were reduced slightly in mice co-immunized with pcDF100+F compared with groups immunized with V+F or F alone (FIG. 2c), suggesting that the co-inoculation does not influence the IgE production.

Figure 2D:
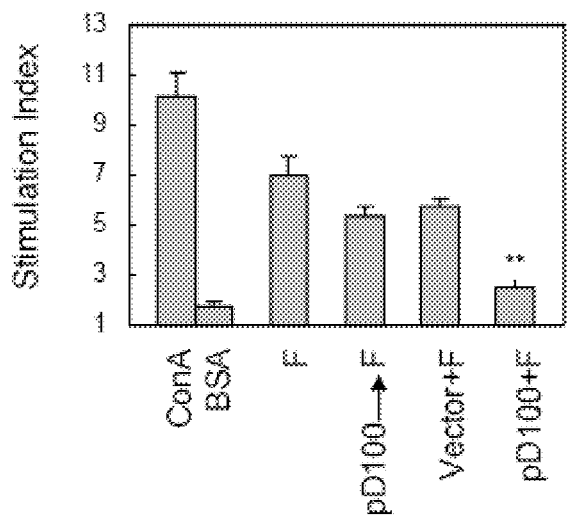

Proliferative $CD4^+$ T cells are known to be involved in the development of immediate hypersensitivity. I isolated $CD4^+$ T cells from the spleen of mice co-immunized with F, V+F or pcDF100+F was examined on day 14 after the second immunization for their recall proliferative responses to flea antigens in vitro. Immunizations of F and V+F resulted in strong proliferation of $CD4^+$ T cells; whereas the $CD4^+$ T cells isolated from pcDF100+F immunized mice showed little, if any, proliferation in response to the flea antigen stimulation (FIG. 2d). These results suggest that the inhibition of hypersensitivity observed by co-immunization of pcDF100+F is related to the non-responsive antigen specific $CD4^+$ T cells.

The results indicate that the co-immunization with pcDF100 and flea proteins antigen induces an inhibition of the allergic reaction via down-regulating the levels of inflammatory cytokines and $CD4^+$ cells induced by flea intradermal challenge. This suggests that the prevention of allergy is likely antigen specific since the antigen mismatched combinations did not produce the same effect.

Figure 3A:
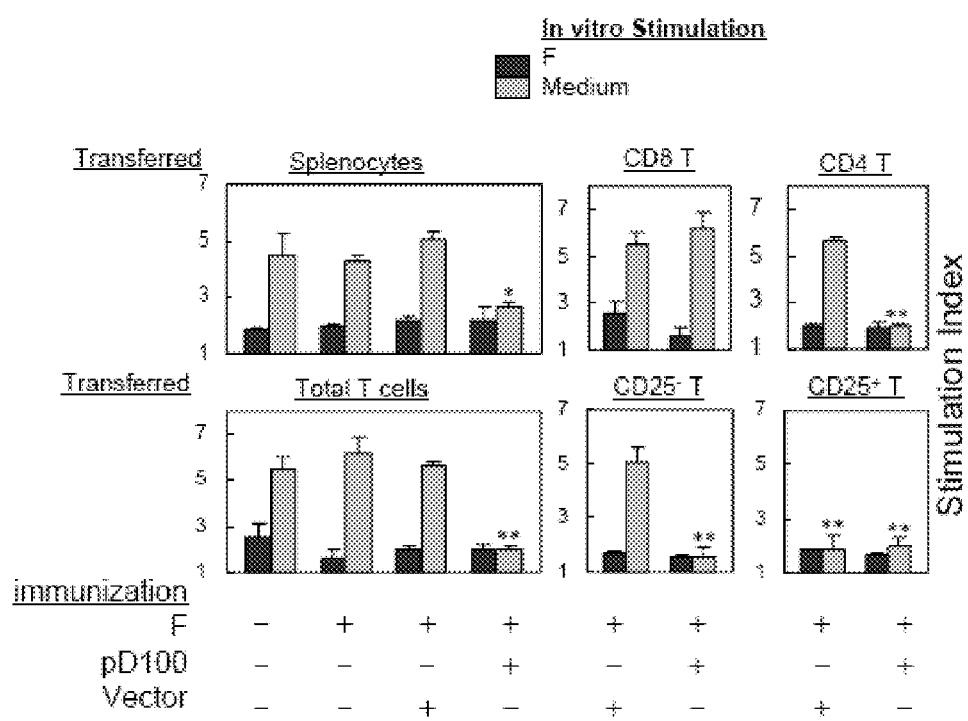
FIGS. 3a-3c show that $CD4^+CD25^-$ T cells are responsible for the observed suppression.

To test if antigen-specific Tr cells have been induced by the co-immunization of flea DNA and protein vaccines, splenocytes were collected from co-immunized C57B/6 mice and mixed with the flea-antigen-specific effector T cells of syngeneic mice to exam their ability to inhibit recall proliferative responses in vitro. As shown in FIG. 3a, splenocytes from mice co-immunized with pcDF100+F significantly inhibited T cell recall immune responses. In contrast, splenocytes from mice immunized with F or V+F as well as from naive mice failed to inhibit the antigen specific T cell proliferative responses (FIG. 3a). This indicates that cells within the splenocyte population likely generated during the co-immunization of animals can suppress this antigen specific T cell proliferation. Purified non-T cells, T cells or subsets of T cells from the spleen of mice co-immunized with pcDF100+F were identified and tested individually for suppression of recall proliferation. Significant inhibition was observed from reactions of either purified T cells, purified $CD4^{4+}$ cells, or purified $CD4^+CD25"$ cells from the mice co-immunized with pcDF100+F, but not from other subsets of cells (FIG. 3a). However, the inhibitions from $CD4^+CD25^+$ cells are in general thought to be independent of antigen sensitization, whereas the inhibition of $CD4^+CD25"$ cells of this reaction is in an antigen dependent manner (FIG. 3a).

Figure 3B:
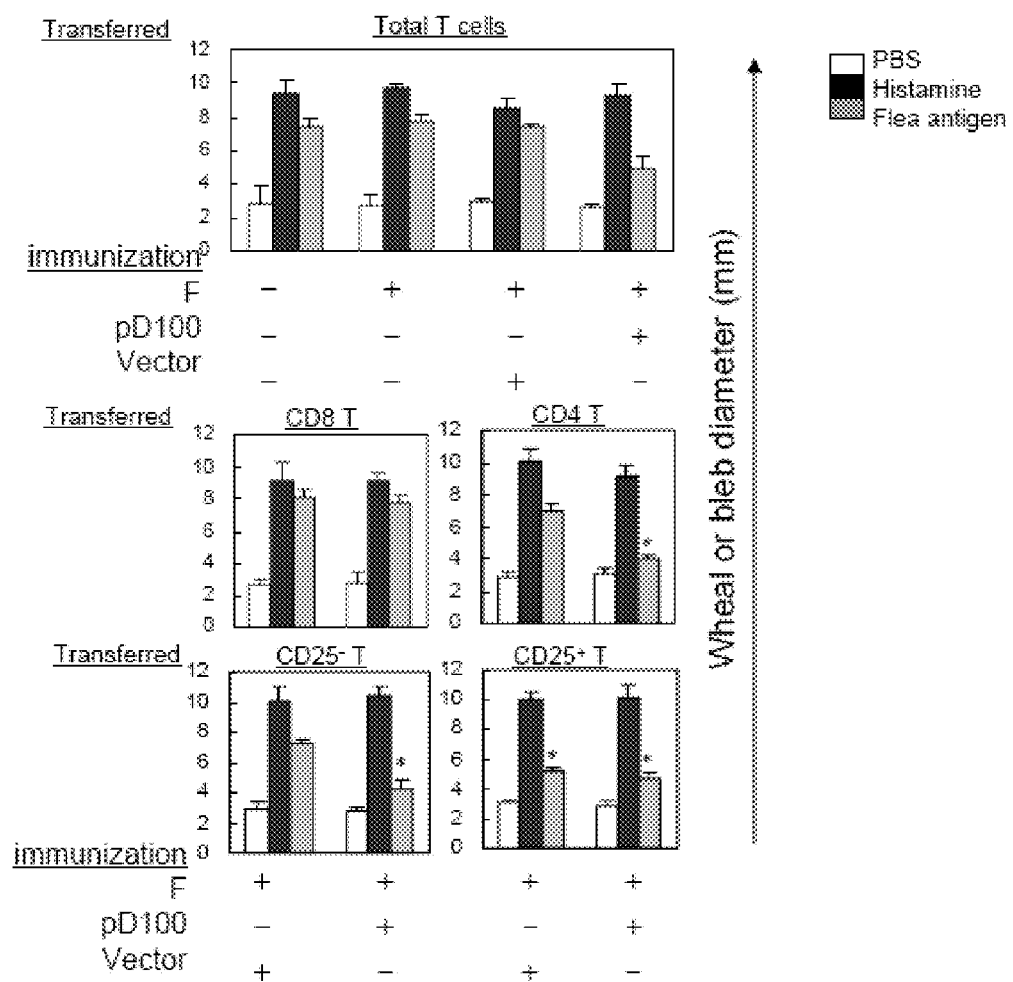

To further examine this issue in vivo, adoptive transfer was utilized. Antigen naive syngeneic recipient mice were adoptively transferred with either total splenocytes, T, $CD4^{4+}$ or $CD8^+$ cells isolated from C57B/6 mice co-immunized with pcDF100+F, F or V+F, respectively. All recipient mice were next challenged intradermally by flea extract to induce the hypersensitivity. Splenocytes, T and $CD4^+$ T cells from mice immunized with the pcDF100+F, but not with the F or V+F, were all able to suppress the development of the immediate hypersensitivity reaction (FIG. 3b). In contrast, $CD8^+$ T cells isolated from all three experimental groups and naive control mice did not suppress this reaction. Both in vitro and in vivo results indicate that $CD4^+CD25^-$ Tr cells can mediate this suppression.

Figure 3C:
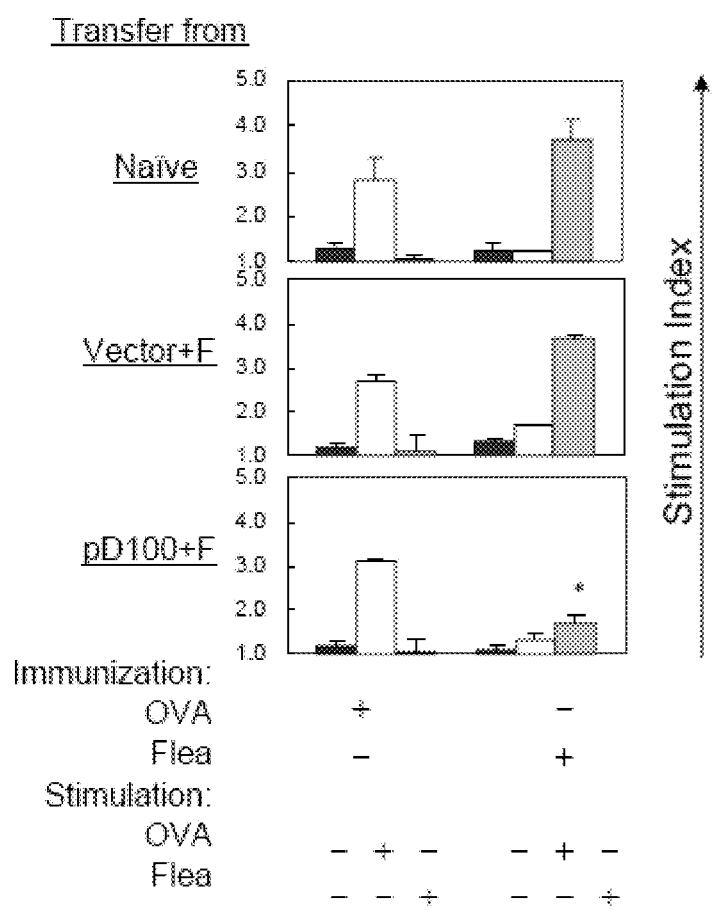

To investigate the observed role, of $CD4^+CD25^-$ Tr antigen specificity, the $CD4^+C25^-$ Tr cells taken from C57B/6 mice co-immunized with pcDF100+F were adoptively transferred into the syngeneic recipient mice that were subsequently immunized twice at a biweekly interval with flea-antigen or OVA in Freunds' complete adjuvant (FCA). On day 14 after the last immunization, T cells were isolated and tested for their ability to proliferate to either flea antigen or OVA in vitro. T cells from recipient mice immunized with flea antigen did not respond the flea antigen stimulation in vitro; whereas, the T cells from recipient mice immunized with OVA-FCA responded well with OVA stimulation, but not to the flea antigens stimulation in vitro. As the controls, the naive mice immunized with flea antigen respond well to the flea antigen stimulation, but not to OVA stimulation in vitro and vice versa (FIG. 3c). This result indicates that adoptive transferred $CD4^+C25^-$ Tr cells only inhibit the flea antigen specific T cell priming and proliferation in vivo; while the responses from the irrelevant antigen specific T cells were not affected.

Taken together, these data demonstrate that $CD4^+CD25^-$ Tr cells were induced by the co-immunization of DNA and protein vaccines. These appear to be unique CD4+ Tr cells as they function in an antigen-specific manner.

To determine if Tr cells induced by co-inoculation express certain types of cytokines and unique markers associated with Tr cells as previously documented (J. D. Fontenot, M. A. Gavin, A.Y. Rudensky, *Nat Immunol* 4, 330 (Apr. 1, 2003); M. G. Roncarolo, R. Bacchetta, C. Bordignon, S, Narula, M. K. Levings, *Immunol Rev* 182, 68 (Aug. 1, 2001); and P. Stock et al., *Nat Immunol* 5, 1149 (Nov. 1, 2004)), $CD4^4CD25^-$ cells were isolated from the mice immunized with F, V+F or pcDF100+F on days 1, 3, 7 and 14 post immunization and T cell profiles were followed by intracellular staining with specific fluorescent labeled antibodies. After co-immunization, on days 1, 3, 7 and 14, $CD4^+CD25^-$ T cells were isolated from F, V+F and pcDF100+F immunized mice and intracellular cytokine production for IL-10, IFN-γ and IL-4 expression was assessed by flow cytometry. $CD4^+CD25^-$ Tr cells isolated from F, V+F, pcDF100+F and naive mice as controls were analyzed for expression of CD69, CD44 and CD62L, and for their expression of FoxP3. Tr cells express T-bet but not gata-3. On day 14 after immunization, total RNA was extracted from $CD4^+CD25^-$ T cells from all three groups and RT-PCR was used to test the expression of HPRT, T-bet and gata-3. Over the course of 14 days, the $CD4^+CD25"$ T cells isolated from mice co-immunized with pcDF100+F expressed high levels of IL-10, IFN-γ, FoxP3, and a minimal amount of IL-4. In contrast, CD4$^+$CD25" T cells produced a higher level of IL-4 and no expressions of FoxP3, IL-10, or IFN-γ from the mice immunized with F or V+F. Since the transcriptional factor Foxp3, has been demonstrated to be a hallmark of the Tr cells, the co-vaccination induced CD4$^+$CD25$^-$ Tr cells can be categorized into the regulatory class of T cells but they have a unique phenotype. T cell activation markers are expressed equally high including CD44 and CD69 and low for CD62L among the immunized groups, suggesting that the induced CD4$^+$CD25$^-$ Tr cells are fully activated by the immunization.

To analyze the Th phenotype for the induced CD4$^+$CD25$^-$ Tr cells based on the observed cytokine expression patterns as described above, the expression of both T-bet and gata-3 genes of the CD4$^+$CD25$^-$ T cells from mice immunized with F, V+F or pcDF100+F were analyzed by the RT-PCR method. The results show that the CD4$^+$CD25$^-$ T cells from the pcDF100+F immunized mice, but not from the F or V+F immunized mice, expressed higher level of T-bet, a hallmark for Th1 cells. In the contrast, the CD4$^+$CD25$^-$ T cells from the F and V+F immunized mice expressed higher levels of gata-3, a characteristic Th2 cells.

Collectively, these data demonstrate that CD4$^+$CD25$^-$ T cell induced by the co-immunization of DNA and protein vaccines has as an adaptive Th1 phenotypic Tr cell which can suppress the antigen-specific CD4$^+$ T cell proliferative function.

Figure 4A:
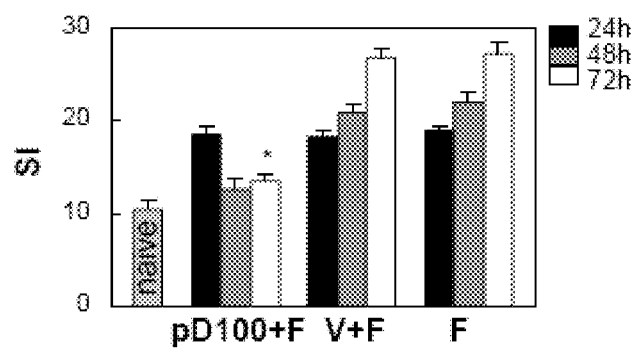
FIGS. 4a-4c show that DCs from pcDF100+F co-immunized mice induce Tr cells in vitro.
Figure 4C:
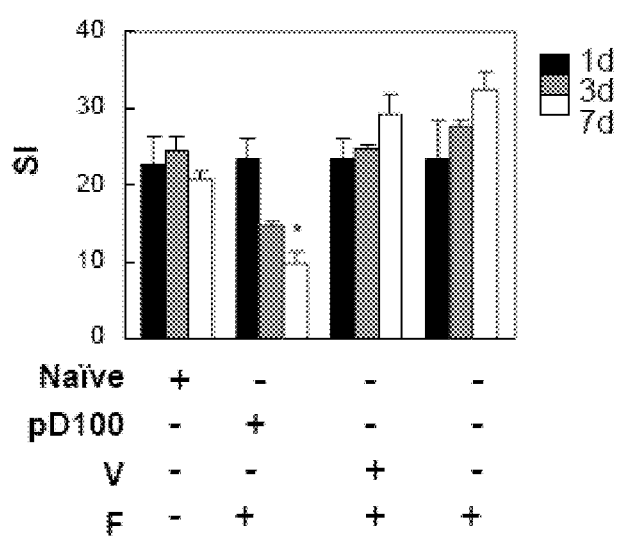
Figure 4B:
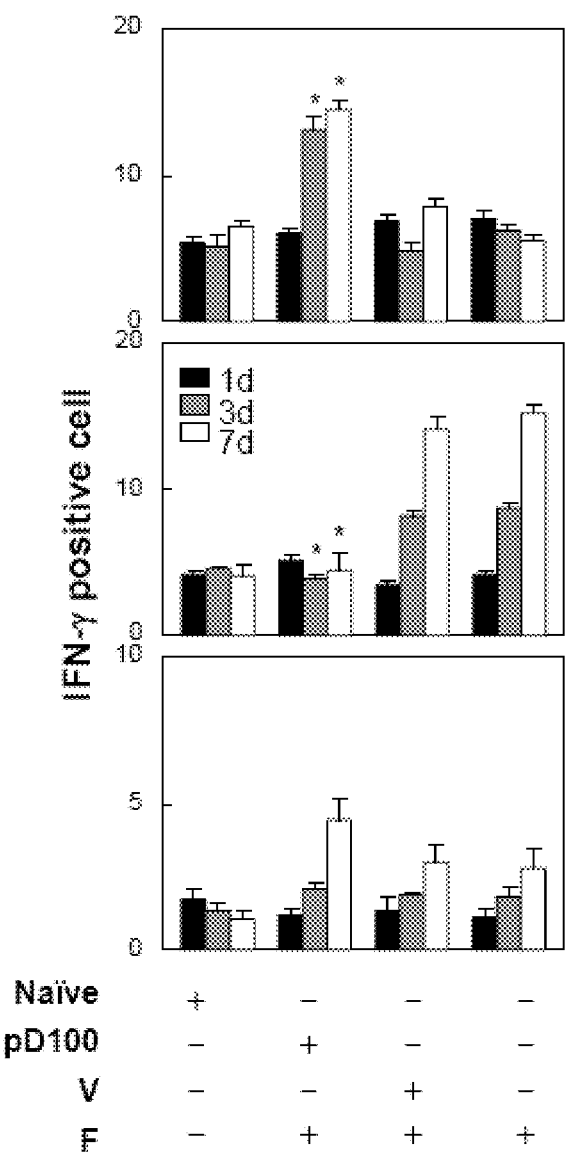

Since antigen presenting cell (APC) activates T cells to promote adaptive immunity, the induction of CD4$^+$CD25$^-$ Tr cell is apparently through specific APC activation by the co-inoculation of DNA+protein vaccines. To investigate this question, a similar experiments described as above was set up to assess dendritic cell (DC) function and phenotype and their influence on naive T cells. The effects of co-inoculation on the maturation of DC was analyzed. Expression of costimulatory molecules on DCs from co-immunized mice was examined. Splenocytes were isolated and stained for expression of surface markers on DCs by gating on CD11 positive cells 48 h after co-immunization of pcDF100+F, V+F or F. Co-immunization of pcDF100+F did not affect maturation of DCs as DCs isolated from the spleen 48 h after the co-immunization expressed high and similar levels of CD80, CD86, MHC II, IL-12, IL-6, IL-1a/f3, IFN-a/8 and TNF-a which are the characteristics of matured DCs; whereas these molecules on the immature DCs from naive control mice remain expressed at relatively low levels, suggesting the co-inoculation enables the immature DC be induced to mature. However, we observed that the level of CD40 expression was dramatically reduced in pcDF100+F co-immunized mice compared to all other groups, suggesting a unique phenotype of DC may be involved in the induction of the observed Tr. DCs from mice immunized with V+F or F were observed to have the ability to activate heterogeneous T cells to proliferate; whereas the Immature DCs of naive mice have no such ability as expected (FIG. 4a). Interestingly, DCs from mice co-immunized with pcDF 100+F had a restricted capacity to activate T cells to proliferate (FIG. 4b), suggesting that an alternative mechanism of Tr induction is induced in the co-immunization group. To explore if the DC of co-immunized mice are able to convert naive T cells to a Tr phenotype, DCs obtained from mice after their being co-immunized with pcDF100+F were co-cultured with syngeneic naive CD4$^+$ T cells in vitro and subsequently characterized the resulting CD4$^+$ T cells by FACS. These T cells upregulated higher levels of CD44, and CD69, but lower levels of CD62L, suggesting that the DC again has the capacity to activate T cells. Similar results were obtained from analysis of DCs from V+F or F co-immunized mice. Furthermore, the activated CD4$^+$ T cells in the pcDF100+F group produced significant higher level of IL-10 and IFN-γ, but reduced IL-4 (FIG. 4b). However, activated T cells from V+F or F immunized groups produce significant level of IL-4, but little IL-10 and IFN-γ (FIG. 4b). The cytokine production were analyzed after three rounds of re-stimulation with fresh DCs isolated from the D+F immunized mice. These studies demonstrated an increase in the production of IL-10 in T-cells, which is one of characteristic of regulatory T cells. To further characterize their regulatory function, IL-10$^+$ T cells were isolated after DC stimulation and subjected to MLR to see if they block responder T cell proliferation in the MLR. As shown, the proliferation of responder T cells were inhibited by the presence of IL-10$^+$ T cells, but not from T cells isolated from co-culture with DCs of mice immunized with V+F and F, or the control animals (FIG. 4c). These data demonstrate that DCs from the D+F co-immunized mice develop large populations of T regulatory cells in vitro.

To demonstrate the same conversion in vivo, DCs collected from BALB/c mice after co-immunization with pcDF100+F were co-transferred with syngenic naive CD4$^+$ T cells into nude mice (nu/nu) and subsequently analyzed these transferred T cells by FACS for intracellular staining for IL-10 and T reg markers. DCs from pcDF100+F co-immunized mice induced Tr cells in vivo. DCs isolated from spleens of pcDF100+F, V+F, F immunized or naive control mice were co-adoptive-transfer with naive CD4$^+$CD25$^-$ T cells. The T cells were analyzed for IL-10, IFN-γ, IL-4, FoxP3 and CD25 on day 3 and 7. Co-transferred T cells expressed more IL-10, FoxP3 and IFN-γ, but little IL-4. However, co-transferred T cells with DCs from V+F or F immunized mice expressed higher levels of IL-4, but little IL-10 and IFN-γ, supporting the in vitro data. Specific IL-10 cytokine production was elevated after two rounds of re-stimulation with the DCs freshly isolated from D+F immunized mice. These data demonstrate that DCs from D+F co-immunized mice drive likely naive T cells into Tr cells in vivo. Consistent with previous results, such conversion was only made within the CD4$^+$CD25" population since the frequency of CD25$^+$ was not observed to be influenced testing vivo.

Finally, experiments were performed to identify what molecules in the interaction between DC and T cells play a role in the development of Tr. Since the Tr is within the activated T cell compartment as demonstrated above, the signals should include classic activation pathway signals. Important among these is the up-regulation of major histocompatibility complex (MHC) class II and co-stimulatory molecules (CD80/CD86), which provide the two requisite signals for naive T cell activation. To study this issue, DCs were isolated from spleen of mice 48 h after pcDF100+F co-immunization and co-cultured with naive CD4$^+$ T cells from naive syngeneic mice in the presence or absence of reagents to block signaling molecules including anti-CD80, anti-CD86, anti-CD40 and anti-After seven days of re-stimulation, T cells were isolated and added into MLR system to examine their regulatory functions. The results showed that both anti-CD40 and anti-MHC II mAbs can partially reverse the suppressive effects on MLR by the Tr cells; whereas mAbs against CD80, CD86 and had no ability to block the induction of the suppression phenotype. These results demonstrate that both CD40 and MHC II signals play roles in the induction of Tr in the flea allergen Induced immediate hypersensitivity model.

Adaptive Tr1 cells have been observed and induced by DCs processing a suboptimal immunogen or subimmunogen to inhibit normal T cells' function mediated via secretion of IL-10 or TGF-b or both. It has been further demonstrated that immature DCs drive the differentiation of IL-10-producing Tr1 cells with producing IL-10, TGF-R, and IFN-γ, but they do not produce IL-4 or IL-2, they are hyporesponsive to antigenspecific and polyclonal activation. In additional evidence has shown that suboptimal activation of DC by a minute antigen stimulation can induces the Tr1 conversion. This stimulation of DCs lacks the co-stimulation signaling and thus presents a tolerance signal to T cells.

Co-inoculation of DNA encoding a flea antigen with flea protein induces adaptive Tr cells which inhibit the allergic reaction induced by flea allergen challenge. The cells exhibit a phenotype of $CD4^+CD25''Foxp3^+$ and suppress in vivo and in vitro antigen specific as well as MLR immune responses through the production of IL-10 and IFN-γ. $MHC-11^+/CD40^{low}$ DC populations are induced by such co-immunization and in turn to convert naive T cells into Tr cells.

Example 17

Testing the Prevention and/or Therapeutic Approaches Against FAD Allergen Through Co-Immunization with Vaccines in a Feline FAD Model Establishing the Feline Model and Testing Co-Immunization There are more than 15 kinds of allergen in the flea saliva. Among them, an 18 kDa protein, flea saliva antigen 1 (FSA1), has been determined a main allergen which can cause FAD. This gene has been cloned and expressed it in the *E. coli* system. In addition, the pVAX-FSA1 eukaryotic expressing construct has also been prepared.

A cat FAD model was established and subsequently used to demonstrate that the therapeutic effect of co-immunization of FSA1+pVAX-FSA1 on the established FAD in cats.
Determination of Number of Fleas, Duration of a Cycle Animal and Parasite Ten pathogen-free cats were purchased from North China Pharmaceutical Group (Shijiazhuang, Hebei) and housed animal facility at the Center for Disease Control and Prevention of China (CDC) in the course of experiment. All cats were over one year old, which is an important factor since the younger animals may be tolerable to the flea allergen in this experiment. The cats were grouped with breed and sex randomly. The sterile fleas were supplied by the CDC.

To determine relationship of infestation and FAD symptom, 10 cats were separated into three groups, including an experimental group with six cats and two control groups with two cats each. One control group was treated nitenpyram, and another was not treated with the nitenpyram. Each experimental cat was lived separated on day 0 and infestated with 100 fleas. After two days, all cats in this group were given the nitenpyram to remove the flea from their bodies. Two of the control cats were also given this medicine on day 0. This challenge cycle was repeated every other week for 7 times
Immunization Scheme for the FAD Induced or Control Cats with FSA1 and pVAX-FSA1 as Co-Immunogens The 6 FAD cats were separated into three groups. Two of them were co-immunized with 400 µg FSA1 i.p. and 400 µg pVAX-FSA1 plasmid at double lateral abdomen subcutaneously. Two were co-immunized with 400 µg FSA 1 i.p. and 400 µg pVAX vector subcutaneously. The last two were not immunized and used as the positive control group. The 4 un-FAD cats were separated into two groups. Two were co-immunized with 400 µg FSA1 i.p. and 400 µg pVAX-FSA1 plasmid at double lateral abdomen subcutaneously and the other two were immunized with 400 µg FSA1 i.p. and 400 µg pVAX vector subcutaneously. The two control cats with nitenpyram were sent into different groups. The cats were immunized three times: at days 0, 9, and 16. After that, the cats were challenged for six cycles as above. During the second immunization, a cycle of challenge was done at the same time, because we wanted to keep positive cats at the susceptible state for next therapy. The program of immunization was as Table 2.

TABLE 2

|  | | Immunization | | |
| --- | --- | --- | --- | --- |
|  | Cat No. | PSA1 + pVAX-FSA1 | PSA1 + pVAX vector | Treat with nitenpyram |
| prophylactive | 1 | − | + | + |
|  | 2 | + | − | − |
|  | 4 | + | − | + |
|  | 5 | − | + | − |
| therapeutic | 8 | + | − | + |
|  | 9 | − | + | + |
|  | 10 | − | + | + |
|  | 11 | + | − | + |
| Positive control | 3 | − | − | + |
|  | 7 | − | − | + |

Dermatological Scores.
Method:

Cats were scored by the dermatological assessments two days after ceasing each infestation. The assessments were included erythema, papules, crusts, scale, alopecia, excoriation. The body of each cat was divided into three portions to assess which part might have the most severe clinical outcome. According the previous documented report, three parts were consisted of: (1) back, from the head to the tail of dorsal surface; (2) double lateral abdomen, from the scapula to the tail; (3) chest and underside, from laryngeal to the caudomedial thighs.
Smearing Counts of Peripheral Blood Cells from the Cats
Method:

The anti-coagulant peripheral blood at 2 ml was collected on days 0, 2, 16, 30, 44, 58, 62 from the experimental group and day 0, 14, 28, 42, 56, 60 from the control groups. The same samples were collected after the immunization. A drop of blood was smeared on a clean glass slide. After the smear was dried, the cells were stained with Wright-Giemsa stain for 15 min. After a rinse in deionized water, the smear was gently dried with Kimwipe paper and dehydrated by 96% and 100% ethanol with each 10 seconds treatment. The slide was then treated with xylene for 30 min.

After the staining, nucleus and cytoplasm of blood cell was distinguished by a blue and pink staining. The percentage of each type of cells was counted by a total number of 200 cells in a view under a light microscope.
Therapeutic Approaches:

The same methods as above were used except that total RNA was extracted from mononuclear cells which were isolated from peripheral blood on day 7 post the third immunization from each group.
Statistical Analysis Analysis of variance (ANOVA) was used to detect the differences which included dermatology scores from each cycle, scores of various lesions and scores on different sites among three groups. The differences of skin test and IgE level were determined also by ANOVA. Statistical analyses of other ones were performed using the Student's t-test. In these analyses, data were converted into logarithmic plot. If the $P<0.05$, indicates a significant difference.

Statistical analyses of were also performed using the Student's t-test. In these analyses, the data was converted into log. If the P<0.05, the data indicated significant differences.
Results:
Observation and Dermatological Scores of the Cats Lesions were scored according to their types, locations, sizes and numbers.

The total scores were analyzed from the groups, and the lesions and sites for the experimental group were assessed. The FAD group registered more scores than in other groups. The scores were increased at the fourth infestation cycle, and then stayed at the level of 5.0. The scores in the FAD group were significant higher than in other control groups (P<0.01). These results support the conclusion that the cat FAD model was valid and feasible to evaluate a therapeutic or prophylactic treatment against the allergic reaction.

To assess where the lesions occur most, what type, and when to occur, statistic analysis was done and it was found that papules and fur loss were the most common factors to contribute to the dermatology scores in FAD group. The reading of erythema was not a contributing factor since the erythema reached to the peak on day 44, but it fallen at the end of this experiment, indicating no persistency. On the other hand, the papules were increased, and remained at a high level after 44 days and reached to the peak on the day 86 (P<0.05), suggesting its persistency. Similarly, fur loss was maintained at high level after day 44 (P<0.05). These two readouts are indicated as a good onset to reflect FAD. The scores from other lesions were randomly distributed and inconsistent in the two control groups, in which no significant difference of lesions were observed.

Although, most of dermal lesions tended to be located on the backs and heads compared other sites on day 44 (P<0.05), the lesions were extended all over the body at the end of the experiment. This observation was different from the previous reports in dog, of which the chest and underside were tended to have the most lesions. That may owe to the habitual differences of the cats and dogs.

Figure 5A:
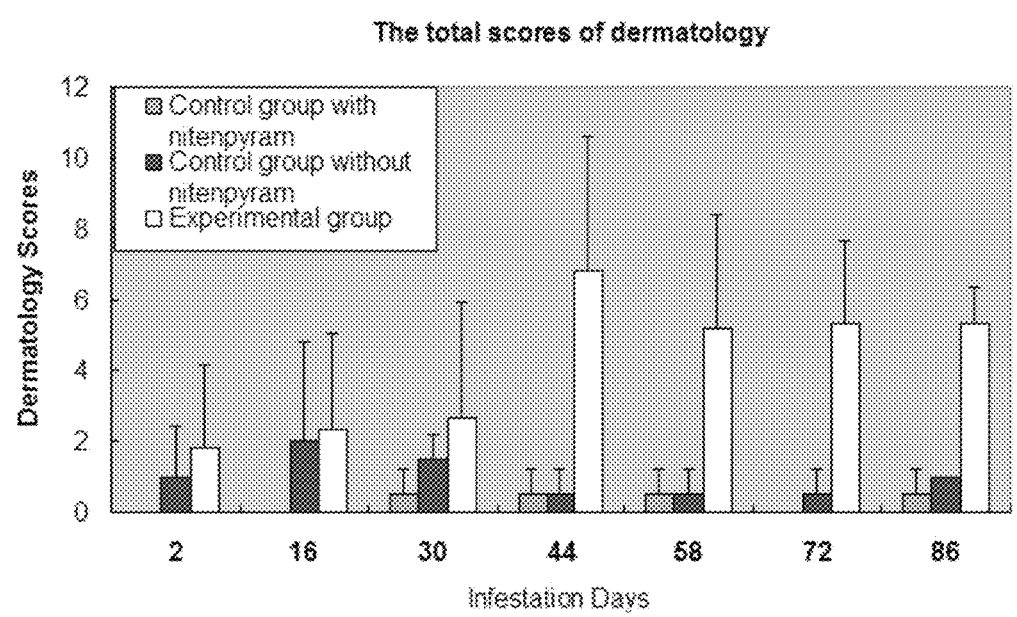
FIGS. 5a-5c shows dermatological scores data.
Figure 5B:
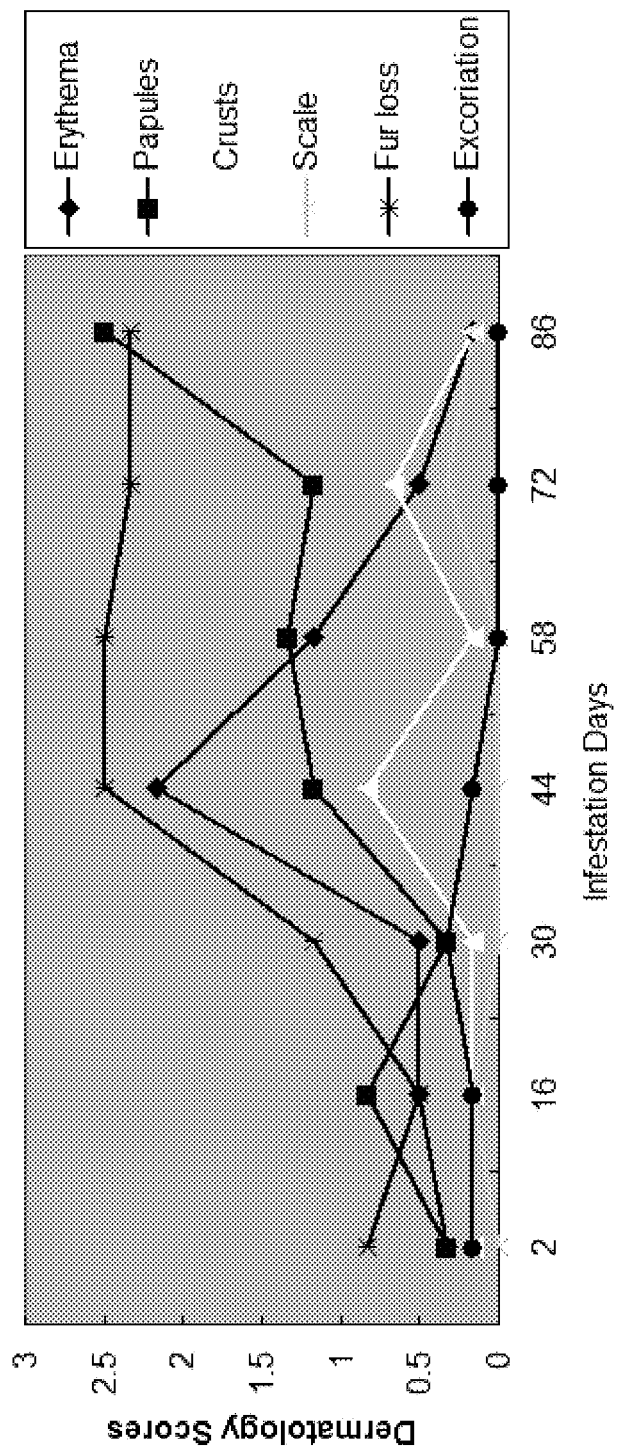
Figure 5C:
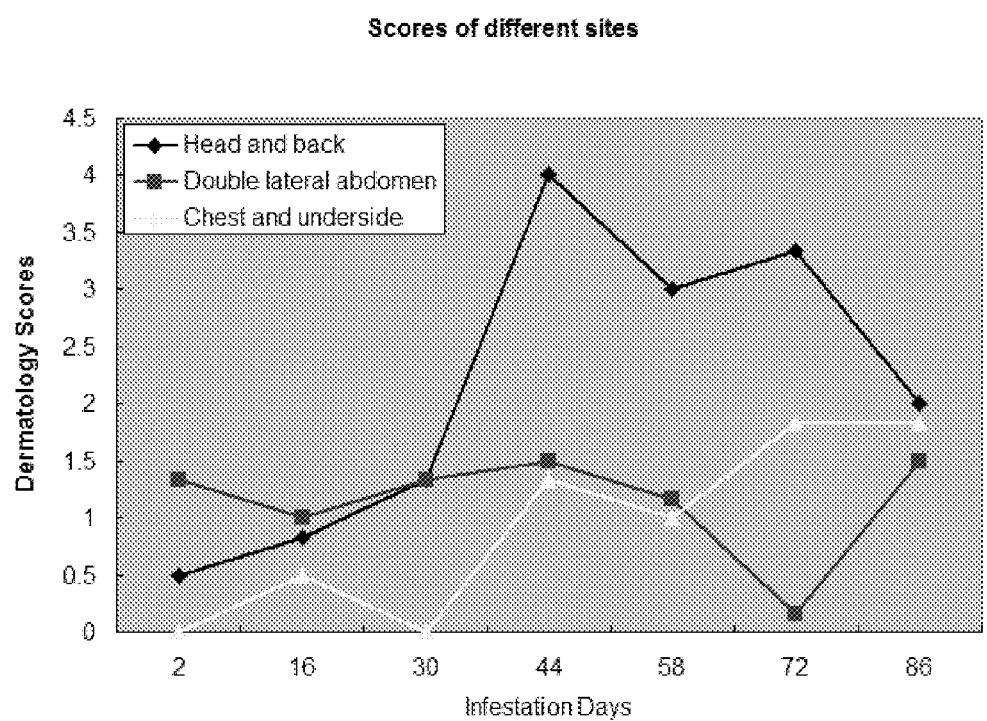

To eliminate the interference by the nitenpyram treatment, any differences between these treated with nitenpyram and the ones without treatment were assessed. From the dermatology score, no significant difference was seen in the control groups. Thus, the nitenpyram treatment did not influence the results obtained from our experiments (FIG. 5).

Cell Percentage in Peripheral Blood by Blood Smear Analysis

A comparison of the number of each type of cells in peripheral blood from the different groups showed that the number of eosinophils was higher in the experimental group than those in control groups. Blood smears were performed for each infestation cycle, but the percent of each type of cells became constant after the third cycle. As the result from day 58 show in Table 3, the significant changes occurred in the number of eosinophils among the three groups. Since the increase of eosinophils is related to allergic diseases as previously documented, these results indicate that the cats in the experimental group were more susceptible to the infestation of fleas. There was no obvious difference between the two control groups, the nitenpyram seems not to interfere the cell numbers in the cats' peripheral blood.

TABLE 3

Cell types and their percentage in peripheral blood

| | Lymphocytes (%) | Monocytes (%) | Neutrophils (%) | Basophils (%) | Eosinophils (%) |
|---|---|---|---|---|---|
| Experimental group | 23.4 | 2.6 | 61.5 | 1.0 | 11.5 |
| Control group with nitenpyram | 21.8 | 3.6 | 70.5 | 0.7 | 3.4 |
| Control group without nitenpyram | 23.1 | 3.6 | 68.3 | 0.6 | 4.4 |

Histopathological Examination

First, the differences between the normal skins and those with lesions were analyzed. Skin biopsies were chosen from all groups on day 58. However, the skin biopsies from one cat may also display differences in some degree, especially those with lesions. That was not enough to indicate whether the cats infestated with fleas were induced to have FAD. For this reason, the skin biopsies from each group were collected after the IDT with the flea extracts since IDT with flea provides an antigen specific recalled immune responses.

Skin Test to Evaluate Whether the Cats were Allergic to the Flea Extracts.

Figure 6:
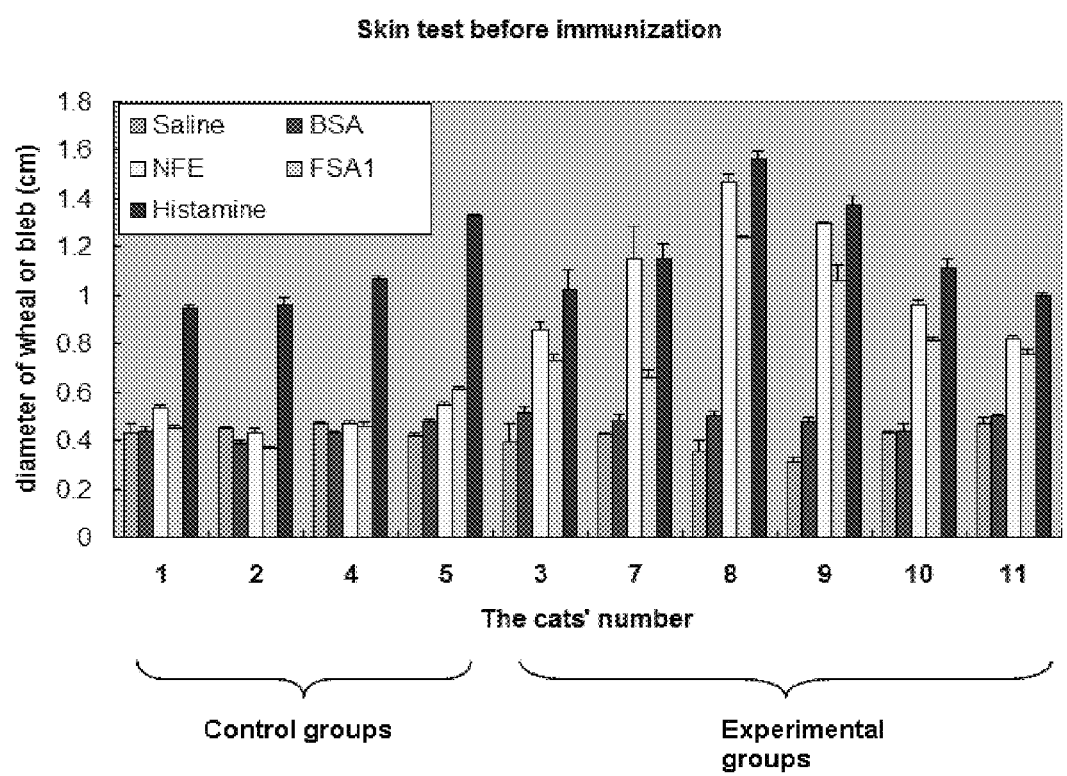
FIG. 6 shows results of skin tests before co-immunization.

The diameter of wheal or bleb was measured 15 min after the IDT injection. Since each cat had a different level of sensitivity to the IDT, the results from each individual animal were recorded. FIG. 6 shows the skin reactions in all groups. An allergic reaction was considered to have occurred if an IDT value was above the average of threshold (the sum of saline and histamine is divided by 2), or not occurred if an IDT value was below the average of the threshold. The results are shown in Table 4. Cats with dermatology scores at 5.0 or above were identified as the positive for FAD.

TABLE 4

Comparison of dermatological assessment with the intradermal skin test (IDT).

| Cat No. | Experimental group | Control group with nitenpyram | Control group without nitenpyram | Dermatology scores | Positive clinical scores | Positive skin test with BSA | Positive skin test with flea extract | Positive skin test with FS | Positive skin test with FSA1 |
|---|---|---|---|---|---|---|---|---|---|
| 1 | No | Yes | No | 0 | − | − | − | − | − |
| 2 | No | No | Yes | 1 | − | − | − | − | − |
| 4 | No | Yes | No | 1 | − | − | − | − | − |
| 5 | No | No | Yes | 0 | − | − | − | − | − |
| 3 | Yes | No | No | 7 | + | − | + | − | + |
| 7 | Yes | No | No | 6 | + | − | + | − | − |
| 8 | Yes | No | No | 8 | + | − | + | − | + |
| 9 | Yes | No | No | 2 | − | − | + | − | + |

TABLE 4-continued

Comparison of dermatological assessment with the intradermal skin test (IDT).

| Cat No. | Experimental group | Control group with nitenpyram | Control group without nitenpyram | Dermatology scores | Positive clinical scores | Positive skin test with BSA | Positive skin test with flea extract | Positive skin test with FS | Positive skin test with FSA1 |
|---|---|---|---|---|---|---|---|---|---|
| 10 | Yes | No | No | 6 | + | − | + | − | + |
| 11 | Yes | No | No | 3 | − | − | + | − | + |

Skin Test to Determine the Effect of Co-Immunization of FSA1 and pVAX-FSA1

The cats with FAD were co-immunized with FSA1+pVAX-FSA1 or vector+FSA1 as described in experimental design B in Table 2. Before and after the immunizations, the cats were tested by IDT with various flea antigens or control antigens. The IDT readings were recorded on 7 days after the last immunization as summarized in FIG. 7 and Table 5.

The results showed that FAD cats co-immunized with the FSA1+pVAX-FSA 1 had less skin-reactions to the flea extracts or flea specific antigens (such as FSA 1 protein) challenges; whereas the cats immunized with vector+FSA1 had more skin-reactions to the same challenges.

Figure 7:
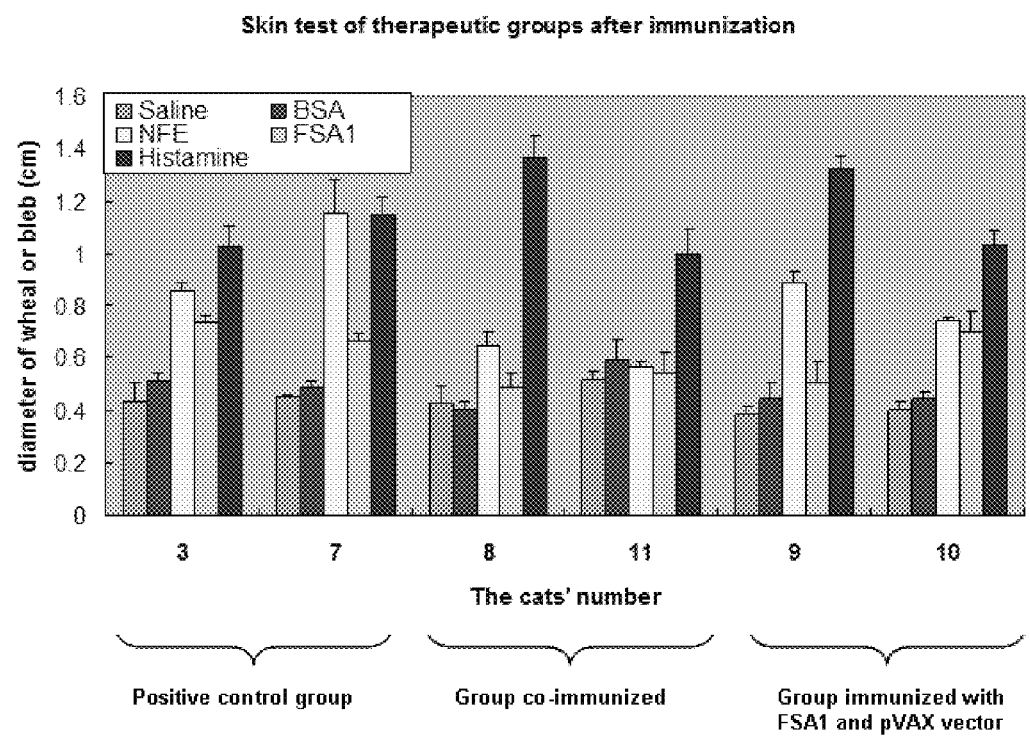
FIG. 7 shows results of skin tests after co-immunization.

Comparing the differences before and after immunization, we observed that the skin reaction was much smaller after the immunization than before in the co-immunized group as shown FIG. 7, suggesting the co-immunization significant decreased sensitivity to the flea challenge. On contrary, no significant effect was seen in groups immunized with FSA1 and pVAX vector, indicating that the cats were remained their allergic status. The status of all cats was listed in Table 5.

Figure 10A:
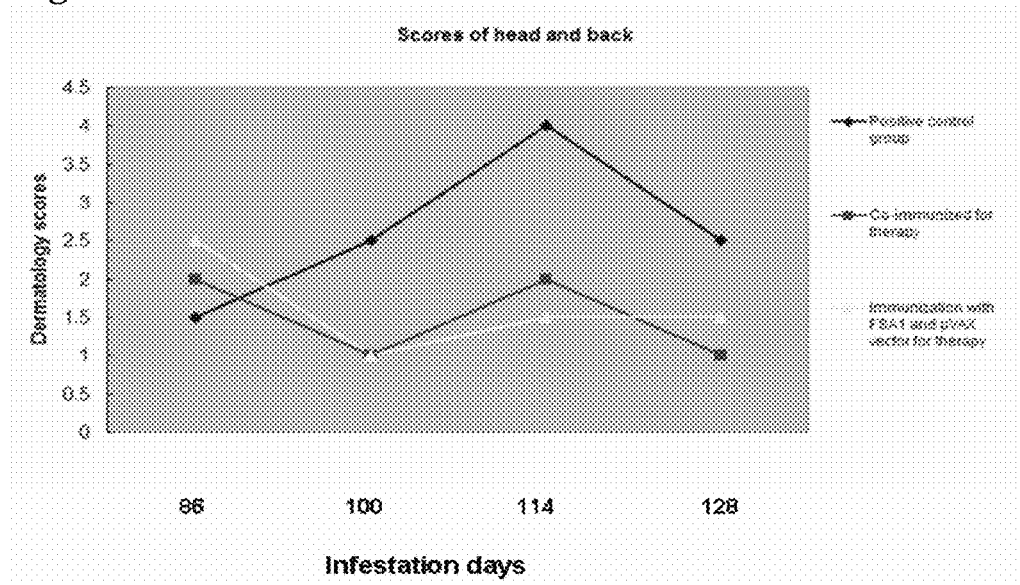
FIGS. 10A-10C show data demonstrating therapeutic effects of co-immunization on the FAD cats.
Figure 10B:
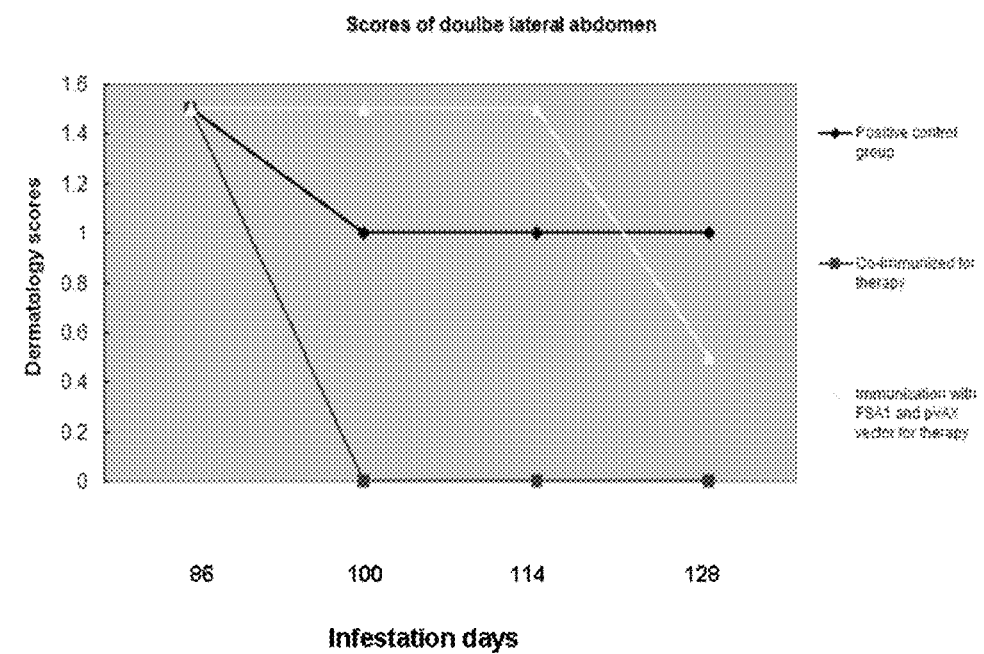
Figure 10C:
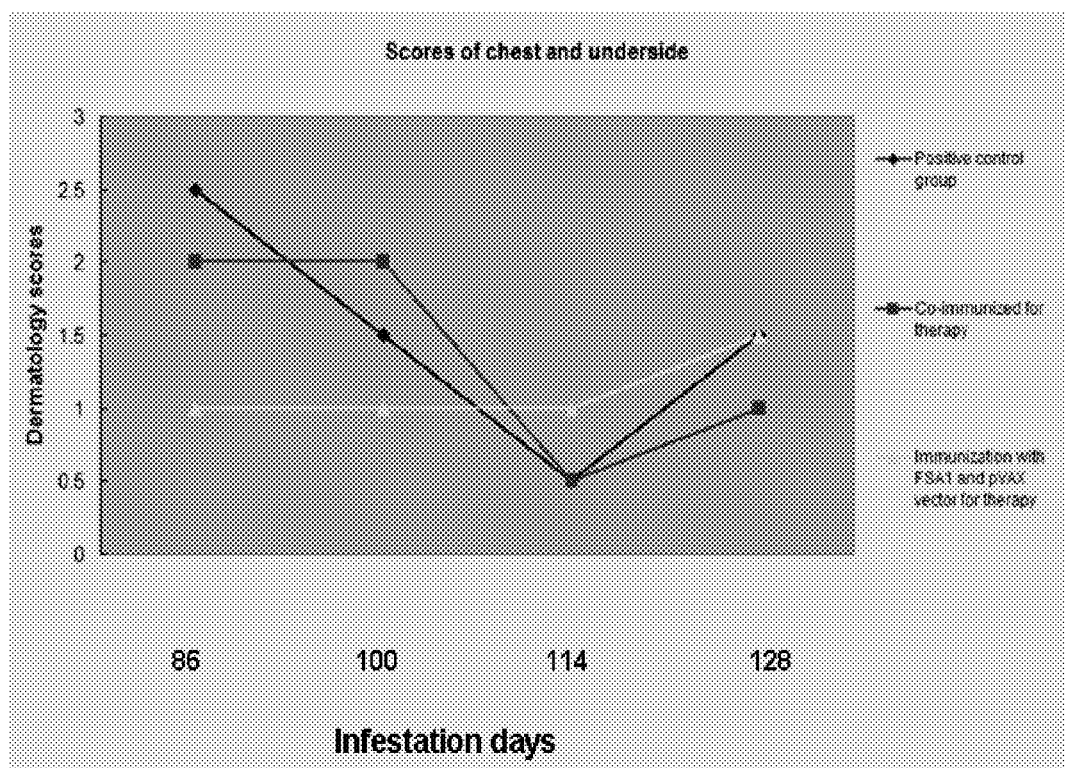

Correlation of the Location of Lesions Affected by the Co-Immunization on the FAD Cats Therapeutic Effects of Co-Immunization on the FAD Cats After analysis the correlation, the data showed that the scores of double lateral abdomen in therapeutic group were reduced from 1.5 to 0 (FIG. 10B) after the co-immunization of FSA 1+pVAX-FSA1, but no effect in the other places as shown in FIGS. 10A-10C. The therapeutic group immunized with FSA I and pVAX vector showed a lingering response (FIG. 10B, triangle points). The dermatologic scores of FAD cats immunized with FSA1 and pVAX vector were reduced from 1.5 to 0.5 after 7 days of the last immunization. In contrast, those in the co-immunized with FSA1+pVAX-FSA1 were reduced promptly after its first immunization and remained at low level thorough (FIG. 10B, square points).

Summary

These data demonstrate the successful induction of a FAD model in feline by flea infestations. Physiological or pathogenic parameters in the FAD feline have been characterized which can be used as a model to evaluate treatment of immunotherapeutic or prophylactic approaches.

TABLE 5

| Cat No. | Positive control | FSA1 and pVAX | FSA1 + pVAX − FSA1 | IDT with BSA | IDT with flea extracts | IDT with FSA1 | The state for FE before immunization |
|---|---|---|---|---|---|---|---|
| 1 | No | Yes | No | | | | − |
| 2 | No | No | Yes | | | | − |
| 4 | No | No | Yes | | | | − |
| 5 | No | Yes | No | | | | − |
| 3 | Yes | No | No | − | + | − | + |
| 7 | Yes | No | No | − | + | − | + |
| 8 | No | No | Yes | − | − | − | + |
| 9 | No | Yes | No | − | + | − | + |
| 10 | No | Yes | No | − | + | − | + |
| 11 | No | No | Yes | − | − | − | + |

Therapeutic Effects of Co-Immunization on the FAD Cats

Figure 8:
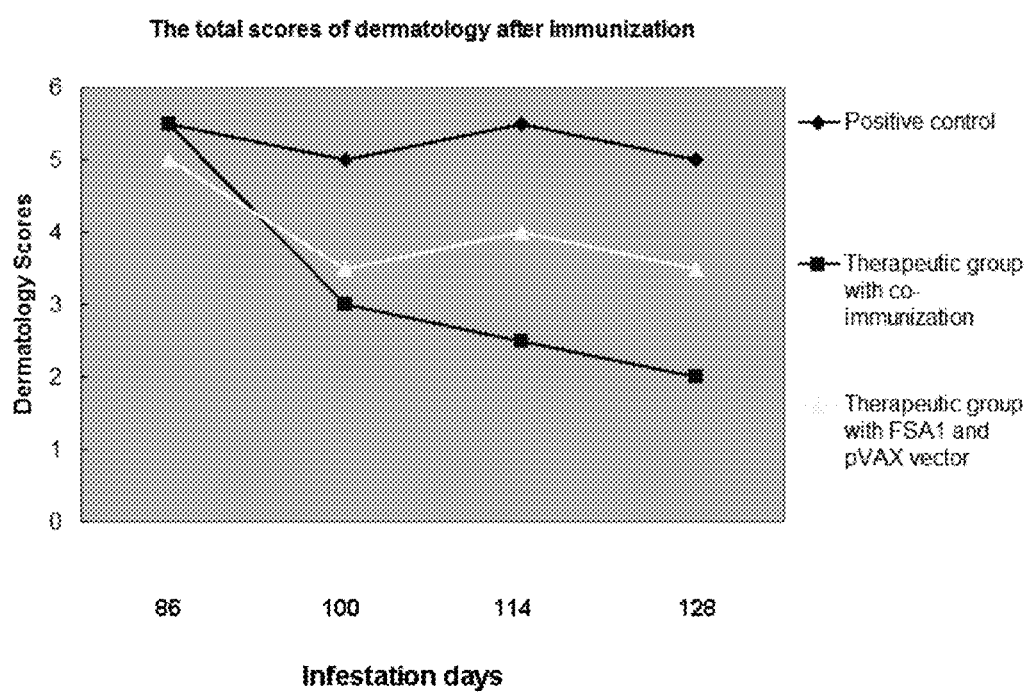
FIG. 8 shows dermatological scores data after co-immunization.

To determine the therapeutic effect of co-immunization on lesions of the FAD cats, the lesions were recorded over period of 53 days after the first immunization and shown in FIG. 8. The lesion scores in the co-immunized group were dramatically reduced from 5.5 to 2 (FIG. 8, square points on line). Whereas, the effects on the group immunized with FSA 1 and pVAX vector was reduced but to a lesser extent (FIG. 8, triangle points on line). The result suggested the co-immunization had a therapeutic effect on the established FAD in cats.

Figure 9A:
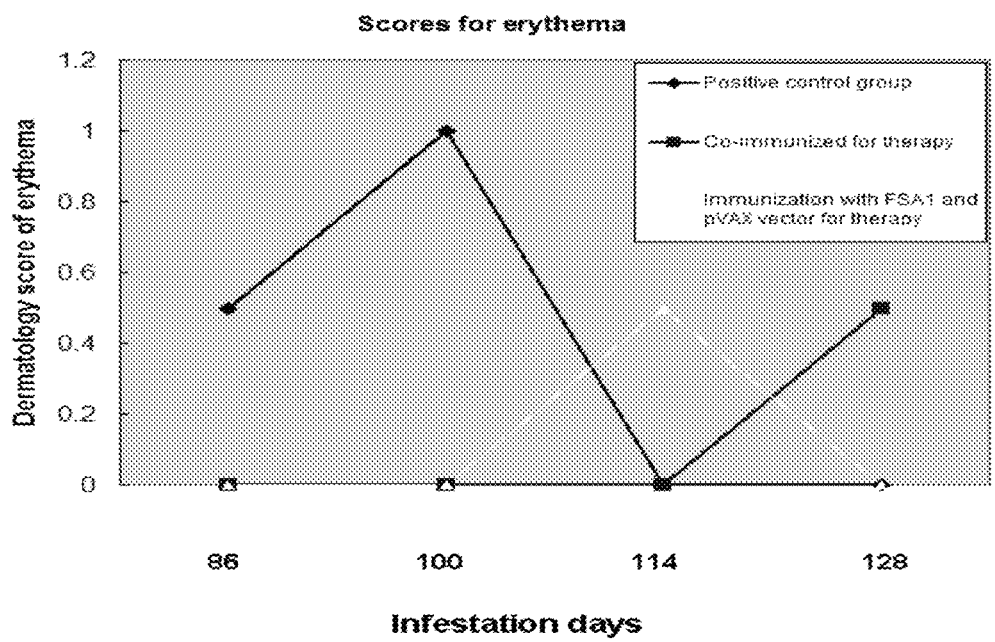
FIGS. 9A-9F show data demonstrating therapeutic effects of co-immunization on the FAD cats.
Figure 9B:
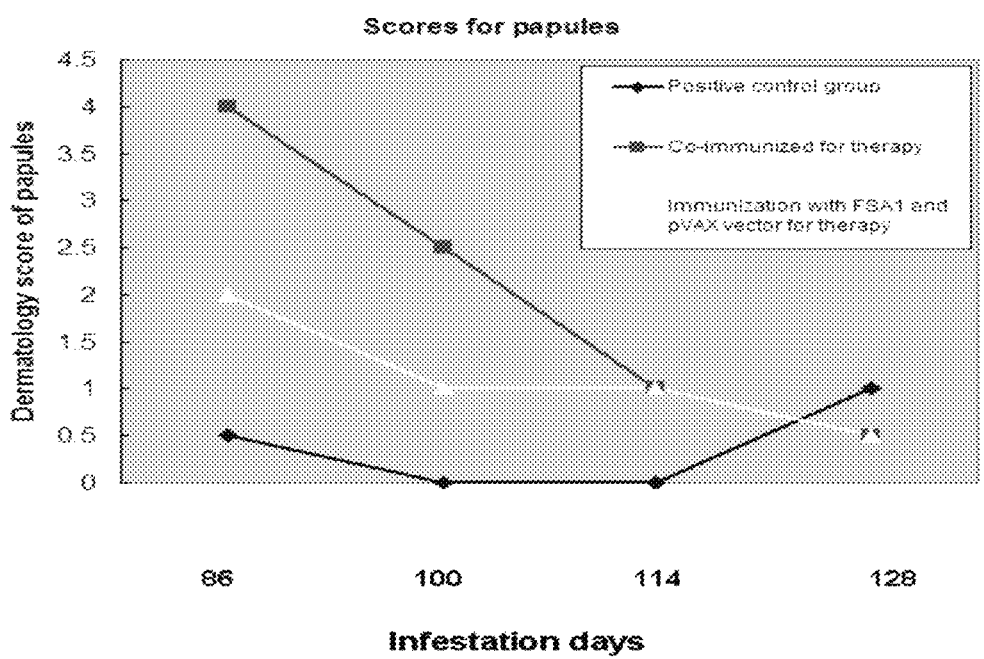
Figure 9C:
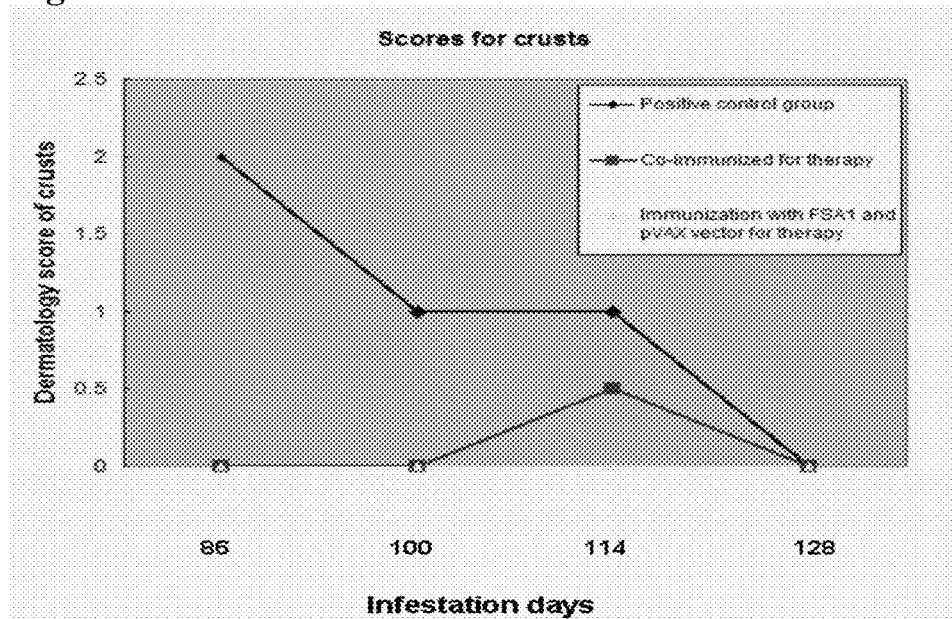
Figure 9D:
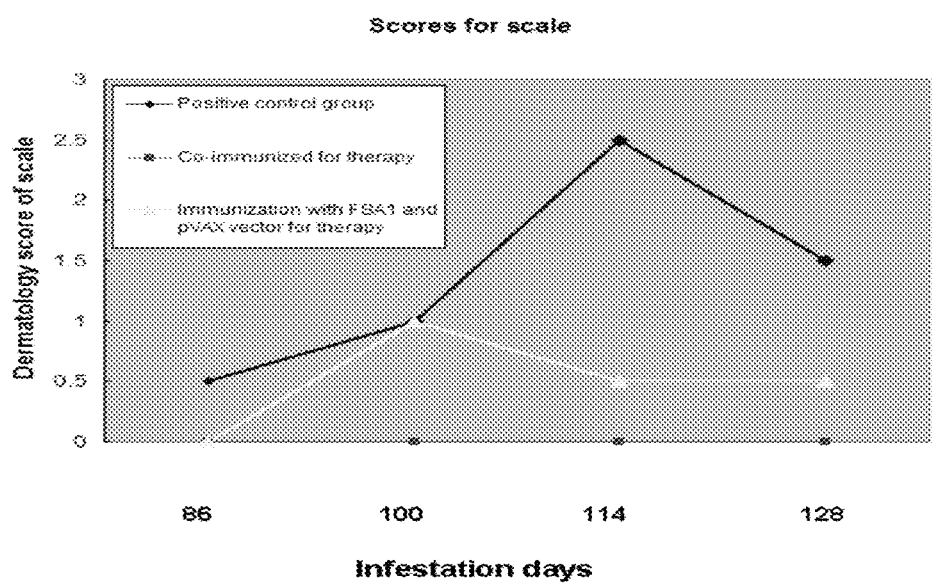
Figure 9E:
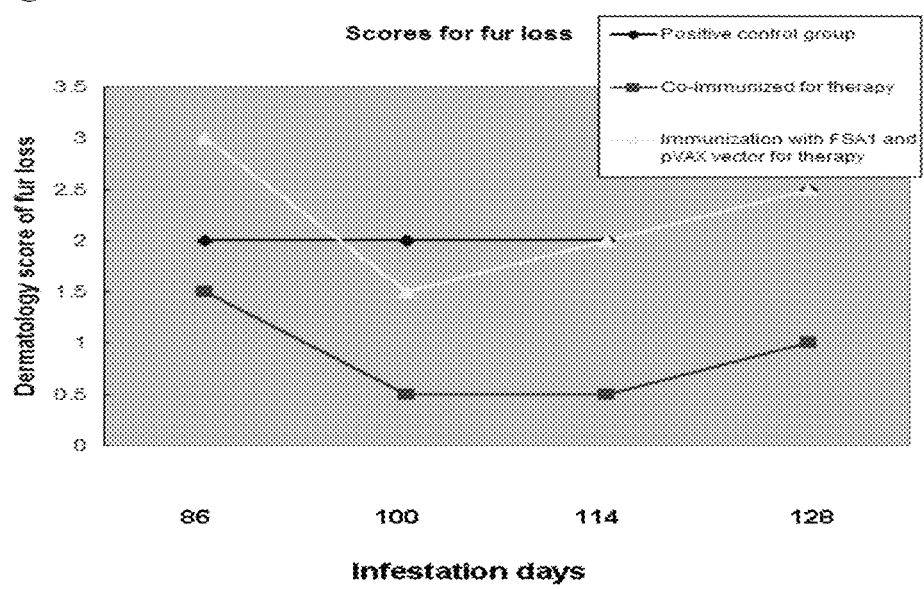
Figure 9F:
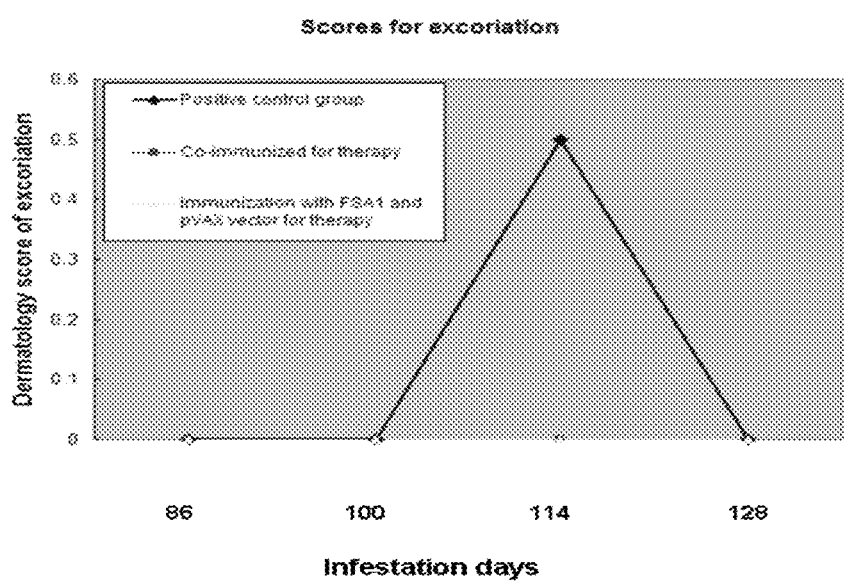

Correlation of the Type of Lesions Affected by the Co-Immunization on the FAD Cats To correlate which type of lesions reduced with the co-immunization, the scores on each type of lesions in every group were analyzed and the results are shown in FIG. 9A-9F. Only the score of the papules were reduced from 4.0 to 0.5 and coincident with the co-immunization of FSA1+pVAX-FSA1 (FIG. 9B, square points on line). Other type of lesions in experimental group was remained unchanged.

The co-immunization of FSA1+pVAX-FSA1 vaccines was demonstrated to suppress the established FAD in cats. Such suppression seems to be an antigenic specific, which supports the results observed in mouse studies.

Example 18 pVAX1-K-FSA1

Figure 11:
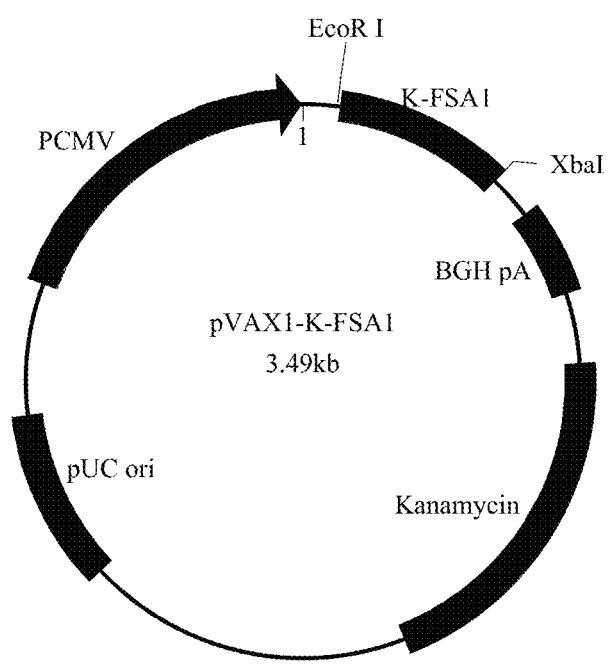
FIG. 11 shows a map of plasmid pVAX1-K-FSA1.

Plasmid pVAX 1-K-FSA 1 comprises the FSA 1 coding sequence linked to a Kozak sequence in plasmid backbone pVAX (Invitrogen). The sequence of the K-FSA1 insert is SEQ ID NO:61. Nucleotides 1-9 correspond to the Kozak sequence. the open reading from of FSA 1 plus missed 8 amino acids begins at nucleotide 10. A map of the plasmid pVAX1-K-FSA1 is shown in FIG. 11.

The invention claimed is:

1. A method of inhibiting an allergic reaction to a flea allergenic protein in an individual comprising the step of administering to the individual a) an eukaryotic cell expression vector containing nucleotide sequences encoding a flea allergenic protein or a polypeptide that comprises an antigenic epitope of said flea allergenic protein, wherein said nucleotide sequence encodes an amino acid sequence comprising SEQ ID NO. 2; and
   b) a flea allergenic protein or a polypeptide encoded by said nucleotide sequence.

2. The method of claim 1, wherein said nucleotide sequence encoding an amino acid sequence comprising SEQ ID NO. 2 is operably linked to a promoter.

3. The method of claim 2, wherein the promoter is selected from the group consisting of RSV, CMV, and SV40 promoters.

4. The method of claim 1, wherein the ratio of amount of eukaryotic cell expression vector by weight to amount of the protein or the polypeptide encoded by said nucleotide sequence by weight is between 1:5 and 5:1.

5. The method of claim 1, wherein the ratio of amount of eukaryotic cell expression vector by weight to amount of the protein or the polypeptide encoded by said nucleotide sequence by weight is 1:1.

6. The method of claim 1, wherein the molar ratio of eukaryotic cell expression vector to the protein or the polypeptide encoded by said nucleotide sequence is between 1:100,000 to 20:100,000.

7. The method of claim 1, wherein the molar ratio of eukaryotic cell expression vector to the protein or the polypeptide encoded by said nucleotide sequence is 15:100,000.

8. The method of claim 1, wherein the nucleotide sequence encodes an amino acid sequence consisting of SEQ ID NO. 2.

9. The method of claim 1, wherein the eukaryotic cell expression vector and the allergenic protein or polypeptide are administered together.

10. The method of claim 1, wherein the eukaryotic cell expression vector and the allergenic protein or polypeptide are administered separately.

\* \* \* \* \*